US008747843B2

(12) United States Patent
Giroir et al.

(10) Patent No.: US 8,747,843 B2
(45) Date of Patent: Jun. 10, 2014

(54) METHOD OF TREATMENT AND BIOASSAY INVOLVING MACROPHAGE MIGRATION INHIBITORY FACTOR (MIF) AS CARDIAC-DERIVED MYOCARDIAL DEPRESSANT FACTOR

(75) Inventors: Brett P. Giroir, Vienna, VA (US); Monte S. Willis, Chapel Hill, NC (US); Vidal F. De La Cruz, Jr., Phoenixville, PA (US); Thais M. Sielecki-Dzurdz, Kennett Square, PA (US)

(73) Assignees: Baxter International, Inc., Deerfield, IL (US); Baxter Healthcare SA, Glattpark, Opfikon (CH); Board of Regents, The University of Texas System, Austin, TX (US)

( * ) Notice: Subject to any disclaimer, the term of this patent is extended or adjusted under 35 U.S.C. 154(b) by 936 days.

(21) Appl. No.: 11/932,909

(22) Filed: Oct. 31, 2007

(65) Prior Publication Data
US 2008/0260723 A1 Oct. 23, 2008

Related U.S. Application Data

(63) Continuation of application No. 10/927,494, filed on Aug. 27, 2004, now abandoned.

(60) Provisional application No. 60/498,659, filed on Aug. 29, 2003, provisional application No. 60/547,054, filed on Feb. 25, 2004, provisional application No. 60/547,056, filed on Feb. 25, 2004, provisional application No. 60/547,057, filed on Feb. 25, 2004, provisional application No. 60/547,059, filed on Feb. 25, 2004, provisional application No. 60/556,440, filed on Mar. 26, 2004.

(51) Int. Cl.
*A61K 39/395* (2006.01)
*A61K 39/40* (2006.01)
*A61K 39/00* (2006.01)
*C07K 16/00* (2006.01)

(52) U.S. Cl.
USPC ................. 424/130.1; 424/141.1; 424/145.1; 424/158.1; 424/178.1; 424/184.1; 424/192.1

(58) Field of Classification Search
None
See application file for complete search history.

(56) References Cited

U.S. PATENT DOCUMENTS 6,030,615 A 2/2000 Bucala et al.
6,228,359 B1 5/2001 Horwitz
6,645,493 B1 * 11/2003 Bucala et al. .............. 424/145.1

FOREIGN PATENT DOCUMENTS

WO 0164749 9/2001
WO 2005020919 1/2011

OTHER PUBLICATIONS

Lue et al. Microbes and Infection 20024:449-460.*
Krishnagopalan et al. BioDrug 2001, 15(10):645-654.*
Calandra et al. Natuer Medicine, 2000, 6(2):164-170.*
Engelmann et al. JBC 1990, 265(24):14497-14504.*
S. Krishnagopalan, et al., "Myocardial Dysfunction in the Patient with Sepsis", Curr. Opin. Crit. Care, 8, 376-388, 2002.
A. Kumar, et al., "Tumor Necrosis Factor Alpha and Interleukin I Beta are Responsible for in vitro Myocardial Cell Depression Induced by Human Septic Shock Serum", J, Exp. Med., 183, 949-958, 1996.
K.N. Lai, et al., "Role for macrophage migration inhibitory factor in acute respiratory distress syndrome", J Pathol 199: 496-508, 2003.
Lan, H.Y., et al., "De Novo Renal Expression of Macrophage Migration Inhibitory Factor During the Development of Rat Crescentic Glomerulonephritis", Am. J. Pathol., 149, 1119-1127, 1996.
Lan, H.Y., et al., "Macrophage Migration Inhibitory Factor Expression in Human Renal Allograft Rejection", Transplantation, 66, 1465-1471, 1998.
Lan, H.Y., et al., "TNF-Alpha Up-Regulates Renal MIF Expression in Rat Crescentic Glomerulonephritis", Mol. Med., 3, 136-144, 1997.
K. Last-Barney, et al., "Synergistic and overlapping activities of tumor necrosis factor-alpha and IL-1", J Immunol 141: 527-530, 1988.
M. Leech, et al., "Macrophage Migration Inhibitory Factor in Rheumatoid Arthritis: Evidence of Proinflammatory Function and Regulation by Glucocorticoids", Arthritis Rheum, 42, 1601-1608, 1999.
M. Leech, et al., "Involvement of macrophage migration inhibitory factor in the evolution of rat adjuvant arthritis", Arthritis Rheum 41: 910-917, 1998.
A.M. Lefer "Mechanisms of Cardiodepression in Endotoxin Shock", Circ Shock Suppl 1: 1-8, 1979.
L.E. Lehmann "Plasma Levels of macrophage Migration Inhibitory Factor are Elevated in Patients with Severe Sepsis", Intensive Care Med., 27, 1412-1415, 2001.

(Continued)

*Primary Examiner* — Chun Dahle
(74) *Attorney, Agent, or Firm* — John K. Pike; Nevrivy Patent Law Group, PLLC

(57) ABSTRACT

One embodiment of the present invention relates to a pharmaceutical composition, which includes a therapeutically effective amount of at least one anti-MIF antibody; and at least one pharmaceutically acceptable carrier. Another embodiment of the present invention relates to a pharmaceutical composition, which includes a therapeutically effective amount at least one anti-CD74 antibody; and at least one pharmaceutically acceptable carrier. Another embodiment of the present invention relates to a pharmaceutical composition, which includes a therapeutically effective amount of at least one anti-TNFR antibody; a therapeutically effective amount of at least one anti-MIF antibody; and at least one pharmaceutically acceptable carrier. Other embodiments of the present invention relate to methods of treating or preventing cardiac dysfunction, cardiodepression, burn injury-associated cardiac dysfunction, improving cardiac function in a subject following acute myocardial infarction, and identifying an MIF inhibitor.

4 Claims, 31 Drawing Sheets

(56) References Cited

OTHER PUBLICATIONS

L. Leng, et al., "MIF signal transduction initiated by binding to CD74", J Exp Med 197: 1467-1476, 2003.
J.B. Lubetsky, et al., "The tautomerase active site of macrophage migration inhibitory factor is a potential target for discovery of novel anti-inflammatory agents", J Biol Chem 277: 24976-24982, 2002.
H. Lue, et al., "Macrophage Migration Inhibitory Factor (MIF): Mechanisms of Action and Role in Disease", Microbes Infect., 4: 449-460, 2002.
H. Makita, et al., "Effect of Anti-Macrophage Migration Inhibitory Factor Antibody on Lipopolysaccharide-Induced Pulmonary Neutrophil Accumulation", Am. J. Respir. Crit. Care Med., 158: 573-579, 1998.
D.L. Maass, et al., "IL-1 beta and IL-6 act synergistically with TNF-alpha to alter cardiac contractile function after burn trauma", Shock 18: 360-366, 2002.
X. Meng, et al., "TNF-alpha and myocardial depression in endotoxemic rats: temporal discordance of an obligatory relationship", Am J Physiol 275: R502-508, 1998.
K. Meyer-Siegler, et al., "Increased Stability of Macrophage Migration Inhibitory Factor (MIF) in Du-145 Prostate Cancer Cells", J. Interferon Cytokine Res., 20: 769-778, 2000.
A. Mikulowska, et al., "Macrophage Migration Inhibitory Factor is Involved in the Pathogenesis of Collagen Type II-Induced Arthritis in Mice", J. Immunol., 158: 55 14-551 7, 1997.
R.A. Mitchell, et al., "Tumor Growth-Promoting Properties of Macrophage Migration Inhibitory Factor (MIF)", Semin. Cancer Biol., 10: 359-366, 2000.
R. A. Mitchell, et al., "Sustained mitogen-activated protein kinase (MAPK) and cytoplasmic phospholipase A2 activation by macrophage migration inhibitory factor (MIF). Regulatory role in cell proliferation and glucocorticoid action", J Biol Chem 274: 18100-18106, 1999.
B. Mozetic-Francky, et al., "High-yield expression and purification of recombinant human macrophage migration inhibitory factor", Protein Expr Purf 9: 115-124, 1997.
J.T. Murphy, et al., "Evaluation of troponin-I as an indicator of cardiac dysfunction after thermal injury", J Trauma 45: 700-704, 1998.
C. Natanson, et al., "Selected treatment strategies for septic shock based on proposed mechanisms of pathogenesis", Ann Intern Med 120: 771-783, 1994.
C. Natanson, et al., "Endotoxin and Tumor Necrosis Factor Challenges in Dogs Simulate the Cardiovascular Profile of Human Septic Shock", Journal of Experimental Medicine, 169: 823-932, 1989.
T. Nishino, et al., "Localization of macrophage migration inhibitory factor (MIF) to secretory granules within the corticotrophic and thyrotrophic cells of the pituitary gland", Mol Med 1: 781-788, 1995.
T. Ohkawara, et al., "Amelioration of dextran sulfate sodium-induced colitis by anti-macrophage migration inhibitory factor antibody in mice", Gastroenterology 123: 256-270, 2002.
S. Okusawa, et al., "Interleukin 1 induces a shock-like state in rabbits. Synergism with tumor necrosis factor and the effect of cyclooxygenase inhibition", J Clin Invest 81: 1162-1172, 1988.
S. Ono, et al., "Severe sepsis induces deficient interferon-gamma and interleukin-12 production, but interleukin-12 therapy improves survival in peritonitis", Am J Surg 182: 491-497, 2001.
M. Orita, et al., "Macrophage Migration Inhibitory Factor and the Discovery of Tautomerase Inhibitors", Curr. Pharm. Des., 8: 1297-1317, 2002.
M. Parker, et al., "Right Ventricular Dysfunction and Dilatation, Similar to Left Ventricular Changes, Characterize the Cardiac Depression of Septic Shock in Humans", Chest, 97: 126-131, 1990.
J.E. Parrillo, et al., "A circulating myocardial depressant substance in humans with septic shock. Septic shock patients with a reduced ejection fraction have a circulating factor that depresses in vitro myocardial cell performance", J Clin Invest 76: 1539-1553, 1985.
J.J. Peschon, et al., "TNF receptor-deficient mice reveal divergent roles for p55 and p75 in several models of inflammation", J Immunol 160: 943-952, 1998.
A. Poltorak, et al., "Defective LPS Signaling in C3H/HeJ and C57BL/10ScCr Mice: Mutations in Tlr4 Gene", Science, 282: 2085-2088, 1998.
A. Poltorak, et al., "Genetic and Physical Mapping of the Lps Locus: Identification of the Toll-4 Receptor as a Candidate Gene in the Critical Region", Blook Cells Mol. Dis., 240: 340-355, 1998.
M. E. Pyle, et al., "Macrophage migration inhibitory factor expression is increased in pituitary adenoma cell nuclei", J Endocrinol 176: 103-110, 2003.
S. T. Qureshi, et al., "Endotoxin-Tolerant Mice Have Mutations in Toll-Like Receptor 4 (Tlr4)", J. Exp. Med., 189: 615-625, 1999.
C. D. Raebum, et al., "Neutralization of IL-18 attenuates lipopolysaccharide-induced myocardial dysfunction" Am J Physiol Heart Circ Physiol 283: H650-657, 2002.
E. K. Rice, et al., "Induction of MIF synthesis and secretion by tubular epithelial cells: A novel action of angiotensin II", Kidney Int 63: 1265-1275, 2003.
J.M. Reilly, et al., "A circulating myocardial depressant substance is associated with cardiac dysfunction and peripheral hypoperfusion (lactic acidemia) in patients with septic shock", Chest 95: 1072-1080, 1989.
K. Reinhart, et al., "Assessment of the safety and efficacy of the monoclonal anti-tumor necrosis factor antibody-fragment, MAK 195F, in patients with sepsis and septic shock: a multicenter, randomized, placebo-controlled, dose-ranging study", Crit Care Med 24: 733-742, 1996.
K. Reinhart, et al. "Anti-tumor necrosis factor therapy in sepsis: update on clinical trials and lessons learned", Crit Care Med 29: S121-125, 2001.
E. M. Reynolds, et al., "Left ventricular failure complicating severe pediatric burn injuries", J Pediatr Surg 30: 264-269-270, 1995.
T. Roger, et al., "MIF Regulates Innate Immune Responses Through Modulation of Toll-Like Receptor 4", Nature, 414: 920-924, 2001.
A. G. Rossi, et al., "Human Circulating Eosinophils Secrete Macrophage Migration Inhibitory Factor (MIF). Potential Role in Asthma", J. Clin. Invest., 101: 2869-2874, 1998.
E. Rosengren, et al., "The immunoregulatory mediator macrophage migration inhibitory factor (MIF) catalyzes a tautomerization reaction", Mol Med 2: 143-149, 1996.
D. M. Roth, et al., "Impact of Anesthesia on Cardiac Function During Echocardiography in Mice", Am. J. Physiol., Heart Circ. Physiol., 282: H2134-H2140, 2002.
H. Saito, et al., "Expression and self-regulatory function of cardiac interleukin-6 during endotoxemia", Am J Physiol Heart Circ Physiol 279: H2241-2248, 2000.
D. B. Sanders, et al., "Comparison of tumor necrosis factor-alpha effect on the expression of iNOS in macrophage and cardiac myocytes", Perfusion 16: 67-74, 2001.
J. T. Sambol, et al., "Bum-induced impairment of cardiac contractile function is due to gut-derived factors transported in mesenteric lymph", Shock 18: 272-276, 2002.
M. G. Schwacha, et al., "Differential expression and tissue compartmentalization of the inflammatory response following thermal injury", Cyfokine 17: 266-274, 2002.
P. D. Senter, et al., "Inhibition of macrophage migration inhibitory factor (MIF) tautomerase and biological activities by acetaminophen metabolites", Proc Natl AcadSci US A 99: 144-149, 2002.
C. N. Sessler, et al., "New Concepts in Sepsis", Curr. Opin. Crit. Care, 8: 465-472, 2002.
T. Shimizu, et al., "High Expression of Macrophage Migration Inhibitory Factor in Human Melanoma Cells and Its Role in Tumor Cell Growth and Angiogenesis", Biochem. Biophys. Res. Commun., 264: 751-758, 1999.
T. Shimizu, et al., "Macrophage migration inhibitory factor is an essential immunoregulatory cytokine in atopic dermatitis", Biochem Biophys Res Commun 240: 173-178, 1997.
T. Shimizu, et al., "Identification of macrophage migration inhibitory factor (MIF) in human skin and its immmunohistochemical localization", FEBS Letters 381: 199-202, 1996.

(56) References Cited

OTHER PUBLICATIONS

T. Shimizu, et al., "Increased production of Macrophage Migration Inhibitory Factor by PBMCs of Atopic Dermatitis", J. Allergy Clin. Immunol., 104: 659-664, 1999.

Y. Shimomura, et al., "Changes in ambulatory activity and dopamine turnover in streptozotocin-induced diabetic rats", Endocrinology 123: 2621-2625, 1988.

W. C. Shoemaker, et al., "Burn pathophysiology in man. I. Sequential hemodynamic alterations", J Surg Res 14: 64-73, 1973.

H. G. Shu, et al., "The tumor necrosis factor receptor 2 signal transducers TRAF2 and c-IAP1 are components of the tumor necrosis factor receptor 1 signaling complex", Proc Nafl Acad Sci USA 93: 13973-13978, 1996.

A. F. Suffredini, et al., "The Cardiovascular Response of Normal Humans to the Administration of Endotoxin", New England Journal of Medicine, 321: 280-287, 1989.

M. Takahashi, et al., "Elevation of Plasma Levels of Macrophage Migration Inhibitory Factor in Patients with Acute Myocardial Infarction", Am. J. Cardiol., 89: 248-249, 2002.

M. Takahashi, et al., "Macrophage Migration Inhibitory Factor as a Redox-Sensitive Cytokine in Cardiac Myocytes", Cardiovasc Res., 52: 438-445, 2001.

Takahashi, et al., "Involvement of Macrophage Migration Inhibitory Factor (MIF) in the Mechanism of Tumor Cell Growth", Mol. Med., 4: 707-714, 1998.

J. A. Thomas, et al., "IRAK contributes to burn-triggered myocardial contractile dysfunction", Am J Physiol Heart Circ Physiol 283: H829-836, 2002.

J. A. Thomas, et al., "TLR4 inactivation and rBPI(21) block burn-induced myocardial contractile dysfunction", Am J Physiol Heart Circ Physiol 283: H1645-1655, 2002.

T. Utsunomiya, et al., "A mechanism of interleukin-12 unresponsiveness associated with thermal injury", J Surg Res 96: 211-217, 2001.

D. A. Vignali, "Multiplexed particle-based flow cytometric assays", J Immunol Methods 243: 243-255, 2000.

G. Wakabayashi, et al., "A specific receptor antagonist for interleukin 1 prevents *Escherichia coli*—induced shock in rabbits", FASEB J5: 338-343, 1991.

J. White, et al., "Development of an Acute Burn Model in Adult Mice for Studies of Cardiac Function and Cardiomyocyte Cellular Function", Shock, 16: 122-129, 2001.

J., White, et al., "Molecular and pharmacological approaches to inhibiting nitric oxide after burn trauma", Am J Physiol Heart Circ Physiol 285: H1616-1625, 2003.

R. R.Wolfe, "Review: acute versus chronic response to burn injury", Circ Shock 8: 105-115, 1981.

H. Yang, et al., "Reversing established sepsis with antagonists of endogenous high-mobility group box I", PNAS 101: 296-301, 2004.

C. M. Yu, et al., "Elevation of Plasma Level of Macrophage Migration Inhibitory Factor in Patients with Acute Myocardial Infarction", Am. J. Cardiol., 88: 774-777, 2001.

R. Abe et al., "Enhancement of macrophage migration inhibitory factory (MIF) expression in injured epidermis and cultured fibroblasts," Biochimica et Biophysica Acta 1500; pp. 1-9; 2000.

E. Abraham et al., "Double-blind randomised controlled trial of monoclonal antibody to human tumour necrosis factor in treatment of septic shock," The Lancet, Infectious Diseases, vol. 351, No. 9107, pp. ; Mar. 28, 1998.

T. Calandra et al. "The Macrophage is an Important and Previously Unrecognized Source of Macrophage Migration Inhibitory Factor," J. Exp. Med, The Rockefeller University Press, vol. 179: 1895-1902, Jun. 1994.

R. Kleemann, et al., "Disulfide analysis reveals a role for macrophage migration inhibitory factor (MIF) as thiol-protein oxidoreductase", J Mol Biol 280: 85-102, 1998.

TNF-alpha Mab Sepsis Study Group, JAMA 273: 934-941, 1995.

P. Ammann, et al., "Elevation of Troponin I in Sepsis and Septic Shock", Intensive Care Med., 27, 965-969, 2001.

M. Bacher, et al., "Migration Inhibitory Factor Expression in Experimentally Induced Endotoxemia", Am. J. Pathol., 150, 235-246, 1997.

P. Baron, et al., "Gut failure and translocation following burn and sepsis", J. Surg. Res. 57: 197-204, 1994.

J. Bernhagen, et al., "An Essential Role for Macrophage Migration Inhibitory Factor in the Tuberculin Delayed-Type Hypersensitivity Reactor", J. Exp. Med., 183, 277-282 (1996).

J. Bernhagen, et al., "Regulation of the Immune Response by Macrophage Migration Inhibitory Factor: Biological and Structural Features", J. Mol. Med., 76, 151-161 (1998).

J. Bernhagen, et al., "MIF is a Pituitary-Derived Cytokine that Potentiates Lethal Endotoxaemia", Nature, 365, 756-759, 1993.

B. Beutler, et al., "Passive immunization against cachectin/tumor necrosis factor protects mice from lethal effect of endotoxin", Science, 229:869-871, 1985.

M. Bhatia, et al., "Role of Inflammatory Mediators in the Pathophysiology of Acute Respiratory Distress Syndrome", J. Pathol. 202: 145-156, 2004.

M. Bozza, et al., "Targeted Disruption of Migration Inhibitory Factor Gene Reveals its Critical Role in Sepsis", J. Exp. Med. 189,341-346, 1999.

R. Kleemann, et al., "Intracellular action of the cytokine MIF to modulate AP-1 activity and the cell cycle through Jab 1", Nature 408: 211-216, 2000.

A. Burger-Kentischer, et al., "Expression of Macrophage Migration Inhibitory Factor in Different Stages of Human Atherosclerosis", Circulation 105: 1561-1566, 2002.

T. Calandra, et al., "MIF as a Glucocorticoid-Induced Modulator of Cytokine Production", Nature, 377, 68-71, 1995.

T. Calandra, et al, "Macrophage Migration Inhibitory Factor (MIF): A Glucocorticoid Counter-Regulator Within the Immune System", Crit. Rev. Immunol., 17, 77-88, 1977.

T. Calandra, et al., "Protection from Septic Shock by Neutralization of Macrophage Migration Inhibitory Factor", Nat. Med., 6, 164-170, 2000.

T. Calandra, et al., "Macrophage Migration Inhibitory Factor is a Critical Mediator of the Activation of Immune Cells by Exotoxins of Gram-Positive Bacteria", Proc. Natl. Acad. Sci. USA, 95: 11383-11388, 1988.

D.L. Carlson, et al., "I Kappa B Overexpression in Cardiomyocytes Prevents NF-kappa B Translocation and Provides Cardioprotection in Trauma", Am J. Physiol. Heart Circ. Physiol 284:H804-814, 2003.

G. Chen et al., TNF-Induced Recruitment and Activation of the IKK Complex Require Cdc37 and Hsp9O, Mol Cell 9:401-410, 2002.

G. Chen, et al., "TNF-R1 Signaling: A Beautiful Pathway", Science 296: 1634-1635, 2002.

J. Chesney, et al., "An Essential Role for Macrophage Migration Inhibitory Factor (MIF) in Angiogenesis and the Growth of a Murine Lymphoma", Mol. Med., 5, 181-191, 1999.

O. Court, et al., "Clinical Review: Myocardial Depression Sepsis and Septic Shock", Crit. Care, 6, 500-508, 2002.

Donnelly, S.C., et al., "Regulatory Role for Macrophage Migration Inhibitory Factor in Acute Respiratory Distress Syndrome", Nat. Med., 3, 320-323, 1997.

R. Eickhoff, et al., "Purification and characterization of macrophage migration inhibitory factor as a secretory protein from rat epididymis: evidences for alternative release and transfer to spermatozoa", Mol Med 7: 27-35, 2001.

K. Emmanuilidis, et al., "Differential regulation of systemic IL-18 and IL-12 release during postoperative sepsis: high serum IL-18 as an early predictive indicator of lethal outcome", Shock 18: 301-305, 2002.

H.G. Evans, et al., "Interleukin-1 beta modulates myocardial contraction via dexamethasone sensitive production of nitric oxide", Cardiocasc Res 27: 1486-1490, 1993.

G. Fingerle-Rowson, et al., "Regulation of Macrophage Migration Inhibitory Factor Expression by Glucocorticoids in vivo", Am. J. Pathol., 162, 47-56, 2003.

C.J. Fisher, Jr. et al., "Treatment of septic shock with the tumor necrosis factor receptor:Fc fusion protein", N End J Med 334: 1697-1702, 1996.

C.J. Fisher, Jr., et al., "Influence of an anti-tumor necrosis factor monoclonal antibody on cytokine levels in patients with sepsis", Crit Care Med 21: 318-327, 1993.

(56) References Cited

OTHER PUBLICATIONS

C.J. Fisher, Jr., et al., "Recombinant human interleukin 1 receptor antagonist in the treatment of patients with sepsis syndrome", JAMA 271: 1836-1843, 1994.

C.J. Fisher, Jr., et al., "Initial evaluation of human recombinant interleukin-I receptor antagonist in the treatment of sepsis syndrome: a randomized, open-label, placebo-controlled multicenter trial", Crit Care Med 22: 12-21, 1994.

O. Flieger, et al., "Regulated secretion of macrophage migration inhibitory factor is mediated by a non-classical pathway involving an ABC transporter", FEBS Lett 55 1: 78-86, 2003.

J. Fukuzawa, et al., "Contribution of Macrophage Migration Inhibitory Factor to Extracellular Signal-Regulated Kinase Activation by Oxidative Stress in Cardiomyocytes", J. Biol. Chem., 277, 24889-24895, (2002).

R.J. Fulton, et al., "Advanced multiplexed analysis with the FlowMetrix system" Clin Chem 43: 1749-1756, 1997.

S. Gando, et al., "Macrophage Migration Inhibitory Factor is a Critical Mediator of Systemic Inflammatory Response Syndrome", Intensive Care Med., 27, 1187-1193, 2001.

Garner et al., "Macrophage migration inhibitory factor is a cardiac-derived myocardial depressant factor" Am J. Physiol Heart Circ Physiol 285: H2500-H2509, 2003.

T. Kadokami, et al., "Effects of soluble TNF receptor treatment on lipopolysaccharide-induced myocardial cytokine expression", Am J Physiol Heart Circ Physiol 280: H2281-2291, 2001.

S. Gardella, et al., "The nuclear protein HMGB 1 is secreted by monocytes via a non-classical, vesicle-mediated secretory pathway" EMBO Rep 3: 995-1001, 2002.

B.P. Giroir, et al., "Inhibition of Tumor Necrosis Factor Prevents Myocardial Dysfunction During Burn Shock", Am. J. Physiol., 267, H118-H124, 1994.

S.B. Haudek, et al., "Overexpression of cardiac I-kappaBalpha prevents endotoxin-induced myocardial dysfunction", Am J Physiol Heart Circ Physiol 280: H962-968, 2001.

Haudek, et al., "Differential Regulation of Myocardial NF Kappa B Following Acute or Chronic TNF-Alpha Exposure", J. Mol. Cell Cardiol., 33, 1263-1271, 2001.

D.G. Hesse, "Cytokine appearance in human endotoxemia and primate bacteremia" Surg Gynecol Obstet 166: 147-153, 1988.

J.W. Horton, et al., "Postburn cardiac contractile function and biochemical markers of postburn cardiac injury" J Am Coll Surg 181: 289-298, 1995.

J.W. Horton, et al., "Antioxidant vitamin therapy alters burn trauma-mediated cardiac NF-kappaB activation and cardiomyocyte cytokine secretion", J Trauma 50: 397-406; discussion 407-408, 2001.

J.D. Hudson, et al., "A Proinflammatory Cytokine Inhibits p53 Tumor Suppressor Activity", J. Exp. Med., 190, 1375-1382, 1999.

A. Kamimura, et al., "Intracellular Distribution of Macrophage Migration Inhibitory Factor Predicts the Prognosis of Patients with Adenocarcinoma of the Lung", Cancer, 89: 334-341, 2000.

J.R. Kettman, et al., "Classification and properties of 64 multiplexed microsphere sets", Cytometry 33: 234-243, 1998.

\* cited by examiner

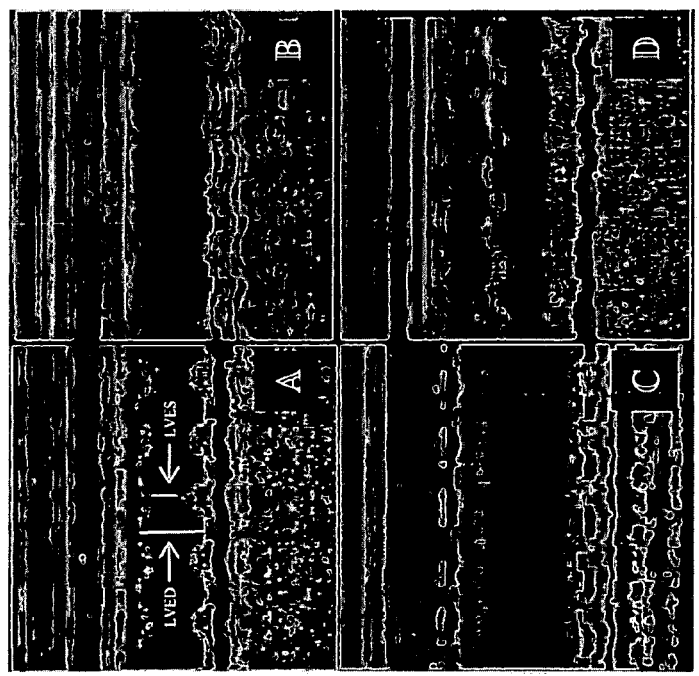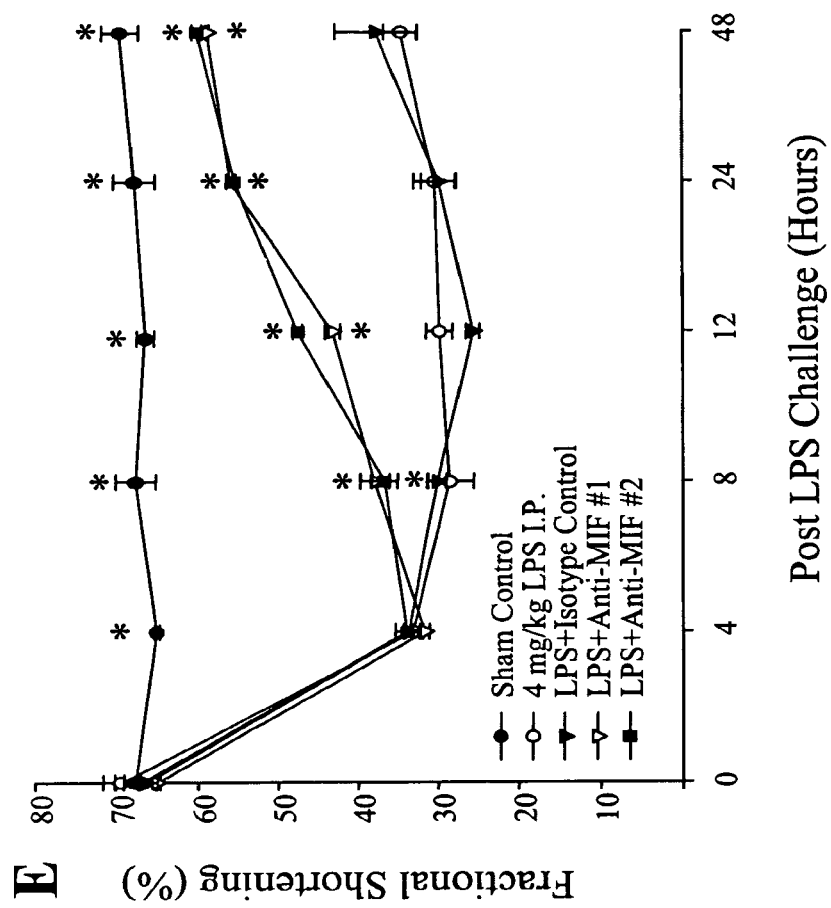
FIG.5

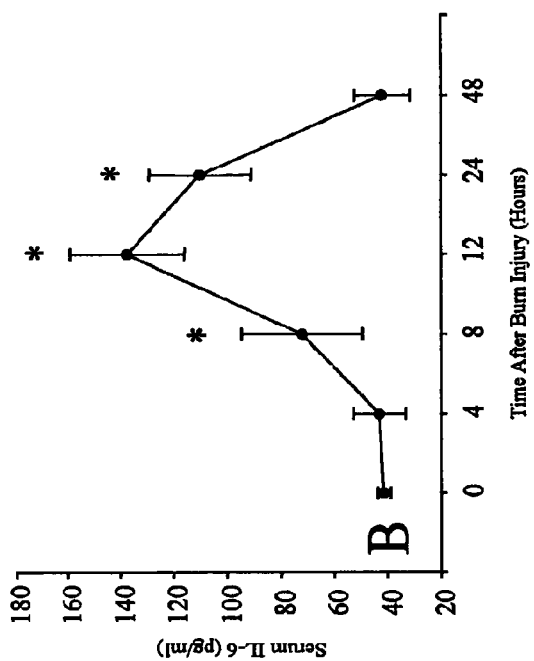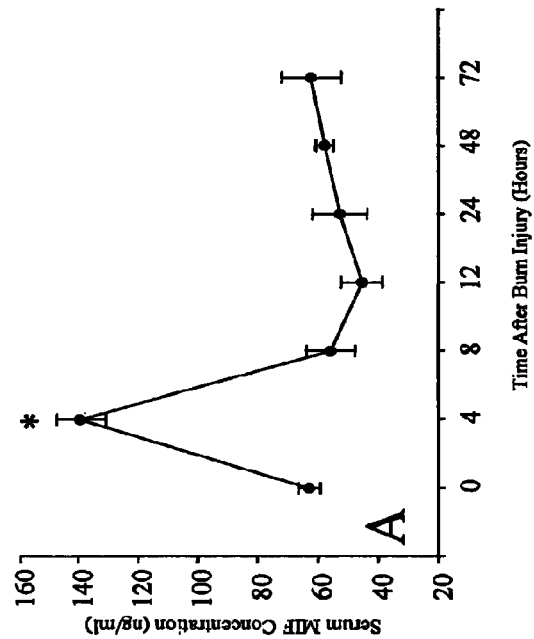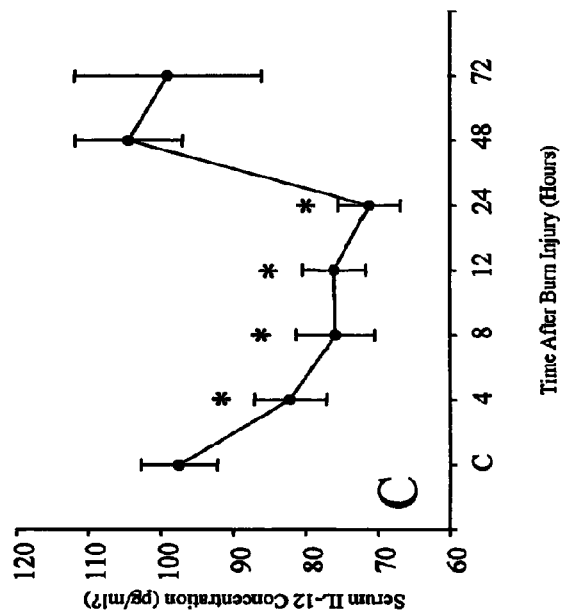
FIG. 9

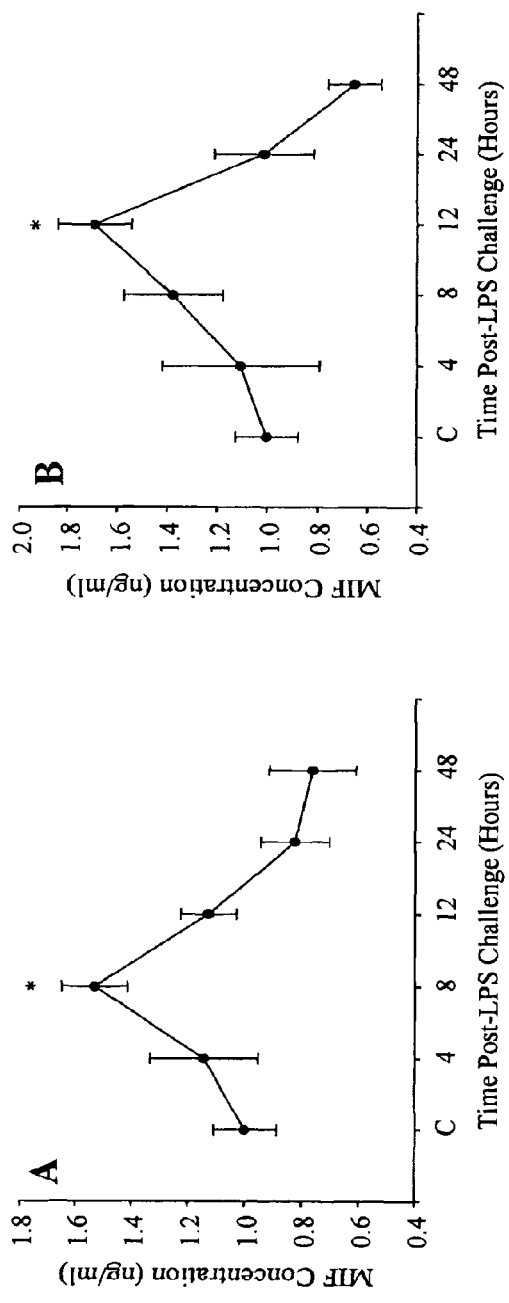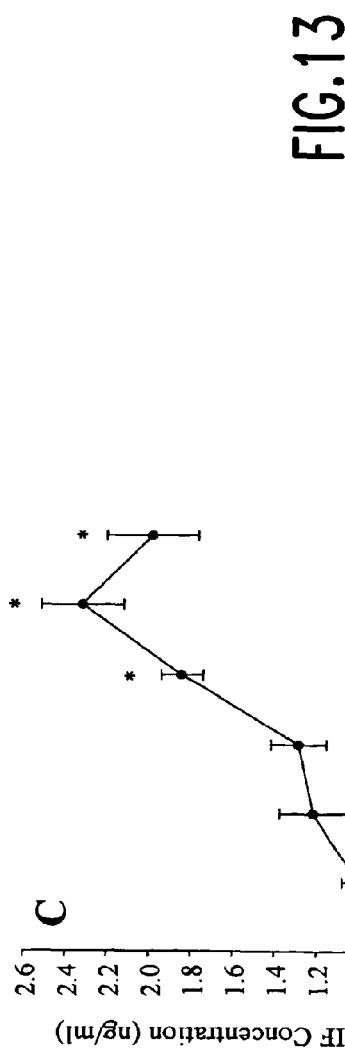
FIG. 13

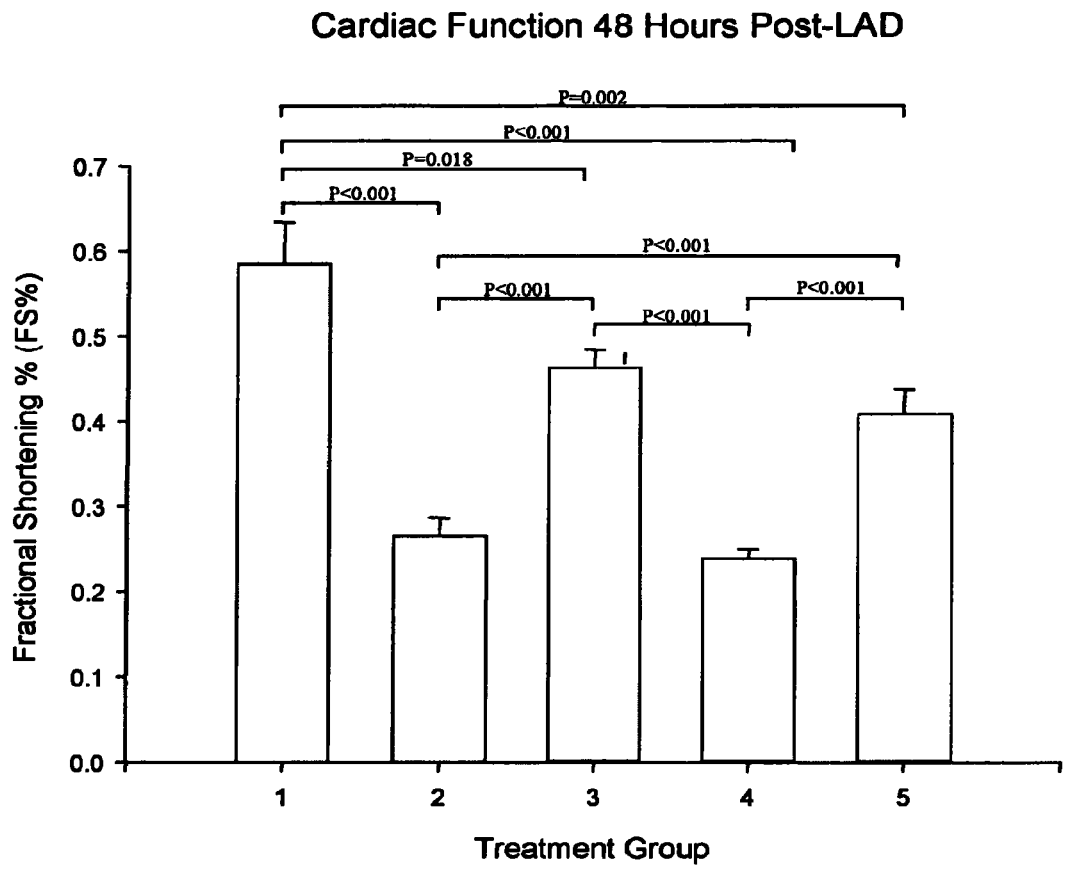

Treatment Groups
Group 1  Control/Normal
Group 2  LAD Only (parallel with Group 3)
Group 3  Pre-Anti-MIF Treatment (90 minutes) + LAD
Group 4  LAD Only (ran in parallel with Group 5)
Group 5  90 Minutes Post LAD Anti-MIF Treatment Statistics: A One Way Anova (Repeated Measures) was initially run to determine that statistical significance was reached. Subsequently, a Tukey test was run between groups to determine significance. Statistical analysis was performed using SigmaStat.

FIG.23

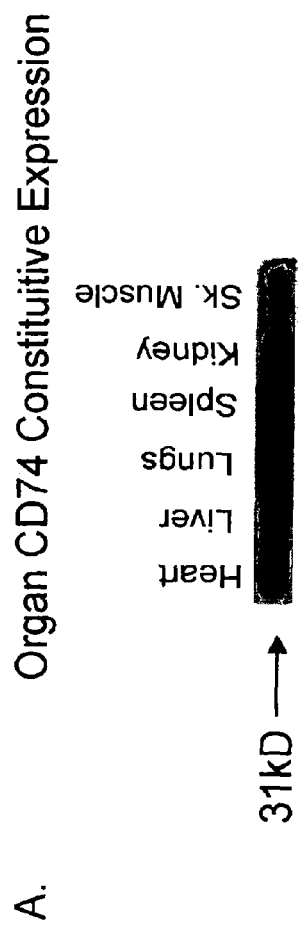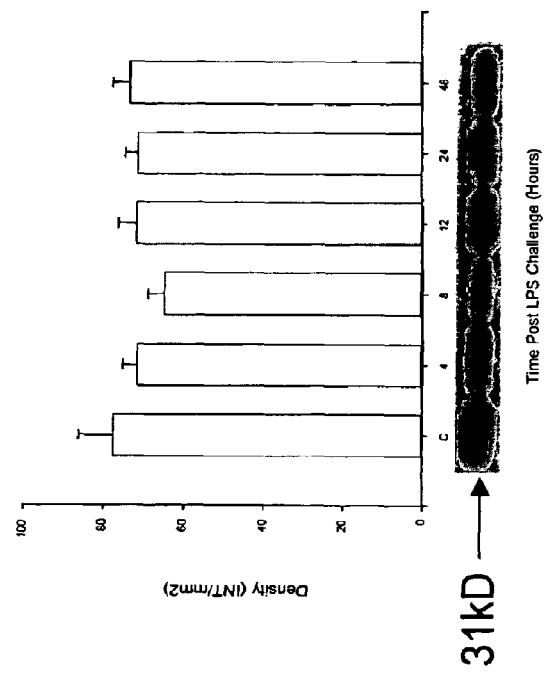
FIG. 26

METHOD OF TREATMENT AND BIOASSAY INVOLVING MACROPHAGE MIGRATION INHIBITORY FACTOR (MIF) AS CARDIAC-DERIVED MYOCARDIAL DEPRESSANT FACTOR

This application is a continuation of U.S. application Ser. No. 10/927,494, filed Aug. 27, 2004, which is based on U.S. Provisional Application Nos. 60/498,659, filed Aug. 29, 2003; 60/547,054, filed Feb. 25, 2004; 60/547,056, filed Feb. 25, 2004; 60/547,057, filed Feb. 25, 2004; 60/547,059, filed Feb. 25, 2004, and 60/556,440, filed Mar. 26, 2004, the entire contents of each of which are hereby incorporated by reference for all purposes.

This invention was made with Government support under Grant Number RO1GM58863 awarded by the National Institutes of Health. The Government may have certain rights in the invention.

BACKGROUND OF THE INVENTION

1. Field of the Invention

The invention generally relates to pathology and physiology in vertebrate species involving cytokines and other cellular signaling mechanisms, and also diagnostic assays involving cytokines and other cellular signaling mechanisms. Other aspects of the invention relate to macrophage migration inhibitory factor (MIF) as a myocardial depressant factor and as a mediator of endotoxin-induced cardiac dysfunction in vivo. Other aspects of the invention relate to mediating and/or inhibiting the production or activity of MIF, and compounds, compositions, methods of treating and preventing cardiac dysfunction, sepsis, burn injury or other conditions related to burns. Other aspects of the invention relate to the MIF release from the heart, liver, and spleen and the role of TNF receptor I/II signaling after LPS challenge. Other aspects of the invention relate to TNF receptor I/II signaling independent release of MIF into the serum. Other aspects of the invention relate to the expression of CD74 on cardiomyocytes and its mediation of cardiac dysfunction.

2. Background of the Technology

Macrophage migration inhibitory factor (MIF) is a pluripotent, pro-inflammatory cytokine whose mechanisms of action have been scrutinized over the past four decades. The current understanding in the art relating to MIF includes studies directed to its crystallization as a trimer, its physiologically relevant oligomerization state; its putative membrane receptor(s); and the physiologic relevance of its intracellular enzymatic activity as a tautomerase and oxidoreductase.

Many studies have demonstrated that MIF has an important role in diseases as diverse as rheumatoid arthritis (M. Leech, et al., "Macrophage Migration Inhibitory Factor in Rheumatoid Arthritis: Evidence of Proinflammatory Function and Regulation by Glucocorticoids", Arthritis Rheum, 42, 1601-1608 (1999), M. Leech, et al., "Involvement of Macrophage Migration Inhibitory Factor in the Evolution of Rat Adjuvant Arthritis", Arthritis Rheum., 41, 910-917 (1998), A. Mikulowska, et al., "Macrophage Migration Inhibitory Factor is Involved in the Pathogenesis of Collagen Type 11-Induced Arthritis in Mice", J. Immunol., 158, 5514-5517 (1997)), delayed-type hypersensitivity (J. Bernhagen, et al., "An Essential Role for Macrophage Migration Inhibitory Factor in the Tuberculin Delayed-Type Hypersensitivity Reaction", J. Exp. Med., 183, 277-282 (1996), H.Y. Lan, et al., "De Novo Renal Expression of Macrophage Migration Inhibitory Factor During the Development of Rat Crescentic Glomerulonephritis", Am. J. Pathol., 149, 1119-1127 (1996), H.Y. Lan, et al., "Macrophage Migration Inhibitory Factor Expression in Human Renal Allograft Rejection", Transplantation, 66, 1465-1471 (1998), H.Y. Lan, et al., "TNF-Alpha Up-Regulates Renal MIF Expression in Rat Crescentic Glomerulonephritis", Mol. Med., 3, 136-144 (1997), T. Shimizu, et al., "Increased production of Macrophage Migration Inhibitory Factor by PBMCs of Atopic Dermatitis", J. Allergy Clin. Immunol., 104, 659-669 (1999)), inflammatory lung disease (S. C. Donnelly, et al., "Regulatory Role for Macrophage Migration Inhibitory Factor in Acute Respiratory Distress Syndrome", Nat. Med., 3, 320-323 (1997), H. Makita, et al., "Effect of Anti-Macrophage Migration Inhibitory Factor Antibody on Lipopolysaccharide-Induced Pulmonary Neutrophil Accumulation", Am. J. Respir. Crit. Care Med., 158, 573-579 (1998), A. G. Rossi, et al., "Human Circulating Eosinophils Secrete Macrophage Migration Inhibitory Factor (MIF). Potential Role in Asthma", J. Clin. Invest., 101, 2869-2874 (1998)), cancer (J. Chesney, et al., "An Essential Role for Macrophage Migration Inhibitory Factor (MIF) in Angiogenesis and Growth of a Murine Lymphoma", Mol. Med., 5, 181-191 (1999), M. T. del Vecchio, et al., "Macrophage Migration Inhibitory Factor in Prostatic Adenocarcinoma: Correlation with Tumor Grading and Combination Endocrine Treatment-Related Changes", Prostate, 45, 51-57 (2000), J. D. Hudson, et al., "A1 Proinflammatory Cytokine Inhibits p53 Tumor Suppressor Activity", J. Exp. Med., 190, 1375-1382 (1990), A. Kamimura, et al., "Intracellular Distribution of Macrophage Migration Inhibitory Factor Predicts the Prognosis of Patients with Adenocarcinoma of the Lung", Cancer, 89, 334-341 (2000), K. Meyer-Siegler, et al., "Increased Stability of Macrophage Migration Inhibitory Factor (MIF) in DU-145 Prostate Cancer Cells", J. Interferon Cytokine Res., 20, 769-778 (2000), T. Shimizu, et al., "High Expression of Macrophage Migration Inhibitory Factor in Human Melanoma Cells and Its Role in Tumor Cell Growth and Angiogenesis", Biochem. Biophys. Res. Commun., 264, 751-758 (1999), Takahashi, et al., "Involvement of Macrophage Migration Inhibitory Factor (MIF) in the Mechanism of Tumor Cell Growth", Mol. Med., 4, 707-714 (1998)), myocardial infarction (M. Takashashi, et al., "Elevation of Plasma Levels of Macrophage Migration Inhibitory Factor in Patients with Acute Myocardial Infarction", Am. J. Cardiol., 89, 248-249 (2002), M. Takahashi, et al., "Macrophage Migration Inhibitory Factor as a Redox-Sensitive Cytokine in Cardiac Myocytes", Cardiovasc Res., 52, 438-445 (2001), C. M. Yu, et al., "Elevation of Plasma Level of Macrophage Migration Inhibitory Factor in Patients with Acute Myocardial Infarction", Am. J. Cardiol., 88, 774-777 (2001)), and septic shock (J. Berhnagen, et al., "MIF is a Pituitary-Derived Cytokine that Potentiates Lethal Endotoxaemia", Nature, 365, 756-759 (1993), M. Bozza, et al., "Targeted Disruption of Migration Inhibitory Factor Gene Reveals Its Critical Role in Sepsis", J. Exp. Med. 189, 341-346 (1999), T. Calandra, et al., "MIF as a Glucocorticoid-Induced Modulator of Cytokine Production", Nature, 377, 68-71 (1995), T. Calandra, et al., "Protection from Septic Shock by Neutralization of Macrophage Migration Inhibitory Factor", Nat. Med., 6, 164-170 (2000), T. Calandra, et al., "Macrophage Migration Inhibitory Factor is a Critical Mediator of the Activation of Immune Cells by Exotoxins of Gram-Positive Bacteria", Proc. Natl. Acad. Sci. USA, 95, 11383-11388 (1998)). There is some evidence that monoclonal or polyclonal anti-MIF antibodies may affect the pathology of sepsis, but their role has not been exhaustively characterized in humans. However, during septic shock, MIF is increased in the plasma of animals and humans, and the blockade of MIF activity by monoclonal or polyclonal antibodies results in a marked improvement in the survival of animals with experimentally induced sepsis (M. Bozza, et al., "Targeted Disruption of Migration Inhibitory Factor Gene Reveals Its Critical Role in Sepsis", J. Exp. Med. 189, 341-346 (1999), T. Calandra, et al., "Protection from Septic Shock by Neutralization of Macrophage Migration Inhibitory Factor", Nat. Med., 6, 164-170 (2000)).

The blockade of MIF activity has been demonstrated with a number of inhibitors. Blockade of MIF enzymatic activity has been demonstrated with diverse chemical compounds as shown in U.S. patent application Ser. No. 10/226,299, filed Aug. 23, 2002, now pending. See also, for instance, U.S. Pat. No. 6,492,428. Antibodies have also been used to blockade MIF activity as shown in U.S. Pat. No. 6,030,615. MIF expression can also be inhibited using antisense technology as disclosed in U.S. patent application Ser. No. 08/738,947, filed Oct. 24, 1996, now pending, or U.S. Pat. No. 6,268,151 which further demonstrates pharmaceutical formulations that can be used with all the above-mentioned MIF inhibitors.

Lipopolysaccharide (LPS) depresses intrinsic myocardial contractility and is thought to be important in myocardial dysfunction that occurs in sepsis and septic shock (A. M. Lefer, "Mechanisms of cardiodepression in endotoxin shock", Circ Shock Suppl 1:1-8 (1979), J. E. Parrillo, et al., "A circulating myocardial depressant substance in humans with septic shock. Septic shock patients with a reduced ejection fraction have a circulating factor that depresses in vitro myocartdial cell performance", J. Clin. Invest. 76:1539-1553 (1985), J. M. Reilly, et al., "A circulating myocardial depressant substance is associated with cardiac dysfunction and peripheral hypoperfusion (lactic acidemia) in patients with septic shock", Chest. 95:1072-1080 (1989)). Many pro-inflammatory cytokines are released after an LPS challenge and have been shown to directly mediate the observed cardiac dysfunction including TNF-α, IL-1β, IL-6, IL-18, NO, and macrophage migration inhibitory factor (MIF) (O. Court, et al., "Clinical review: Myocardial depression sepsis and septic shock", Crit. Care 6:500-508 (2002), L. B. Gamer, et al., "Macrophage migration inhibitory factor is a caridac-derived myocardial depressant factor", Am. J. Physiol Heart Circ Physiol, 285:H2500-2509 (2003), S. Krishnagopalan, et al., "Myocardial dysfunction in the patient with sepsis", Curr. Opin. Crit. Care 8:376-388 (2002)). We recently described macrophage migration inhibitory factor (MIF) as a cardiac derived myocardial depressant factor in a model of sublethal endotoxin challenge (endotoxicosis) (L. B. Garner, et al., "Macrophage migration inhibitory factor is a cardiac-derived myocardial depressant factor", Am. J. Physiol Heart Circ. Physiol 285:H2500-2509 (2003)). An LPS challenge induced the constitutive presence of the proinflammatory cytokine MIF to be released maximally by 12 hours. The release of MIF in this model paralleled the cardiac dysfunction that MIF was shown to mediate which was delayed after LPS challenge. Neutralization of MIF by anti-MIF antibodies resulted in significant protection starting at 8 hours and was completed ablated by 48 hours ((L. B. Garner, et al., "Macrophage migration inhibitory factor is a cardiac-derived myocardial depressant factor", Am. J. Physiol Heart Circ. Physiol 285: H2500-2509 (2003))). MIF is unique among the aforementioned cytokines in its delayed release and ability to block downstream mediators.

Investigators have previously reported a temporal discordance between the TNF-α levels in the myocardium and the contractile dysfunction that occurred during endotoxemia (X. Meng, et al., "TNF-alpha and myocardial depression in endoxtoxemic rats: temporal discordance of an obligatory relationhship", Am. J. Physiol 275:R502-508 (1998)). That is, cardiac dysfunction did not occur until TNF-α levels had returned to baseline suggesting that TNF-α is an important sentinel signal for other cardiac depressants which more directly conspire to cause dysfunction in sepsis. The significance of these early cytokines is unknown, however therapeutic strategies against early mediators of septic shock such as anti-IL-1β and anti-TNF-α modalities have been tested in human trials, no benefits have been observed likely due to their early appearance in the disease process (C. J. Fisher, et al., "Recombinant human inerleukin 1 receptor antagonist in the treatment of patients with sepsis syndrome. Results from a randomized, double-blind, placebo-controlled trial", Phase III rhIL-1ra Sepsis Syndromve Study Group, Jama, 271: 1836-1843 (1994), C. J. Fisher, et al., "Initial evaluation of human recombinant interleukin-1 receptor antagonist in the treatment of sepsis syndrome: a randomized, open-label, placebo-controlled multicenter trial", The IL-1RA Sepsis Syndrome Study Group, Crit. Care Med., 22:12-21 (1994), C. Natanson, et al., "Selected treatment strategies for septic shock based on proposed mechanisms of pathogenesis", Ann. Intern. Med., 120:771-783 (1994), K. Reinhart, et al., "Anti-tumor necrosis factor therapy in sepsis:update on clinical trials and lessons learned", Crit. Care Med., 29:S121-125 (2001)).

Macrophage migration inhibitory factor (MIF) is involved in the pathogenesis of several diseases, including sepsis. MIF opposes the anti-inflammatory effects of glucocorticoids, and also significantly alters tissue metabolism. Although MIF appears to be ubiquitously expressed, there are currently no publications indicating whether MIF is expressed in the myocardium in vivo, or whether release of MIF from the myocardium or other tissues during sepsis could adversely affect cardiac performance.

Cardiac dysfunction during sepsis (O. Court, et al., "Clinical review: Myocardial depression sepsis and septic shock", Crit. Care, 6:500-508 (2002), S. Krishnagopalan, et al., "Macrophage Dysfunction in the Patient with Sepsis", Curr. Opin. Crit. Care, 8, 376-388 (2002)) is associated with poor outcome in both humans (P. Ammann, et al., "Elevation of Troponin I in Sepsis and Septic Shock", Intensive Care Med., 27, 965-969 (2001), C. N. Sessler, et al., "New Concepts in Sepsis", Curr. Opin. Crit. Care, 8, 465-472 (2002)) and animal models (M. Bozza, et al., "Targeted Disruption of Migration Inhibitory Factor Gene Reveals Its Critical Role in Sepsis", J. Exp. Med., 189, 341-346 (1999), T. Calandra, et al., "Protection from Septic Shock by Neutralization of Macrophage Migration Inhibitory Factor", Nat. Med., 6, 164-170 (2000)). It has been previously demonstrated that sepsis or burn associated cardiac dysfunction is primarily due to circulating myocardial depressant factors, including TNF-α (B. P. Giroir, et al., "Inhibition of Tumor Necrosis Factor Prevents Myocardial Dysfunction During Burn Shock", Am. J. Physiol., 267, H118-H124 (1994), Haudek, et al., "Differential Regulation of Myocardial NF Kappa B Following Acute or Chronic TNF-Alpha Exposure", J. Mol. Cell. Cardiol., 33, 1263-1271 (2001), A. Kumar, et al., "Tumor Necrosis Factor Alpha and Interleukin 1 Beta are Responsible for in vitro Myocardial Cell Depression Induced by Human Septic Shock Serum", J. Exp. Med., 183, 949-958 (1996)). However, since TNF-α is a sentinel, rapid response cytokine, and is gone from the circulation days or weeks before the resolution of myocardial dysfunction, there remains a need for finding whether additional myocardial depressant proteins might exist.

Studies utilizing live bacteria, either by direct injection of E coli i.p. or by cecal ligation and puncture (CLP), have previously demonstrated that MIF plasma and/or peritoneal fluid levels increase several hours post challenge, and that antibodies against MIF protected the mice from lethal bacterial peritonitis (T. Calandra, et al., "Protection from septic shock by neutralization of macrophage migration inhibitory factor", Nat. Med., 6, 164-170 (2000)). Moreover, mice were protected when the antibodies were given as late as 8 h after the onset of infection (T. Calandra, et al., "Protection from septic shock by neutralization of macrophage migration inhibitory factor", Nat. Med., 6, 164-170 (2000)).

MIF has a number of properties that make it unique among cytokines. MIF is released preformed from numerous cell types including lymphocytes, macrophages, and the anterior pituitary (J. Bernhagen, et al., "Regulation of the Immune Response by Macrophage Migration Inhibitory Factor: Biological and Structural Features", J. Mol. Med., 76, 151-161 (1998), T. Calandra, et al., "Macrophage Migration Inhibitory Factor (MIF): A Glucocorticoid Counter-Regulator Within the Immune System", Crit. Rev. Immunol., 17, 77-88 (1997), S. C. Donnelly, et al., "Macrophage Migration Inhibitory Factor: A Regulator of Glucocorticoid Activity with a Critical Role in Inflammatory Disease", Mol. Med. Today, 3, 502-507 (1997), R. A. Mitchell, et al., "Tumor Growth-Promoting Properties of Macrophage Migration Inhibitory Factor (MIF)", Semin. Cancer Biol., 10, 359-366 (2000)). However, the list of sources of MIF continues to grow and includes other tissues such as lung, liver, adrenal, spleen, kidney, skin, muscle, thymus, skin, and testes (M. Bacher, et al., "Migration Inhibitory Factor Expression in Experimentally Induced Endotoxemia", Am. J. Pathol., 150, 235-246 (1997), G. Fingerle-Rowson, et al., "Regulation of Macrophage Migration Inhibitory Factor Expression by Glucocorticoids in vivo", Am. J. Pathol, 162, 47-56 (2003)). MIF has at least 2 catalytic activities that are distinct: tautomerase and oxidoreductase activity. To this end, pharmacological inhibitors of MIF tautomerase activity have been developed for the treatment of MIF-related diseases such as sepsis, acute respiratory distress syndrome (ARDS), asthma, atopic dermatitis, rheumatoid arthritis, nephropathy, and cancer (A. Dios, et al., "Inhibition of MIF Bioactivity by Rational Design of Pharmacological Inhibitors of MIF Tautomerase Activity", J. Med. Chem., 45, 2410-2416 (2002), M. Orita, et al., "Macrophage Migration Inhibitory Factor and the Discovery of Tautomerase Inhibitors", Curr. Pharm. Des., 8, 1297-1317 (2002)). These diseases have shown benefit from anti-MIF antibodies.

Several investigations indicate that MIF may exert effects by both direct and indirect mechanisms. Previous studies have provided evidence that MIF promotes the release and pharmacodynamic effects of other pro-inflammatory cytokines. Macrophages expressing anti-sense MIF cDNA (leading to less endogenous MIF) secrete/express significantly less TNF-α, IL-6, and NO, while NF-κB activity is decreased in response to LPS (44). Therefore, it appears that MIF may directly interact with the LPS signaling pathway (H. Lue, et al., "Macrophage Migration Inhibitory Factor (MIF): Mechanisms of Action and Role in Disease", Microbes Infect., 4, 449-460 (2002)). Moreover, MIF knockout (MIFKO) mice, as demonstrated in U.S. patent application Ser. No. 10/322, 685 filed Dec. 19, 2002, which are resistant to lethal doses of LPS, have lower circulating plasma levels of TNF-α compared to wild-type mice at baseline. Upon LPS challenge, they demonstrate diminished circulating TNF-α concentrations, increased nitric oxide (NO) concentrations, and unchanged IL-6 and IL-12 concentrations (M. Bozza, et al., "Targeted Disruption of Migration Inhibitory Factor Gene Reveals Its Critical Role in Sepsis", J. Exp. Med. 189, 341-346 (1999)). While MIF appears to promote pro-inflammatory cytokines, the effects of MIF have been shown to act in a TNF-α-independent manner. When CLP was performed in TNF-α knock out mice, a 60% survival rate was seen in mice administered anti-MIF antibodies compared to a 0% survival rate in wild-type mice (T. Calandra, et al., "Protection from Septic Shock by Neutralization of Macrophage Migration Inhibitory Factor", Nat. Med., 6, 164-170 (2000)).

In relation to cardiac dysfunction not related to sepsis, elevated serum MIF concentrations have also been described in patients following acute myocardial infarction (M. Takahashi, et al., "Elevation of Plasma Levels of Macrophage Migration Inhibitory Factor in Patients with Acute Myocardial Infarction", Am. J. Cardiol., 89, 248-249 (2002), M. Takahashi, et al., "Macrophage Migration Inhibitory Factor as a Redox-Sensitive Cytokine in Cardiac Myocytes", Cardiovasc Res., 52, 438-445 (2001), C. M. Yu, et al., "Elevation of Plasma Level of Macrophage Migration Inhibitory Factor in Patients with Acute Myocardial Infarction", Am. J. Cardiol., 88, 774-777 (2001)), with heretofore unknown physiologic relevance. Similarly, cultured cardiac myocytes have been noted to release MIF in response to hypoxia and hydrogen peroxide (free radical initiator) but not angiotensin II, endothelin-1, IL-1β, or TNF-α (J. Fukuzawa, et al., "Contribution of Macrophage Inhibitory Factor to Extracellular Signal-Regulated Kinase Activation by Oxidative Stress in Cardiomyocytes", J. Biol. Chem., 277, 24889-24895, M. Takahashi, et al., "Macrophage Migration Inhibitory Factor as a Redox-Sensitive Cytokine in Cardiac Myocytes", Cardiovasc Res., 52, 438-445 (2001)). There are many clinical scenarios which could potentially trigger myocardial MIF release, thereby adversely affecting cardiac function. Cardiac dysfunction can be manifest through any irregular condition in the cardiac myocytes and cardiac tissue. Such dysfunctions include, but are not limited to, mycarditis, endocarditis, pericarditis, rheumatic heart disease, myocardial infarction, arrythmia, fibrillation, cardiogenic shock, ischemia, hypertrophy, cardiomyopathy, angina, heart murmur or palpitation, heart attack or failure, and any of the symptoms or defects associated with congenital heart diseases generally.

Macrophage migration inhibitory factor is a expressed in many organs including the heart and has been linked with a delayed cardiac dysfunction in a murine model of endotoxicosis (Garner, et al., "Macrophage Migration Inhibitory Factor is A Cardiac-Derived Myocardial Depressant Factor", Am. J. Physiol. Heart Circ. Physiol, 258, H2500-H2509 (2003)).

Burn injury results in cardiac injury and contractile dysfunction involving decreased cardiac output, shock, and left ventricular failure (J. T. Murphy, et al., "Evaluation of Troponin-I as An Indicator of Cardiac Dysfunction After Thermal Injury, 45, 700-704, (1998), E. M. Reynolds, et al., "Left Ventricular Failure Complicating Severe Pediatric Burn Injuries", J. Pediatr. Surg. 30, 264-269; discussion 269-270 (1995), W. C. Shoemaker, et al., "Burn Pathophysiology In Man. I. Sequential Hemodynamic Alterations, J. Surg. Res., 14, 64-73 (1973), R. R. Wolfe, et al., "Review: Acute Versus Chronic Response to Burn Injury", Circ. Shock, 8, 105-115 (1981)). These contractile deficits have been reported to appear as early as 2 hours after burn injury (J. W. Horton, et al., "Postburn Cardiac Contractile Function and Biochemical Markers of Postburn Cardiac Injury", J. Am. Coll. Surg., 181, 289-298 (1995)). Several recent studies have elucidated the early molecular events which involve an endotoxin signaling pathway including the toll-like receptor 4 (Tlr-4), IRAK, and NF-kB in response to gut derived factors (D. L. Carlson, et al., "I Kappa B Overexpression in Cardiomyocytes Prevents NF-Kappa B Translocation and Provides Cardioprotection in Trauma", Am. J. Physiol. Heart Circ. Physiol, 284, H804-814

(2003), J. T. Sambol, et al., "Burn-Induced Impairment of Cardiac Contractile Function is Due to Gut-Derived Factors Transported in Mesenteric Lymph", Shock, 18, 272-276 (2002), J. A. Thomas, et al., "IRAK Contributes to Burn-Triggered Myocardial Contractile Dysfunction", Am. J. Physiol. Heart Circ. Physiol., 283, H829-836 (2002), J. A. Thomas, et al., "TLR4 Inactivation and rBPI(21) Block Burn-Induced Myocardial Contractile Dysfunction", Am. J. Physiol. Heart Circ. Physiol., 283, H1645-1655 (2002)).

While endotoxin signaling through the Tlr-4 receptor represents the initial pathway of burn injury associated cardiac dysfunction, other investigators have demonstrated that early downstream mediators include TNF-α, IL-1β, and IL-6 (H. Lue, et al., "Macrophage Migration Inhibitory Factor (MIF): Mechanisms of Action and Role in Disease", Microbes Infect., 4, 449-460 (2002)). Experimentally, when TNF-α is blocked, burn injury associated cardiac dysfunction is decreased, emphasizing its importance as a key regulator of dysfunction (B. P. Giroir, et al., "Inhibition of Tumor Necrosis Factor Prevents Myocardial Dysfunctional During Burn Shock", Am. J. Physiol., 267, H118-124 (1994)). When therapeutic strategies against early mediators of septic shock such as anti-IL-1β and anti-TNF-α modalities have been tested in human trials, no benefits have been observed likely due to their early appearance in the disease process (C. J. Fisher Jr., et al., "Recombinant Human Interleukin 1 Receptor Antagonist in the Treatment of patients with Sepsis Syndrome, Results from a Randomized, Double-Blind, Placebo-Controlled Trial", Phase III rhIL-1ra Sepsis Syndrome Study Group, Jama. 271, 1836-1843 (1994), C. J. Fisher, et al., "Initial Evaluation of Human Recombinant Interleukin-1 Receptor Antagonist in the Treatment of Sepsis Syndrome: A Randomized, Open-Label, Placebo-Controlled Multicenter Trial", The IL-1RA Sepsis Syndrome Study Group, Crit. Care Med., 22, 12-21 (1994), C. Natanson, et al., "Selected Treatment Strategies for Septic Shock Based on Proposed Mechanisms of Pathogenesis", Ann. Intern. Med., 120, 771-783 (1994), K. Reinhart, et al., "Anti-Tumor Necrosis Factor Thereapy in Sepsis: Update on Clinical Trails and Lessons Learned", Crit. Care Med., 29, S121-125 (2001)).

Recently, the cytokine known as macrophage migration inhibitory factor (MIF) has been shown to play a key role in sepsis mortality (H. Lue, et al., "Macrophage Migration Inhibitory Factor (MIF): Mechanisms of Action and Role in Disease", Micorbes Infect., 4, 449-460 (2002)). In fact, anti-MIF therapy has been shown to improve survival significantly in lethal models of sepsis (cecal ligation and puncture), even when given up to 8 hours after the insult (T. Calandra, et al., "Protection From Septic Shock Byneutralization of Macrophage Migration Inhibitory Factor", Nat. Med., 6, 164-170 (2000)). Moreover, MIF has been shown to play a key role in ARDS (K. N. Lai, et al., "Role For Macrophage Migration Inhibitory Factor in Acute Respiratory Distress Syndrome", J. Pathol., 199, 496-508 (2003)), a common complication of burn injury (M. Bhatia, et al., "Role of Inflammatory Mediators in the Pathophysiology of Acute Respiratory Distress Syndrome", J. Pathol., 202, 145-156 (2004)). The purpose of this study was then to identify and characterize MIF as a useful therapeutic target of burn injury associated cardiac morbidity using a well defined murine model of burn injury (Garner, et al., "Macrophage Migration Inhibitory Factor is a Cardiac-Derived Myocardial Depressant Factor", Am. J. Physiol. Heart Circ. Physiol., 285, H2500-2509 (2003)).

Accordingly, there remains a need for therapies for cardiodepression, cardiodysfunction, burn associated morbidities and cardioprotection in which no therapy is currently available.

U.S. Pat. No. 6,030,615 relates to methods and compositions for treating a disease caused by cytokine-mediated toxicity.

U.S. Pat. No. 6,420,188 relates to methods and compositions for antagonizing MIF activity and methods of treating various diseases based on this activity.

U.S. Pat. No. 6,599,938 relates to methods and compositions for antagonizing MIF activity and methods of treating various diseases based on this activity.

U.S. Pat. No. 6,645,493 relates to compositions and methods for inhibiting the release and/or biological activity of MIF.

SUMMARY OF THE INVENTION

One embodiment of the present invention relates to a pharmaceutical composition effective for at least one selected from the group including treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, and a combination thereof, which includes:
an effective amount of at least one anti-MIF antibody; and
at least one pharmaceutically acceptable carrier.

Another embodiment of the present invention relates to a pharmaceutical composition effective for at least one selected from the group including treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, and a combination thereof, which includes:
an effective amount of at least one anti-CD74 antibody, and
an effective amount of at least one pharmaceutically acceptable carrier.

Another embodiment of the present invention relates to a pharmaceutical composition effective for at least one selected from the group including treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, and a combination thereof, which includes:
an effective amount of at least one anti-TNFR antibody;
an effective amount of at least one anti-MIF antibody; and
at least one pharmaceutically acceptable carrier.

Another embodiment of the present invention relates to a method for treating and/or preventing cardiac dysfunction in a subject, the method including:
administering to the subject an effective amount of at least one anti-MIF antibody.

Another embodiment of the present invention relates to a method for treating and/or preventing burn injury-associated cardiac dysfunction in a subject, the method including:
administering to the subject an effective amount of at least one anti-MIF antibody.

Another embodiment of the present invention relates to a method for treating and/or preventing cardiac dysfunction in a subject, the method including:
administering to the subject an effective amount of at least one anti-CD74 antibody.

Another embodiment of the present invention relates to a method for improving cardiac function in a subject following acute myocardial infarction, the method including:
administering to the subject an effective amount of at least one anti-MIF antibody.

Another embodiment of the present invention relates to a method for identifying an MIF inhibitor, the method including:
exposing at least one myocyte to at least one MIF;
determining at least one MIF-related myocyte activity;
exposing the myocyte to said MIF and at least one candidate agent;
determining the MIF-related myocyte activity in the presence of the candidate agent; and
determining whether the candidate agent affects the MIF-related myocyte activity.

Another embodiment of the present invention relates to a method for treating and/or preventing cardiac dysfunction in a subject following acute myocardial infarction, the method including:
administering to the subject an effective amount of at least one anti-TNFR antibody and an effective amount of at least one anti-MIF antibody.

Another embodiment of the present invention relates to a method for treating and/or preventing cardiac dysfunction in a subject, the method including:
administering to the subject an effective amount of at least one anti-MIF antibody.

Another embodiment of the present invention relates to a method for treating and/or preventing burn injury-associated cardiac dysfunction in a subject, the method including:
administering to the subject an effective amount of a composition which includes at least one anti-MIF antibody and at least one pharmaceutically acceptable carrier.

Another embodiment of the present invention relates to a method for treating and/or preventing cardiac dysfunction in a subject, the method including:
administering to the subject an effective amount of a composition which includes at least one anti-CD74 antibody and at least one pharmaceutically acceptable carrier.

Another embodiment of the present invention relates to a method for improving cardiac function in a subject following acute myocardial infarction, the method including:
administering to the subject an effective amount of a composition which includes at least one anti-MIF antibody and at least one pharmaceutically acceptable carrier.

Another embodiment of the present invention relates to a method for treating and/or preventing cardiac dysfunction in a subject following acute myocardial infarction, the method including:
administering to the subject an effective amount of a composition which includes at least one anti-TNFR antibody, at least one anti-MIF antibody, and at least one pharmaceutically acceptable carrier.

Another embodiment of the invention relates to a method for at least one selected from the group including treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, and a combination thereof, which includes administering to said subject an effective amount of at least one selected from the group including a small molecule MIF inhibitor, salt thereof, prodrug thereof, and a combination thereof.

Another embodiment of the invention relates to a method for at least one selected from the group including treating or preventing cardiac dysfunction in a subject in need thereof, treating or preventing irregularity in myocardial activity in a subject in need thereof, treating or preventing depression in myocardial activity in a subject in need thereof, treating or preventing burn-injury associated cardiac dysfunction in a subject in need thereof, treating or preventing cardiac dysfunction following acute myocardial infarction in a subject in need thereof, treating or preventing cardiodepression in a subject in need thereof, and a combination thereof, which includes administering to a subject in need thereof an effective amount of at least one anti-TNFR antibody; and
optionally, at least one pharmaceutically acceptable carrier.

DESCRIPTION OF THE FIGURES

The foregoing description will be better understood when read in conjunction with the appended drawings. For the purpose of illustrating the invention, there is shown in the drawings an embodiment which is presently preferred, it being understood, however, that this invention is not limited to the precise arrangements and instrumentalities shown.

FIG. 5: Echocardiographic assessment of the effects of LPS and LPS plus anti-MIF antibody administration on cardiac function. Representative M-mode echocardiograms in wild-type mice at baseline and 8 h after LPS administration, A and B, respectively. C and D show, respectively, representative echocardiograms in LPS plus anti-MIF treated mice at 8 and 48 h. A significant protection in cardiac function (FS %) is observed in LPS challenged mice when anti-MIF antibodies are given pre-treatment (E). Data represents the average of 9 cardiac cycles from 3 mice monitored at multiple time points. *p<0.05.

FIG. 9: Graphical representations of concentration change of three different cytokines over time following thermal trauma. FIG. 9-S*erum* concentrations of MIF (ng/ml), IL-12 (pg/ml), and IL-6 (pg/ml) following burn injury (A-C, respectively). Data are expressed as the mean±SE of six C57BL/6J mice as determined by ELISA and were statistically analyzed using a One Way-ANOVA with a multiple comparison procedure employing the Bonferroni method to determine significance between groups (*p<0.05 compared to baseline).

FIG. 13: Serum MIF concentration (fold increase from baseline) following a 4 mg/kg endotoxin challenge in: (A) wild type mice, (B) TNFR−/− mice, and (C) wild type mice pre-treated (60 minutes) with Enbrel®. Data are expressed a fraction of the baseline levels of MIF (mean +/−standard error) of: (A) 6 C57BL/6J mice, (B) 6 TNFR−/− mice, and (C) 3 C57BL/6J (C) pre-treated with Enbrel®. Serum levels were determined by ELISA and were statistically analyzed using a One Way-ANOVA with a multiple comparison procedure employing the Bonferroni method to determine significance between groups (*p<0.05 compared to baseline).

FIG. 23: Presents cardiac function data 48 hours post-LAD for several treatment groups.

FIG. 26: Shows the organ CD74 constitutive expression and heart CD74 post-LPS challenge expression.

DETAILED DESCRIPTION OF THE INVENTION

Figure 1:
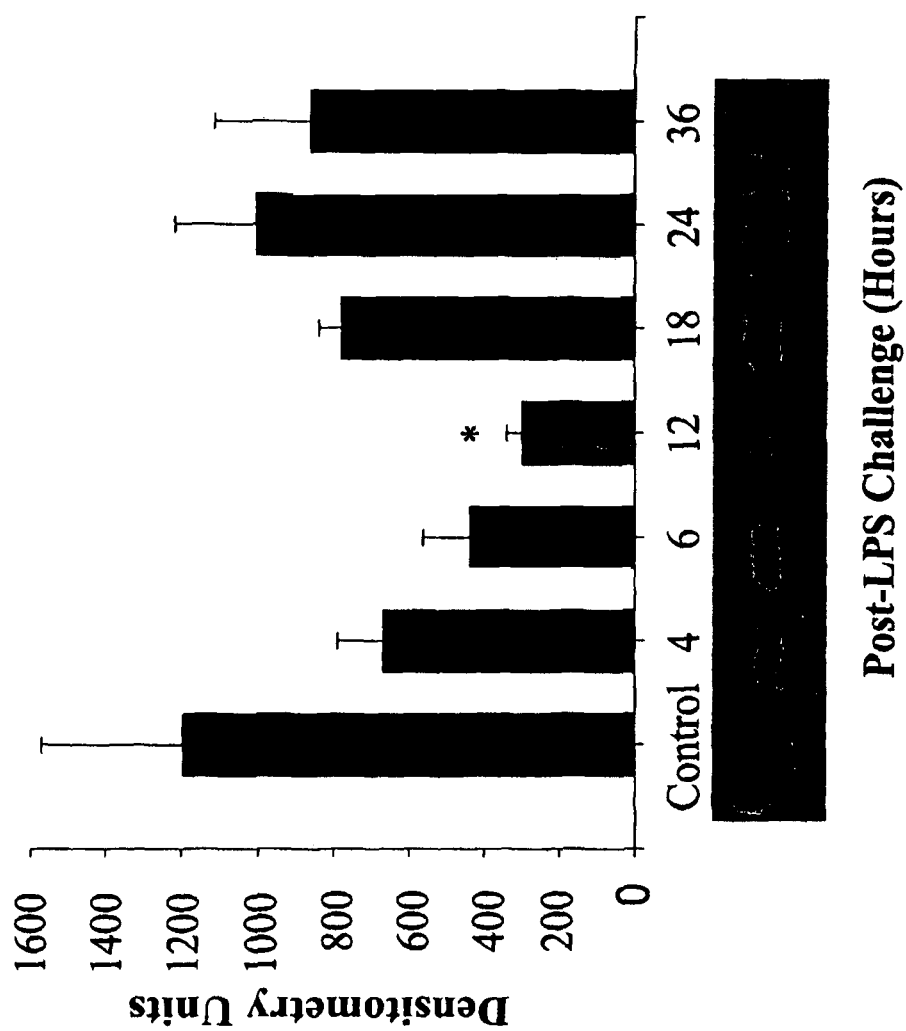
FIG. 1: MIF protein release is detected within 12 h of LPS challenge in cardiac tissue. Each data point is the mean (+/−standard error) of 3 independent Western blot experiments. A representative Western blot is shown below the graph. *$p<0.05$

Various other objects, features, and attendant advantages of the present invention will be more fully appreciated as the same becomes better understood from the following detailed description of the invention, which is not intended to be limiting unless otherwise indicated.

One preferred embodiment of the invention relates to a method of treatment and bioassay involving macrophage migration inhibitory factor (MIF) as cardiac-derived myocardial depressant factor.

One preferred embodiment of the invention relates to a method of treatment and/or prevention of cardiac dysfunction associated with burn injury.

One preferred embodiment of the invention relates to the modulation of MIF as therapy for myocardial infarction.

One preferred embodiment of the invention relates to the modulation of TNF-α in cardiac dysfunction.

One preferred embodiment of the invention relates to a method of cardioprotection by inhibition of CD74.

One preferred embodiment of the invention relates to the modulation of MIF with anti-MIF antibodies.

One preferred embodiment of the invention relates to a bioassay for identifying agents that inhibit MIF activity.

One preferred embodiment of the invention relates to the inhibition of MIF with anti-MIF antibody and concomitant restoration of (post-burning) cardiac function.

One preferred embodiment of the invention relates to a method for the improvement of burn-injury-associated cardiac depression by the administration of anti-MIF antibodies.

One preferred embodiment of the invention relates to the improvement of cardiac function following acute myocardial infarction by the administration of anti-MIF antibody.

One preferred embodiment of the invention relates to the observation that MIF release from the heart, liver and spleen is dependent upon TNF-α receptor I/II signaling, and thus TNF-α may be a therapeutic target.

One preferred embodiment of the invention relates to the neutralization of TNF-α with recombinant human TNFR:Fc.

One preferred embodiment of the invention relates to the neutralization of MIF activity with one or more anti-MIF antibodies.

One preferred embodiment of the invention relates to the discovery of TNF-α as an upstream mediator of MIF.

One preferred embodiment of the invention relates to the observation that CD74 (an MIF receptor) is expressed on cardiomyocytes and is a "critical" mediator of cardiac dysfunction.

One preferred embodiment of the invention relates to the inhibition of MIF and improving cardioprotection by inhibiting the CD74 receptor with one or more anti-CD74 monoclonal neutralizing antibodies.

One preferred object of the invention relates to a method for treating and/or preventing cardiac dysfunction, such as an irregularity or depression in myocardial activity. The method preferably includes administering an effective amount of a composition comprising a macrophage migration inhibitory factor (MIF) inhibitor. The inhibitor can be an antibody. The inhibitor can affect a particular MIF activity including an enzymatic activity, such as tautomerase activity or oxidoreductase activity.

One preferred embodiment of the invention relates to an assay for identifying agents that inhibit MIF activity. The assay preferably involves both a myocyte, either in vitro or in vivo, and MIF in the presence and in the absence of an agent that may inhibit MIF activity. The assay analyzes myocyte activity, for example, using such tools as immunochemistry or echocardiography, based on the presence of MIF and a potential inhibitor.

One preferred embodiment of the invention relates to a method of using this assay to identify an agent that inhibits MIF activity comprising placing a myocyte and MIF in the presence of an agent that may inhibit MIF activity, and determining the effect on myocyte activity. The myocyte may be in vitro or in vivo and the effect may be measured utilizing immunochemistry or echocardiography.

The present inventors have found that MIF is an inducer of myocardial dysfunction, which is known to contribute significantly to the morbidity and mortality of sepsis in humans. In both human patients and animal models, sepsis associated cardiac dysfunction is characterized by biventricular dilatation, decreased systolic contractility, and diminished diastolic relaxation. While not wishing to be bound by theory, it is believed that its pathogenesis is multifaetorial, with systemic and myocardial derived cytokines such as tumor necrosis factor-alpha (TNF-α) involved in inducing its onset.

One embodiment of the present application is directed to identifying whether MIF or other cardiac derived proteins mediate, by paraerine or autocrine mechanisms, myocardial dysfunction in sepsis and other cardiac diseases. Screening microarray analysis of cardiac gene expression in mice suggests that MIF is expressed in the heart, and is differentially regulated after lipopolysaccharide (LPS)-challenge. Given the data that MIF inhibition improves outcome in animals with experimental sepsis, the following examples were constructed to verify whether MIF was expressed by cardiomyocytes in vivo, whether this expression was altered by endotoxin challenge and that MIF had a physiologically important effect on cardiac function. Several of the examples herein demonstrate cardiac MIF expression in vivo, and determine that MIF depresses cardiac function in a sublethal endotoxin challenge in vivo.

MIF is constitutively expressed in the normal myocardium, and is released by cardiomyocytes following endotoxin challenge, with cardiac tissue levels reaching a nadir 12 hours after challenge. Evidence supporting a delayed release is seen in the present application by western blot and immunohistochemistry demonstrating significant release at 12 h from cardiac and spleen tissue, and supported indirectly by the delayed onset of cardiac protection beginning at eight hours, and continuing thereafter. Treatment of LPS challenged mice with anti-MIF monoclonal antibodies significantly improves in vivo cardiac function as evidenced by improvement in left ventricular shortening fraction.

To further demonstrate MIF's myocardial depressant effects, isolated beating mouse hearts (Langendorff perfusion) were perfused with a solution containing a concentration of recombinant MIF (rMIF). Perfusion with rMIF results in significant depression of both systolic and diastolic performance. The present inventors have demonstrated that MIF is synthesized by cardiomyocytes in vivo, and released following LPS challenge. Thus MIF directly mediates cardiac dysfunction and MIF is demonstrated as a pharmacologic target for the improvement of cardiac function in sepsis and other cardiac diseases.

Microarray data on cardiac gene expression highlights that MIF is also expressed in cardiac tissue. Several examples herein indicate that MIF perfusion directly depresses cardiac function in vitro; and moreover, treatment with either of two independent monoclonal antibodies directed against MIF mitigates late myocardial depression.

Another preferred embodiment of the invention relates to a method for treating and/or preventing burn injury associated conditions, including but not limited to cardiac dysfunction, such as an irregularity or depression in myocardial activity. The method preferably includes administering an effective amount of a composition comprising a macrophage migration inhibitory factor (MIF) inhibitor. The inhibitor can inhibit MIF activity and/or MIF production. The inhibitor is preferably an antibody or protein. The inhibitor can affect a particular MIF activity including an enzymatic activity, such as tautomerase activity or oxidoreductase activity. The inhibitor can inhibit or block MIF activity or MIF production in myocardial tissue. The inhibitor can also inhibit or prevent MIF release, such as inhibitors of the ABC transporter.

Another preferred embodiment of the invention relates to an assay for identifying agents that inhibit MIF activity or production. The assay would involve a myocyte, either in vitro or in vivo, and possibly MIF in the presence and in the absence of an agent that inhibits MIF activity or MIF production. The assay would analyze myocyte activity, using such tools as immunochemistry or echocardiography, based on the presence of MIF and a potential inhibitor.

One embodiment of the invention utilizes the role of MIF in burn associated cardiac dysfunction in methods of prevention/treatment and diagnostic assays. Using a murine burn injury model (40% TBSA), the present inventors identified that constitutive cardiac MIF significantly decreased (2.1 fold) 8 hours after burn injury as determined by western blot analysis. Serum MIF was maximal at 4 hours after burn injury (2.2 fold increase). These patterns are consistent with MIF release from pre-formed cytoplasmic stores of cardiac and systemic origin following burn injury. As seen in the examples herein, to determine the effect of MIF in cardiac dysfunction seen after burn injury, mice were pre-treated with anti-MIF neutralizing monoclonal antibodies. Beginning at 4 hours after burn injury (and continuing through 48 hours) mice with burn injury alone demonstrated a depressed left ventricular fractional shortening percentage (FS %) of 38.6+/−1.8% (Sham FS % 56.0+/−2.6%). Anti-MIF treated mice demonstrated a delayed improved cardiac function after burn injury, with complete recovery of function by 24 hours. This demonstrates that the cytokine MIF mediates late burn injury associated cardiac dysfunction, and also demonstrates that MIF is a pharmacologic target for the treatment of burn injury associated cardiac dysfunction as well as other MIF mediated complications such as ARDS associated with burn injury.

Figure 7:
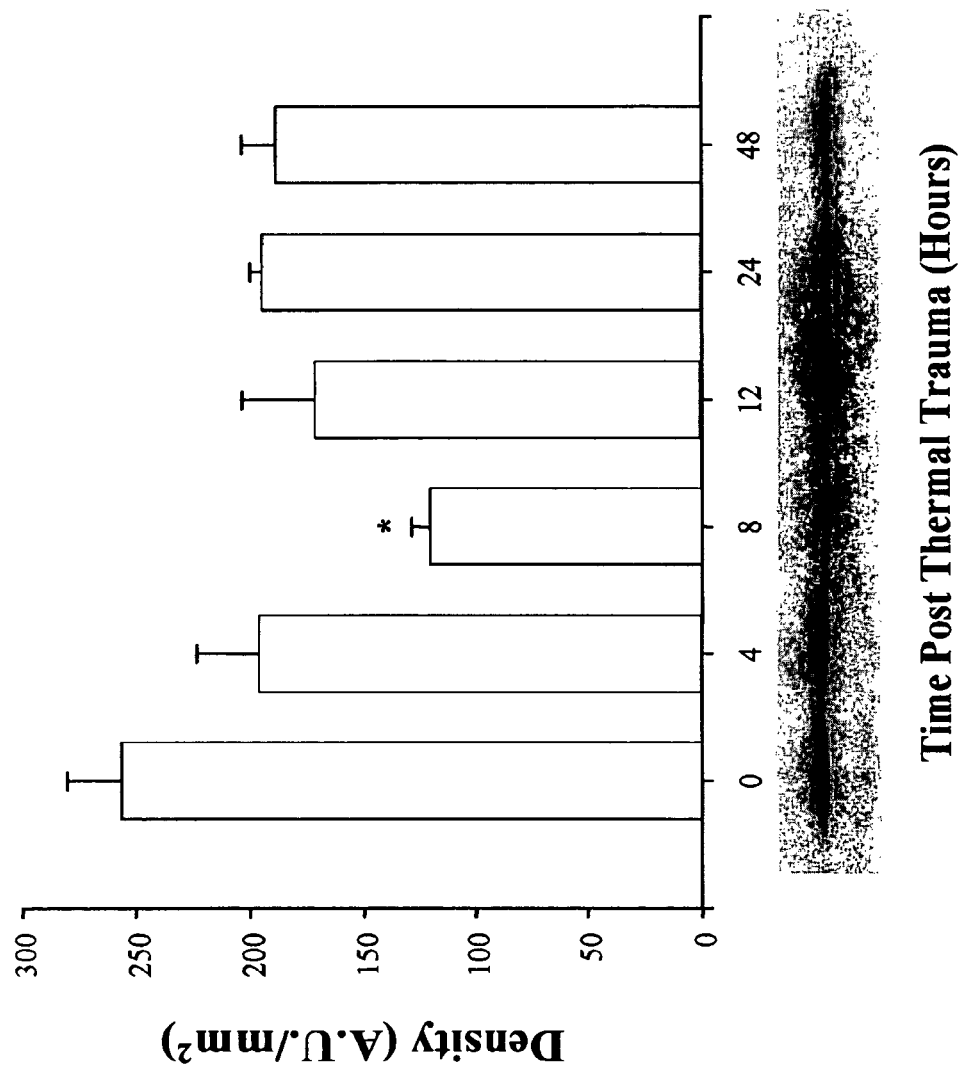
FIG. 7: A graphical representation demonstrating MIF release rate from the heart following thermal trauma. Macrophage migration inhibitory factor (MIF) is constitutively expressed in cardiac tissue and released maximally 8 hours post-burn injury. Each data point represents the mean density in arbitrary units (A.U.)/mm$^2$±SE of 3 independent Western blot experiments. A representative Western blot is shown below the graph. A One Way ANOVA and a multiple comparison procedure using the Tukey method were employed to determine statistical significance compared to the control group (*p<0.05).
Figure 8:
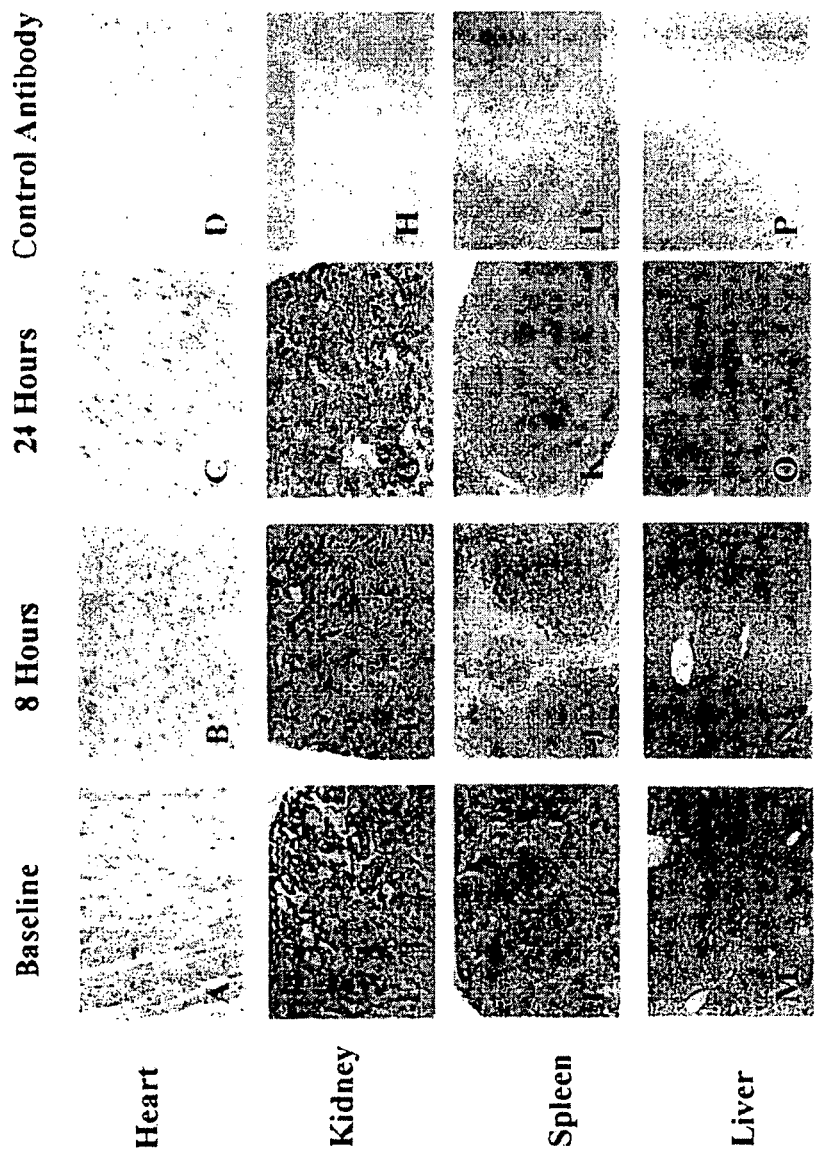
FIG. 8: Immunochemistry staining slides demonstrating MIF presence in various tissue samples. Insert G-MIF, constitutively present in the heart, liver, spleen, lung, and kidney is decreased after burn injury. Preformed MIF in the heart, kidney, and spleen (A, E, I) decreases 8 hours after burn injury (B, F, J), except for liver (M,N) and increases at 24 hours in heart and kidney (C, G), but not heart or liver (K,O) as demonstrated by immunohistochemistry. A negative control (secondary antibody without the primary anti-MIF antibody) consistently demonstrates that no background staining is present at each time point in each organ investigated as represented in the far right column (D, H, L, P). Magnification: 100× (Kidney, Spleen, Liver), 400× (Heart).

After burn injury, MIF is maximally released into the serum by 4 hours (FIG. 9); tissue release occurs to maximum by 8 hours (heart and spleen) (FIGS. 7 & 8). When MIF is neutralized by antibodies, cardiac function improves significantly by 12 hours and completely by 24 hours, demonstrating MIF modulation as a mediator of cardiac dysfunction in vivo following burn injury (FIG. 12).

In a mouse model of burn injury, it has been demonstrated that LPS mediates the associated cardiac dysfunction through its interaction with the Tlr-4 (toll-like receptor 4) and its interaction with IRAK-1. The source of LPS is believed to be gut-derived due to several potential insults associated with burn injury. These include intestinal ischemia, bacterial translocation, and increased intestinal permeability. While not wishing to be bound by theory, it is thought that the production and release of inflammatory factors becomes systemic through gut associated lymphoid tissues.

In a model of sub-lethal endotoxicosis in mice (4 mg/kg LPS), it is observed that MIF mediated late cardiac depressant effects in vivo. It is also determined that recombinant MIF induces an immediate cardiac depression ex vivo by Langendorff assay in an LPS-independent manner. With respect to burn injury, one embodiment of the present invention suitably has several advantages compared to observations made in a model of endotoxicosis. First, MIF is released at an earlier time point in the burn model (4 hours, FIG. 7) compared to the LPS challenge (8 hours) and this increase in systemic MIF concentrations is significantly higher (2.2 fold increase (FIG. 9) vs. 1.5 fold). Secondly, the degree of cardiac dysfunction was not as great in the burn injury model compared to the endotoxicosis model as measured by echocardiography. With respect to burn injury, the present inventors desirably allows fractional shortening percent (an estimate of cardiac output) to be decreased 38% from baseline by four hours (56.2 FS %-34.8 FS %/56.2 FS %) compared to 53.7% in the endotoxicosis model (67.2 FS %-31.1 FS %/67.2 FS %) at four hours. MIF inhibition in accordance with one embodiment of the present invention results in complete cardiac protection by 24 hours (FIG. 12), which did not occur until 48 hours in the endotoxicosis model, although significant protection was first seen by 8 hours in the endotoxicosis model, and not until 12 hours in the burn injury model. This demonstrates that MIF plays a greater role in burn injury associated cardiac dysfunction. Lastly, the increase in cardiac MIF mRNA levels was determined to be significantly increased by 8 hours in burn injury (FIG. 10) and was not increased until 48 hours in the endotoxicosis model. While the cardiac effects of burn injury have been shown to be related to gut derived LPS, the effective insult is more complex than the endotoxicosis model in that it involves the skin as well as the gut and is a more physiologically relevant disease processes.

Figure 12:
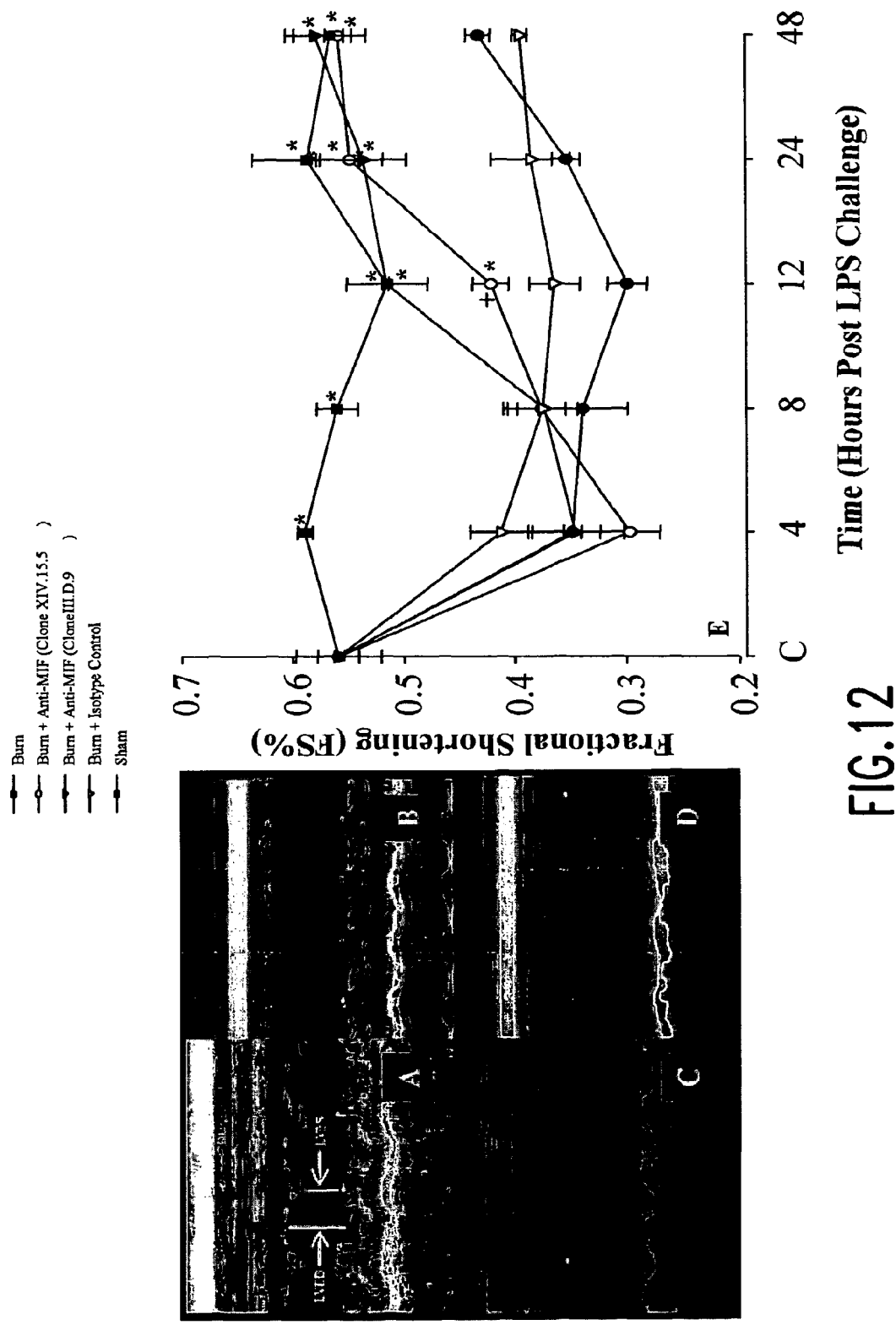
FIG. 12: Echocardiographic and graphical representation of the effects of anti-MIF antibody therapy after burn injury demonstrating the cardioprotective effects of MIF blockade. Echocardiographic assessment of the effects of anti-MIF antibody therapy after burn injury demonstrates the cardioprotective effects of MIF blockade. Representative M-mode echocardiograms in wild-type mice at baseline and 8 hours after burn injury, A and B, respectively. C and D depict representative echocardiograms in burn injury plus anti-MIF treated mice at 4 and 48 hours, respectively. A significant recovery of cardiac function (FS %) is observed in burn injury mice given anti-MIF anti-bodies pre-burn injury (E). Data from each group represent the mean±SE of 9 cardiac cycles from 3 mice monitored at multiple time points. Cardiac function determined by echocardiography is expressed as fractional shortening % (LVED-LVES/LVED×100)±SE and was analyzed using a One Way Repeated Measures-ANOVA and a multiple comparison procedure employing the Tukey Test to determine significant differences between specific groups.

Neutralization of MIF resulted in cardioprotection starting at 12 hours, and marked cardiac dysfunction was identified in mice with burn injury as early as four hours (FIG. 12). TNF-α, IL-1β IL-6, and IL-10 are secreted by cardiomyocytes and TNF-α and IL-1β are the primary mediators of the myocardial depression. The present invention contemplates the role these play in early cardiac dysfunction occurring before MIF mediated cardiac dysfunction. Since MIF is released locally from the heart just prior (8 hours) to the protective effects of anti-MIF treatment (12 hours) seen by echocardiography, the present invention contemplates that MIF plays a significant role in the cardiac dysfunction seen at later time points in this model (12-48 hours after burn injury). Of the ten additional cytokines investigated systemically (FIG. 9), only systemic IL-6 and IL-12 were modulated after burn injury. Systemic IL-12 levels were significantly decreased the first 12 hours, as has been reported in post-surgical sepsis patients. Decreases in this TH1 cytokine is hypothesized as one mechanisms by which survival in sepsis is decreased by impaired innate immune responses to infection which has been identified in burn injury.

Major burn injury has been shown to produce significant increases in plasma and cardiac malondialdehyde (MDA) levels, a major product of lipid peroxidation that results from oxidative stress in tissues. Moreover, antioxidant therapy has been shown to decrease the release of inflammatory cytokines in burn injury linking inflammatory responses to increased oxidative stress. Previous studies have demonstrated that MIF is secreted from cardiomyocytes after oxidative stress, and, without wishing to be bound by theory, this may be one mechanism by which MIF is released. Oxidative stress initiated by $H_2O_2$ results in the activation of ERK1/2 signaling pathway and protein kinase C, the latter of which appears to be responsible for the secretion of MIF. Therefore, the cardiac release of pre-formed MIF may be initiated with increases in oxidative stress in the heart which signals the release of MIF (FIGS. 7 and 8) and upregulates its transcription (FIG. 10) in order to replenish the stores in cardiomyocytes.

Most cytokines have tightly controlled expression that is upregulated after stimulation. MIF, however, exists preformed in substantial amounts and its expression relies not only on de novo protein synthesis, but also from pre-existing stores which are controlled by secretory mechanisms involving ABC transporters. The MIF gene does not encode for an N-terminal signal sequence whose role is to translocate it to the endoplasmic reticulum. MIF is located predominantly in the cytosol in small vesicles and the nucleus which are pinched off and released to the outside of cells. Necrotic cell damage therefore leads to a release of the pre-stored MIF. While not wishing to be bound by theory, since previous studies have clearly demonstrated that burn injury involves skin necrosis in our model, MIF release may be directly released from necrotic cells of the skin, since MIF has been identified in the skin and localized to the basal layers of the epidermis.

In addition to the necrotic release of pre-formed MIF, damaged epidermis and fibroblasts have been shown to increase the expression and secretion of MIF. For example, in atopic dermatitis, MIF is upregulated and plays a pivotal role in the pathophysiology of the disease. Total body UV B exposure in vivo has been shown to increase MIF production, suggesting its involvement in tissue injuries. Injured epidermis and cultured fibroblasts also increase the expression of MIF which contributes positively to the wound healing process. Systemic levels of MIF may increase more quickly and dramatically (2.2 fold by 4 hours in the burn injury model vs. 1.5 fold increase by 8 hours in the endotoxicosis model) in this burn injury model compared to the endotoxicosis model due to factors involving MIF released from burn injured skin.

MIF has been shown has been hypothesized to play a role in ARDS and lung complications of sepsis. Anti-MIF therapy has been shown to decrease pulmonary neutrophil accumulation in acute lung injury associated with sepsis. MIF is expressed in alveolar capillary endothelium and infiltrating macrophages from ARDS patients. MIF expression has been shown to form an amplifying loop with TNF-α effectively linking severe inflammation to these two cytokines in ARDS. Since ARDS is an important and common complication of burn injury, the present invention contemplates anti-MIF therapies that are useful in other than cardiac protective indications, and seriously affect outcomes.

MIF is unique among cytokines because it has multiple enzymatic activities including oxidoreductase and tautomerase activity. Inhibition of its tautomerase activity has been shown to counteract known MIF activities such as its glucocorticoid override activities. Pharmacological inhibitors of MIF tautomerase activity have been developed for diseases anti-MIF therapies have been effective such as sepsis, asthma, atopic dermatitis, and acute respiratory syndrome (ARDS).

The cytokine MIF plays a significant role in the late cardiac dysfunction associated with burn injury. MIF itself is a direct cardiac depressant and has a delayed release from the heart. The delayed release of MIF and development of inhibitors that potentially inhibit the activity of MIF make MIF a potential target for diseases such as burn injury associated with morbidity and mortality related to its cardio-pulmonary effects.

In another embodiment of the invention, the present inventors have found that MIF release from the heart, liver, and spleen is dependent upon TNF receptor I/II signaling after LPS challenge. Additionally, the present inventors identify TNF receptor I/II signaling independent release into the serum of MIF. Without TNF receptor signaling, MIF levels appear slightly delayed (12-24 hours compared to 8 hours in wild type) and slightly increased (1.7-2.3 fold baseline compared to 1.5 increase in wild type mice). Moreover, the TNF receptor independent MIF release in TNF receptor I/II deficient mice (TNFR−/−) is sufficient to mediate cardiac dysfunction by at least 24 hours after LPS challenge despite the lack of MIF release from tissues which has been previously identified in wild type mice. Early cardiac dysfunction was identified in the TNFR−/− mice and, without wishing to be bound by theory, is believed to be likely due to known mediators that the present inventors have identified to be highly expressed in this model (IL-1β, IL-6) in addition to other potential mediators (e.g. IL-18 as well as other mediators). In isolated hearts (Langendorf prep), MIF was determined to induce an immediate (within 20 minutes) cardiac dysfunction (systolic and diastolic) directly in both TNFR−/− and wild type mice to the same extent. LPS induced cardiac dysfunction in the TNFR−/− mice, however, was completely ablated by 48 hours with MIF neutralization with antibodies indicating that TNF receptor mediated independent release of MIF was capable of inducing a profound late cardiac dysfunction (24 and 48 hours) in a model of endotoxicosis.

The cytokine MIF is constitutively expressed in numerous cell types including lymphocytes, macrophages, and the anterior pituitary. Many tissues also contain MIF including the heart, lung, liver, adrenal, spleen, kidney, skin, muscle, thymus, skin, and testes. The mechanism of secretion has recently been described in LPS stimulated monocytes. Inhibitors of classical protein secretion such as monensin or brefelding A do not inhibit the secretion of MIF, suggesting a non-classical protein export route. When inhibitors of ABCA1 (ATP binding cassette A1) transporters (glyburide and probenicide) were given, MIF secretion did not occur. MIF is located predominantly in the cytosol in small vesicles and the nucleus which are pinched off and released to the outside of cells. This non-classical, vesicle-mediated secretory pathway has been shown to be a mechanism of secretion of other important inflammatory mediators such as HMGB1, which has been shown to play a significant role in inflammatory diseases and specifically sepsis. In the present invention, the dependence of MIF secretion on TNF-α signaling in several tissues is described for the first time.

MIF has numerous biological activities including glucocorticoid antagonist properties, catalytic properties which are regulated through the coactivator JAB1/CSN5 and the cell surface protein CD74/Ii chain. Specific secretion of MIF results after inflammatory stimuli such as endotoxin (LPS) and tumor necrosis factor, as well as hormones such as ACTH, and angiotensin II. In addition to immune cells, endocrine cells and some epithelial cells secrete MIF. Secretion is due to an enhancement of MIF expression and de novo synthesis as well as an induction of the release from pre-existing stores; both of which have been previously demonstrated in the heart.

Cardiac MIF has been reported to be released maximally at 12 hours after LPS challenge in wild type mice. Serum MIF levels in wild type mice after LPS challenge maximally release at 8 hours, corresponding to early protection of cardiac dysfunction. When TNF-α signaling is inhibited after LPS challenge by either Enbrel® pretreatment or in TNFR−/− mice, the MIF levels peak later and slightly higher, indicating that TNF-α has some control over serum MIF levels, but does not inhibit MIF release. When wild type mice were pretreated with anti-MIF neutralizing antibodies and subjected to an LPS challenge (4 mg/kg), an initial severe cardiac dysfunction was seen at four hours that was identical to mice given LPS alone. However, initial significant protection was seen at 8 hours and improved until 48 hours where cardiac function was not significantly different from control animals. Since MIF had a nearly immediate and direct cardiac effect in isolated wild type hearts, it was believed that MIF played a role in cardiac function which paralleled its delayed release. However, in the present invention it is demonstrated that non-cardiac release of MIF can have significant effects on function in vivo as well (24 and 48 hours). These effects occur later than previously described (initial protection at 8 hours) and parallel a delay in MIF release systematically when TNF-α signaling is blocked (12-24 hours) compared to wild type mice (maximum MIF release at 8 hours).

It is believed that the early cardiac dysfunction can be attributed to several cytokines which have been shown to mediate sepsis (and LPS) associated cardiac dysfunction such as TNF-α, IL-1β, and IL-18. A temporal discordance between myocardial TNF-α levels and contractile dysfunction in endotoxemia has been reported. These findings of LPS associated myocardial dysfunction did not occur until TNF-α levels returned to baseline contradict other findings which have reported protection from LPS induced cardiac dysfunction after the neutralization of TNF-α. These findings and others have led to the hypothesis that TNF-α is required for LPS induced increases of downstream mediators such as IL-1β, IL-6, IL-18 among other not yet identified factors. The present inventors demonstrate that TNF signaling mediates some (MIF secretion from heart, liver, spleen), but not all, of the effects of MIF in their model of endotoxemia.

The sentinel role of TNF-α signaling has been studied by other investigators, specifically in relationship to the cytokine IL-18 in endotoxemia models. After LPS challenge in TNF-α knockout (−/−) mice, IL-18 levels in the heart are not significantly changed, while wild type mice demonstrated significant increases in IL-18 levels. When IL-18 is neutralized, this study demonstrated that the LPS induced cardiac dysfunction is reduced and that IL-18 appears to have downstream effects on tissue TNF-α, IL-1β, as well as ICAM-1/VCAM-1 levels. While this study focused on the myocardial production and release of IL-18 in the myocardium, non-cardiac sources of IL-18 were not investigated. This study is believed to be similar to that of the present inventors in the TNR-α dependence on tissue (cardiac) production/release of IL-18.

Similarly, it is important to note a previous study that identified the effects of TNF-α inhibition on myocardial cytokine mRNA expression as well as plasma cytokine levels after LPS challenge. Inhibition of TNF partially but significantly reduced plasma levels of IL-1β, IL-6, and MCP-1 but not MIF, TNF, IL-10, or IL-12 at 2 hours; in contrast anti-TNF pretreatment significantly reduced myocardial expression of IL-1β but not other cytokines including MIF at this early time point. Since the present inventors have shown that MIF is shown to release later than 2 hours (peaks at 12 hours), the present inventors describe the TNF independent and TNF dependent MIF pathways for the first time that parallel IL-1β, IL-6, and MCP-1 in this previous study. These are important findings since most of these cytokines have been shown to directly mediate cardiac dysfunction.

Figure 19:
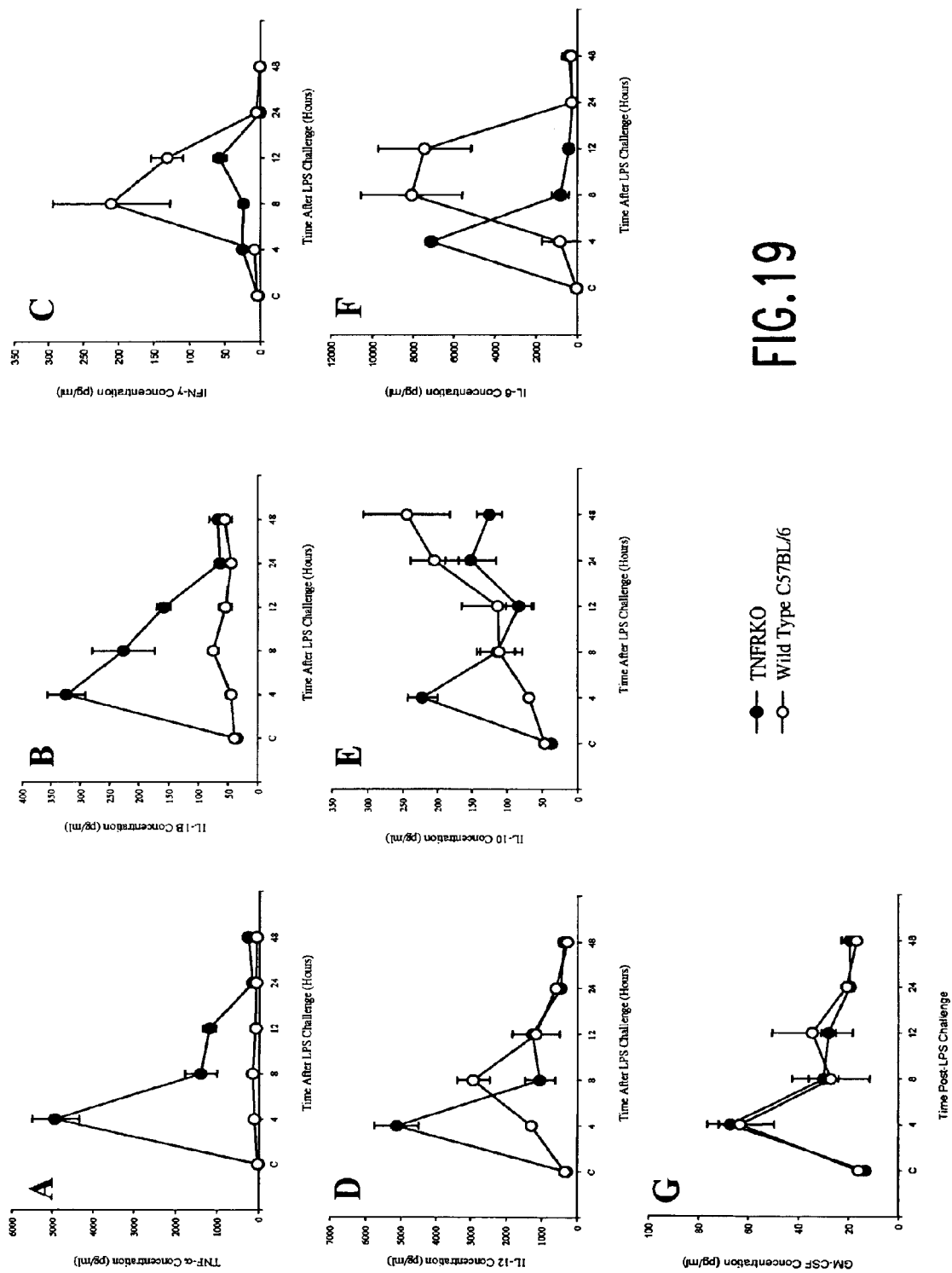
FIG. 19: Serum cytokine determination in wild type and TNFR−/− mice after LPS challenge. An inflammatory cytokine panel was assayed on the Luminex platform for: (A) TNF-α, (B) IL-1β, (C) IFN-γ, (D) IL-12, (E) IL-10, =(F) IL-6, (G) GM-CSF, and IL-2, IL-4, IL-5 (data not shown). Data are expressed as the mean +/−standard error of serum cytokine concentrations from 3 independent experimental mice at each time point.

While the cardiac dysfunction of the TNFR−/− mice after LPS challenge in this study (18.2% (45.9-27.7 FS %) is not as profound as that determined in wild type mice in our previous study 36.7% (67.3-30.6), the depression is significant. Since multiple cytokines have been attributed to the early cardiac dysfunction after LPS challenge, we determined serum cytokine levels in the TNFR−/− model. The levels of TNF-α was dramatically increased compared to wild type mice, however, with no functional receptors (TNF receptor I or TNF receptor II), it effects were not mediating the early cardiac dysfunction seen. However, increases in IL-1β and IL-6 were clearly seen at 4 hours (31.2 and 8.5 fold above wild type mice, respectively) and likely contributed to early cardiac dysfunction in addition to other cytokines such as IL-1β recently described as well as other mediators not yet described. The role of TNF-α signaling in the regulation of TNF-α secretion has previously been described. However, the present inventors have demonstrated for the first time that TNF-α receptor signaling regulates IL-1β, IL-12, and IL-10 by a negative feedback mechanism and positively regulates IFN-γ (FIG. 19). Similarly, mice deficient in IL-6 have augmented expression of IL-1β and TNF-α after LPS challenge and the present inventors contemplate that cardiac IL-6 suppresses the expression of proinflammatory mediators including itself by a negative feedback mechanism.

TNF-α signaling occurs through 2 receptors, TNF-α receptor 1 and 2. These two pathways have divergent signaling pathways. The interaction of TNF-α and receptor 1 activates several signal transduction pathways including NF-kB, which the TNF-α receptor does not. To investigate the which of the two possible TNF receptors were responsible for the inhibition of MIF release in the heart, the present inventors challenged mice in which IkB overexpression in the heart resulted in nearly complete NF-kB inhibition. By western analysis, the present inventors demonstrated that no release occurred in the same manner as the TNFR−/− mice at all time points tested (data not shown, identical to FIG. 2A). These mice have circulating TNF-α equivalent to wild types (since NF-kB inhibition is cardiac specific). Additionally, these mice express MIF in the serum similar to wild type mice. Accordingly, the present invention contemplates that the TNF receptor 1 may mediate the tissue release seen in wild type mice from the heart. Since the phenotype of this heart is completely protected after LPS challenge by echo during the first 48 hours (data not shown), the present inventors contemplate that circulating MIF requires upstream NF-kB mediated proteins to be signal (TNF-α, IL-1β) or that MIF mediates its effects by NF-kB itself.

Figure 20:
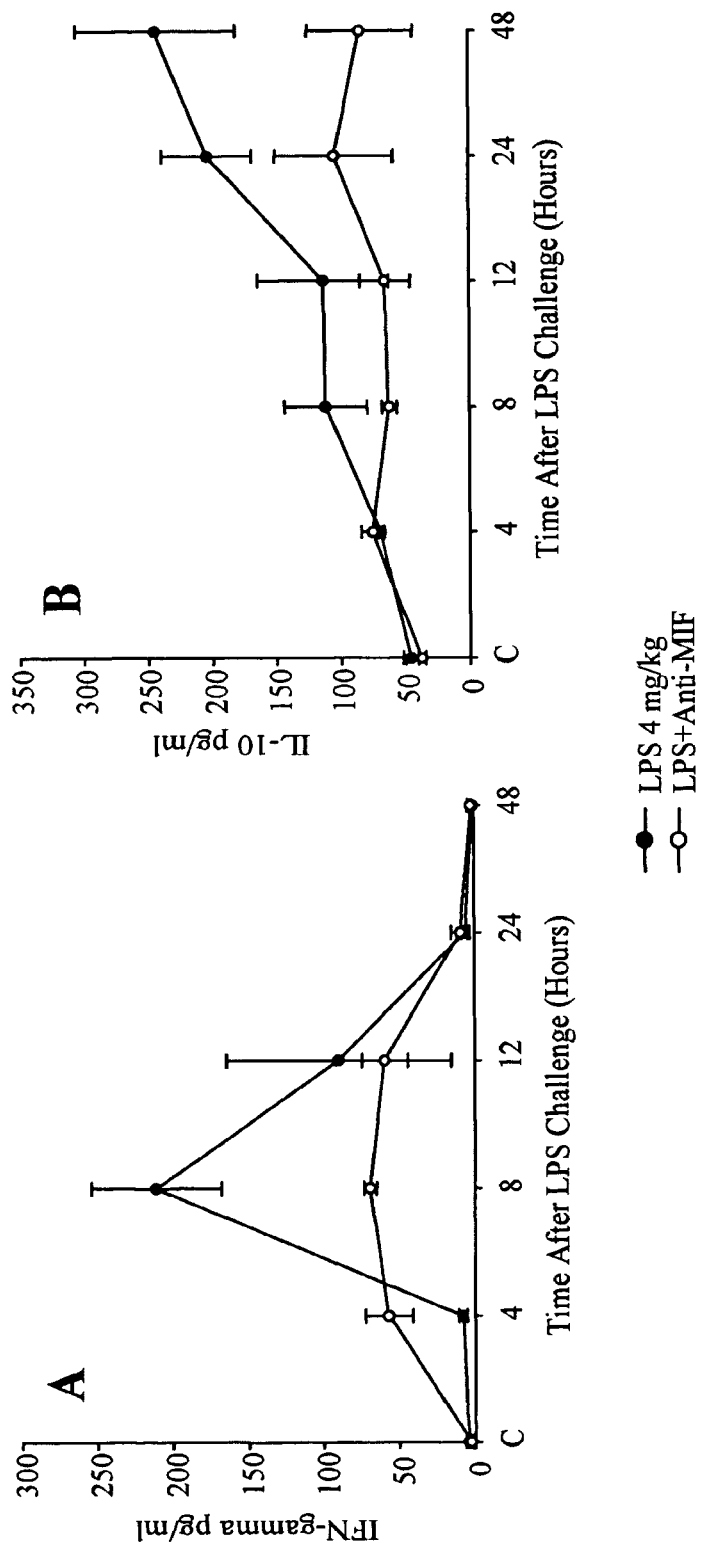
FIG. 20: Serum cytokine determination in wild type after LPS challenge with or without anti-MIF pre-treatment (90 minutes). Shown are the modulated cytokines: (A) IFN-γ and (B) IL-10 as assayed on the Luminex platform. Data are expressed as the mean +/−standard error of serum cytokine concentrations from 3 independent experimental mice at each time point.

The release of IL-10 and IFN-γ after LPS challenge in wild type mice is attenuated when they are pre-treated with MIF neutralizing antibodies (FIG. 20). Since MIF has a delayed release, these are likely the cytokines affected due to their temporal relationship to MIF, occurring after MIF is released (FIG. 13). These findings indicate that MIF activity plays a significant role in IL-10 and IFN-γ release after endotoxin challenge, although it is likely not the only signal for their release. It is interesting to note that in the TNFR−/− mice (FIG. 19C) that IFN-γ release is inhibited as well, making both TNF and MIF necessary for its release. Similarly, in a model of dextran sulfate-induced colitis by anti-MIF antibodies, IFN-γ was significantly suppressed. The expression of iNOS in cardiac myocytes have been shown to expressed when TNF-α and LPS are given with IFN-γ, but NOT without IFN-γ. Since iNOS itself plays a role in the regulatory pathways of LPS associated cardiac dysfunction, these cytokine pathways are complex and likely interact closely.

Efforts at inhibiting TNF-α in order to reduce morbidity and mortality in sepsis and septic shock have previously failed clinically, even though pre-clinical studies in mice protected against endotoxin challenges. The present inventors have found that the inhibition of TNF-α signaling prior to LPS challenge results in the inhibition of MIF secretion from the tissues, although serum MIF release is unaffected. Moreover, when Enbrel was given just immediately prior to or after LPS challenge instead of 90 minutes prior, tissue release of MIF occurred sporadically (data not shown) which may account for additionally downstream MIF effects by this therapy. While not wishing to be bound by theory, these findings indicate mechanisms by which anti-TNF-α therapies may not have worked due to MIF effects.

While this study of LPS challenge in the absence of a live infection cannot be directly extrapolated to sepsis-induced myocardial dysfunction, it is important to note that MIF has been shown to be physiologically relevant in a model of live polymicrobial peritonitis (CLP). When MIF neutralizing antibodies were given to TNF-α−/− mice (particularly susceptible to CLP insult) MIF was protective against lethality (62% survival at 9 days in MIF neutralized mice compared to 0% with CLP only) at 15 hours. Similarly, in wild type mice, MIF neutralizing antibodies were protective for 9 days (endpoint of experiment) where 81% survived compared to 31%, even when antibody was given up to 4.5 hours after the insult (61% survival compared to 5%). Accordingly, the present inventors contemplate anti-MIF therapies against sepsis-induced myocardial dysfunction.

Since MIF release is delayed and partially unaffected by blocking of important upstream mediators such as TNF-α, it may represent one good therapeutic target. To this end, the inhibition of MIF's tautomerase activity that mediate some of its biological functions may be intervened pharmacologically. Moreover, recent non-classical secretory mechanisms of release also are potential target for therapy. However, it is important to realize that other significant targets in sepsis that are known (HMGB1) as well as undescribed targets still exist. Therefore, it is important to understand the effects of therapeutic invention of all of these mediators.

The present inventors have demonstrated that MIF plays a significant role in LPS induced cardiac dysfunction which is believed to contribute to myocardial dysfunction during sepsis. Because TNF-α is thought to be an important sentinel cytokine in LPS induced cardiac dysfunction, the effects of blocking TNF-α signaling pathways in vivo on MIF induced cardiac dysfunction have been investigated. Serum concentrations and the temporal distribution of MIF was slightly increased and delayed by the inhibition of TNF-α signaling (maximally increased 12-24 hours (1.7-2.3 fold baseline with TNF-α signaling inhibition vs. 8 hours in wild type (1.5 fold increase). The release of pre-formed MIF from heart, liver, and spleen did not occur after LPS challenge after inhibition of TNF-α signaling unlike the delayed maximum release at 12 hours seen previously in wild type mice. Northern analysis of cardiac MIF mRNA revealed no significant changes in transcription after LPS challenge. When recombinant MIF was applied to isolated TNFR−/− hearts (Langendorff preparation), a significant decrease in cardiac function was detected equal to wild type mice, indicating that MIF signaling was TNF-α. Echocardiography of TNFR−/− mice after LPS challenge demonstrated an early cardiac dysfunction (18.2% decrease in fractional shortening %) that minimally improved after 48 hours. When MIF was neutralized by monoclonal antibodies, cardiac function significantly improved by 24 hours and completely recovered by 48 hours, indicating that MIF played a role in late LPS associated cardiac dysfunction despite the lack of tissue release. This study demonstrates for the first time that MIF release from cardiac and other tissues is dependent upon TNF signaling, and serum release of MIF is unaffected by a lack TNF signaling after LPS challenge and is adequate to mediate cardiac dysfunction.

Macrophage migration inhibitory factor (MIF) is pluripotent cytokine with direct and significantly deleterious effects on heart function during sepsis (severe infections). One embodiment of the present invention demonstrates in a mouse model that the inhibition of MIF activity can profoundly improve cardiac function following acute myocardial infarction (See FIGS. 21-25). This improvement is evident within hours, and lasts for the duration of the experiment (1 week). It is highly likely that modulation of MIF will decrease infarct size and other pathologic parameters. The degree of improvement in cardiac function is remarkable, and substantially in excess by at least 10 fold compared to other immune targets such as TNF-alpha.

Prior to the present invention there were no treatments for myocardial infarction which target chemical/cytokine mediators of heart dysfunction and acute myocardial tissue injury. Current technology aims to minimize infarction by therapies such as TPA. Once TPA or similar therapy is given, there are no drug therapies to prevent cardiogenic shock/failure aside from standard inotropes (dobutamine) or mechanical devices (intra-aortic balloon pump). Therapies to block MIF being given simultaneously with TPA or balloon angioplasty to further improve both the short term as well as the long term heart function, and potentially minimize infarct size are contemplated herein.

One embodiment of the present invention solves the problems of acute and chronic heart dysfunction following acute myocardial infarction. The present invention makes it possible to provide a unique class of therapies in that it modulates an immune mediator, i.e., MIF. Without wishing to be bound by theory, it is believed that the present invention may directly decreases infarct size. There is no equivalent therapy to preserve long term cardiac function. For short term function, modulation of MIF activity in accordance with the present invention would minimize the need for intra-aortic balloon pumps and other mechanical devices. Suitable monoclonal anti-MIF antibodies are obtained from Cytokine Pharma-Science, Inc., King of Prussia, Pa.

Another embodiment of the present invention relates to inhibition of CD74 to protect cardiodysfunction associated with severe disease such as sepsis, trauma, acute MI, and congestive heart failure. While CD74 has been described on circulating immune cells and antigen presenting cells (in association with MHC Class II), until the present invention, the presence of CD74 in the heart (as well as other organs) has not been reported. More importantly, the function role of CD74 on cardiac function in physiological or disease processes has not previously been demonstrated. While CD74 has been shown to mediate MIF activity in vitro, this has not been confirmed independently and is restricted to fibroblasts and leukocytes.

Suitable anti-human CD74 antibodies are available, for example, from BD Biosciences (product catalog numbers 555538 (Clone M-B741; Format Purified; Isotype Mouse $IgG_{2a}$, κ; W. S, No V CD74.4; Reactivity Human) and 555612 (Clone LN2; Format Purified; Isotype Mouse $IgG_1$, κ; W.S, No V CD74.3; Reactivity Human)

The present invention makes it possible to use anti-cytokine therapy (including anti-MIF) in cardiac diseases. Preliminary experiments using anti-TNF therapy in sepsis models did not work. Additionally, MIF, the putative cytokine blocked by CD74 inhibition, is a cytokine that occurs later, and in our model of acute MI is increased for several weeks after the insult, allowing for intervention during any of that time.

Cardiac dysfunction early in acute MI and sepsis accounts for the high morbidity and mortaility associated with each of these diseases. The present inventors contemplate cytokine therapy that can enhance performance and potentially lower the morbidity associated with each.

Most therapeutic interventions in cardiac disease have focused on reperfusion (MI) or inotropes (MI and sepsis). By one embodiment of the present invention, intervening with the CD74 receptor, the putative receptor for MIF, both acute and chronic cardiogenic impairment may be attenuated and improve survival/outcomes.

MIF is secreted from cardiomyocytes following LPS challenge, and directly mediates a late onset (>6 hours) cardiac dysfunction. In immune cells, CD74 was determined to be the MIF receptor, exerting effects via ERK1/2 intracellular signaling pathways. To determine if CD74 mediates MIF-induced cardiac dysfunction in sepsis, the present inventors challenged: 1) wild type mice (C57BL/6) with LPS; 2) wild type mice pre-treated with anti-CD74 monocolonal neutralizing antibodies; and challenged with LPS, and 3) CD74 knock-out mice with LPS (4 mg/kg). Serial echocardiography was performed and fractional shortening (FS %) was determined. At 24 hours, significant dysfunction was observed in WT mice given LPS (FS %=31.6%±3.3%) compare to controls (FS %=58±1%). In both anti-CD74 antibody treated and CD74 knock-out mice challenged with LPS, cardiac function was significantly improved compared to wild type mice given LPS alone (FS %=49±3.6% and 53.3±2.4%, respectively, p<0.05). As CD74 expression has never been documented in the heart, the present inventors performed immunoblots and histochemistry which confirmed that CD74 was constituitively present on cardiac cell membranes and in the cytosol; and was substantially regulated after LPS challenge (nearly absent at 12 hours->4 fold decrease). The present inventors demonstrate that CD74 is expressed on cardiomyocytes and is a critical mediator of cardiac dysfunction.

Another embodiment of the present invention relates to the inhibition of MIF activity by use of one or more soluble MIF receptor or MIF receptor antagonist. As an example, with anti-TNFα therapies, REMICADE™ or INFLIXIMAB™ (antibody TNFα) and ENBREL™ or ETANERCEPT™ (soluble TNF-receptor) are suitable. This method includes administering one or more of the soluble MIF receptor and/or MIF receptor antagonist in an effective amount for treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, or a combination thereof to a subject in need thereof.

Another embodiment of the present invention relates to the use of small molecule MIF inhibitors (sometimes called "MIF antagonists" or "isoxazoline compounds") in treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, or a combination thereof.

In the following chemical formulae, the use of the superscript on a substituent is to identify a substituent name (e.g., "$R^2$" is used to indicate an $R^2$-named substituent), while the use of a subscript is used to enumerate the number of times a substituent occurs at that molecular site (e.g., "$R_2$" or "$(R)_2$" both are used to indicate two substituents simply named as "R").

A suitable small molecule MIF inhibitor for use in the methods herein has the following Formula I:

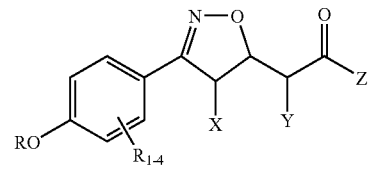

wherein:
$R_{1-4}$ are, independently, R, halo, $N_3$, CN, OH, NRR', or SH;
R and R' are, independently, H or $C_{1-6}$ alkyl;
X is R, halo, $N_3$, CN, OR, NRR', SH, =O, =$CH_2$, or A;
A is a substituted or unsubstituted aromatic ring;
Y is R, NRR', NRR" or $(CH_2)_n$-A;
Z is R, OR, OR", NRR', NRR", or A;
R" is a saturated or unsaturated, straight or branched chain $C_2$-$C_{18}$;
and n is 0 or 1.

Preferably, the compound of Formula I is a p-hydroxyphenyl-isoxazoline-containing compound, wherein each of R, $R_{1-4}$, X and Y is H or —$CH_2$-A, and Z is OR. More preferably, the compound of Formula I is an ester of (R)-3-(4-hydroxyphenyl)-4,5-dihydro-5-isoxazolineacetic, particularly the acid methyl ester thereof (sometimes identified as "ISO-1" or "CPSI" or "CPSI-26" herein) which is also known as p-hydroxyphenol-isoxazoline methyl ester. Still more preferably the compound is an ester of 2-{3-(4-hydroxy-phenyl)-4,5-dihydro-isoxazol-5-yl}-3-phenyl-propinoic acid, particularly the methyl ester thereof (identified as "ISO-2").

Other suitable small molecule MIF inhibitors for use in the method herein have the following Formulas II or III:

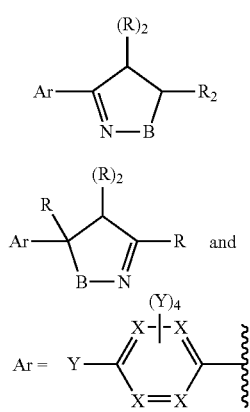

wherein B is either oxygen or sulphur and each "R" is independently defined:

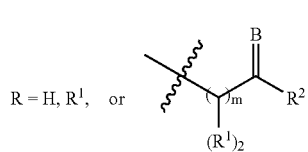

with the requirement that each "R" cannot only occur as hydrogen on either Formula II or III (i.e., at least one R on either Formula II or III is an "R" substituent other than hydrogen), and any B is independently either oxygen or sulphur; any $R^1$ is independently hydrogen, $(C_1-C_6)$alkyl or some other suitable substituent, any $R^2$ is an amine, an alkoxy or some other suitable substituent; and "m" is independently either zero or an integer from one to twenty;

each X is independently either carbon or nitrogen; and when any X is carbon, then Y is the substituent defined independently for each X as

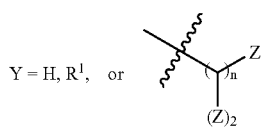

each Z is independently either hydrogen, hydroxyl, halogen, or some other suitable substituent; and "n" is independently any of 0, 1, 2, 3, or 4;

and pharmaceutically acceptable salts and prodrugs thereof.

The present invention also relates to the pharmaceutically acceptable acid addition salts of the compounds of general Formulas I, II, or III. The acids which are used to prepare the pharmaceutically acceptable acid addition salts of the aforementioned base compounds of this invention are those which form non-toxic acid addition salts, i.e., salts containing pharmacologically acceptable anions, such as the chloride, bromide, iodide, nitrate, sulfate, bisulfate, phosphate, acid phosphate, acetate, lactate, citrate, acid citrate, tartrate, bitartrate, succinate, maleate, fumarate, glutamate, L-lactate, L-tartrate, tosylate, mesylate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate))salts.

The invention also relates to base addition salts of the small molecule MIF inhibitors. The chemical bases that may be used as reagents to prepare pharmaceutically acceptable base salts of those compounds of general Formulas I, II, or III that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds and prodrugs of the small molecule MIF inhibitors can exist in several tautomeric forms, and geometric isomers and mixtures thereof. All such tautomeric forms are included within the scope of the present invention. Tautomers exist as mixtures of tautomers in solution. In solid form, usually one tautomer predominates. Even though one tautomer may be described, the present invention includes all tautomers of the small molecule MIF inhibitors.

The present invention also includes atropisomers of the small molecule MIF inhibitors. Atropisomers refer to compounds of the small molecule MIF inhibitors that can be separated into rotationally restricted isomers. The small molecule MIF inhibitors may contain olefin-like double bonds. When such bonds are present, the small molecule MIF inhibitors exist as cis and trans configurations and as mixtures thereof.

A "suitable substituent" is intended to mean a chemically and pharmaceutically acceptable functional group i.e., a moiety that does not negate the inhibitory activity of the small molecule MIF inhibitors. Such suitable substituents may be routinely selected by those skilled in the art. Illustrative examples of suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, amino groups, alkyl- and dialkylamino groups, carbamoyl groups, alkylcarbonyl groups, alkoxycarbonyl groups, alkylaminocarbonyl groups dialkylamino carbonyl groups, arylcarbonyl groups, aryloxycarbonyl groups, alkylsulfonyl groups, arylsulfonyl groups and the like.

Preferred small molecule MIF inhibitors may be found in U.S. provisional application 60/556,440, filed Mar. 26, 2004, U.S. provisional application 60/296,478, filed Jun. 8, 2001; and U.S. application Ser. No. 10/164,630, filed Jun. 10, 2002, the entire contents of each of which is hereby incorporated by reference for all purposes.

Preferably, in this embodiment, an effective amount of one or more small molecule MIF inhibitors and/or salts thereof is administered as active ingredient to a subject in need thereof. Combinations of small molecule MIF inhibitors are also possible.

The small molecule MIF inhibitor compounds can also be administered in form of their pharmaceutically active salts and/or prodrugs as appropriate. Combinations of salts and/or prodrugs are possible, as are combinations of salt-forms and non-salt-forms of the small molecule MIF inhibitor.

Another embodiment of the present invention relates to pharmaceutical compositions suitable in treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, or a combination thereof, which includes one or more small molecule MIF inhibitors and/or salts thereof as active ingredient and at least one pharmaceutically acceptable carrier, excipient, adjuvant and/or diluent.

Another embodiment of the present invention relates to the administration, to a subject in need thereof, of an effective amount of a composition which includes at least one small molecule MIF inhibitor, salt thereof, and/or prodrug thereof and at least one anti-MIF antibody in treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, or a combination thereof.

Another embodiment of the present invention relates to pharmaceutical compositions suitable in treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, or a combination thereof, which includes an effective amount of a combination of at least one small molecule MIF inhibitor, salt thereof, and/or prodrug thereof and at least one anti-MIF antibody, and at least one pharmaceutically acceptable carrier, excipient, adjuvant and/or diluent.

Another embodiment of the present invention relates to the administration, to a subject in need thereof, of an effective amount of a composition which includes a combination of at least one small molecule MIF inhibitor, salt thereof, and/or prodrug thereof, at least one anti-TNFR antibody and at least one anti-MIF antibody in treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, or a combination thereof.

Another embodiment of the present invention relates to pharmaceutical compositions suitable in treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, or a combination thereof, which includes an effective amount of a combination of at least one small molecule MIF inhibitor, salt thereof, and/or prodrug thereof, at least one anti-TNFR antibody and at least one anti-MIF antibody, and at least one pharmaceutically acceptable carrier, excipient, adjuvant and/or diluent.

Another embodiment of the present invention relates to the administration, to a subject in need thereof, of an effective amount of a composition which includes a combination of at least one small molecule MIF inhibitor, salt thereof, and/or prodrug thereof, at least one anti-CD-74 antibody and at least one anti-MIF antibody in treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, or a combination thereof.

Another embodiment of the present invention relates to pharmaceutical compositions suitable in treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, or a combination thereof, which includes an effective amount of a combination of at least one small molecule MIF inhibitor, salt thereof, and/or prodrug thereof, at least one anti-CD-74 antibody and at least one anti-MIF antibody, and at least one pharmaceutically acceptable carrier, excipient, adjuvant and/or diluent.

Another embodiment of the present invention relates to the administration, to a subject in need thereof, of an effective amount of a composition which includes a combination of at least one small molecule MIF inhibitor, salt thereof, and/or prodrug thereof and at least one anti-CD-74 antibody in treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, or a combination thereof.

Another embodiment of the present invention relates to pharmaceutical compositions suitable in treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, or a combination thereof, which includes an effective amount of a combination of at least one small molecule MIF inhibitor, salt thereof, and/or prodrug thereof, at least one anti-CD-74 antibody, and at least one pharmaceutically acceptable carrier, excipient, adjuvant and/or diluent.

Without wishing to be bound by theory, it is believed that neutralization of tautomerase activity (which the cytokine MIF has been shown to have) with small molecule MIF inhibitors results in or contributes to the inhibition of cardiodepression that occurs after myocardial infarction. Inhibition of tautomerase with small molecule inhibitors results in similar cardioprotection as anti-MIF antibodies. Since MIF has been shown to have tautomerase activity and it has been suggested in in vitro studies to mediate its activity, it is believed that neutralization of MIF may occur after its tautomerase activity is inhibited.

The present inventors have found that inhibiting MIF and/or neutralizing MIF tautomerase activity provides an anti-cytokine/inflammation therapy against cardiac diseases. Inhibition of MIF improves cardiac function after myocardial infarction and makes it possible to help with the acute sequelae of myocardial infarctions, such as reducing cardiac dysfunction early in acute myocardial infarction and reducing the associated high morbidity and mortality. One advantage the present invention has over current technologies is that unlike therapeutic interventions in cardiac disease that focus on inotropes, the present invention, by treating and/or preventing the cause of the cardiac dysfunction, both acute and chronic cardiogenic impairment may be attenuated and improve survival/outcomes.

One embodiment of the present invention relates to pharmaceutical compositions comprising at least one compound of the present invention as an active ingredient (and/or salt and/or prodrug thereof) and at least one pharmaceutically acceptable carrier, excipient, adjuvant and/or diluent.

The compounds can also be administered in form of their pharmaceutically active salts optionally using substantially nontoxic pharmaceutically acceptable carrier, excipients, adjuvants or diluents. The compositions of the present invention may be prepared in any conventional solid or liquid carrier or diluent and optionally any conventional pharmaceutically-made adjuvant at suitable dosage level in a known way. The preferred preparations are in administrable form which is suitable for oral application. These administrable forms, for example, include pills, tablets, film tablets, coated tablets, capsules, powders and deposits.

Forms other than oral administrable forms are also possible. The compounds of the present invention and/or pharmaceutical preparations containing said compounds may be administered by any appropriate means, including but not limited to injection (intravenous, intraperitoneal, intramuscular, subcutaneous) by absorption through epithelial or mucocutaneous linings (oral mucosa, rectal and vaginal epithelial linings, nasopharyngial mucosa, intestinal mucosa); orally, rectally, transdermally, topically, intradermally, intragastrally, intracutanly, intravaginally, intravasally, intranasally, intrabuccally, percutanly, sublingually, or any other means available within the pharmaceutical arts.

The pharmaceutical compositions of the present invention, containing at least one compound of the present invention or pharmaceutically acceptable salts thereof as an active ingredient, will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral nontoxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture.

Pharmaceutical compositions may be comprised of from about 5 to about 95 percent by weight of the active ingredient, which range includes all values and subranges therebetween, including 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 90.5, 91, 91.5, 92, 92.5, 93, 93.5, 94, 94.5, and 95% by weight.

Suitable binders include starch, gelatin, natural sugars, corn sweeteners, natural and synthetic gums such as acacia, sodium alginate, carboxymethyl-cellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compounds or compositions of the present invention may be formulated in sustained release form to provide the rate controlled release of any one or more of the components or active ingredients to optimize the therapeutic effects, i.e. antihistaminic activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water, ethanolic, water-ethanol or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the present invention may also be deliverable transdermally. The transdermal compositions may take the form of creams, lotions, aerosols and/or emulsions and can be included in a transdermal patch of the matrix or reservoir type as are conventional in the art for this purpose.

The term capsule refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet means compressed or molded solid dosage form containing the active ingredients with suitable diluents. The tablet can be prepared by compression of mixtures or granulations obtained by wet granulation, dry granulation or by compaction well known to a person skilled in the art.

Oral gels refers to the active ingredients dispersed or solubilized in a hydrophillic semi-solid matrix.

Powders for constitution refers to powder blends containing the active ingredients and suitable diluents which can be suspended in water or juices.

Suitable diluents are substances that usually make up the major portion of the composition or dosage form.

Suitable diluents include sugars such as lactose, sucrose, mannitol and sorbitol, starches derived from wheat, corn rice and potato, and celluloses such as microcrystalline cellulose. The amount of diluent in the composition can range from about 5 to about 95% by weight of the total composition, preferably from about 25 to about 75%, more preferably from about 30 to about 60% by weight.

The term disintegrants refers to materials added to the composition to help it break apart (disintegrate) and release the medicaments. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses and cross-linked microcrystalline celluloses such as sodium croscarmellose, alginates such as alginic acid and sodium alginate, clays such as bentonites, and effervescent mixtures. The amount of disintegrant in the composition can range from about 2 to about 20% by weight of the composition, more preferably from about 5 to about 10% by weight.

Binders characterize substances that bind or "glue" powders together and make them cohesive by forming granules, thus serving as the "adhesive" in the formulation. Binders add cohesive strength already available in the diluent or bulking agent. Suitable binders include sugars such as sucrose, starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropyl-methylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d,l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents are materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents are excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Techniques for the formulation and administration of the compounds of the present invention may be found in "Remington's Pharmaceutical Sciences" Mack Publishing Co., Easton Pa., the entire contents of which are hereby incorporated by reference. A suitable composition comprising at least one compound of the invention may be a solution of the compound in a suitable liquid pharmaceutical carrier or any other formulation such as tablets, pills, film tablets, coated tablets, dragees, capsules, powders and deposits, gels, syrups, slurries, suspensions, emulsions, and the like.

The term "treating and/or preventing" as used herein refers to reversing, alleviating, inhibiting the progress of, or preventing the disorder or condition to which the term applies, or one or more symptoms of the disorder or condition. The term "treatment" as used herein refers to the act of treating and/or preventing as the term is defined above. Preferably, the treated or administered subject is a human subject and more preferably a human subject in need of treatment.

The terms, "effective amount" or "therapeutically effective amount" means an amount sufficient to cause any observable or measurable difference and preferably improvement in a subject's condition or indication, and preferably that condition or indication sought to be treated.

Accession numbers for murine anti-MIF antibodies are given below:
for the III.D.9 mAb: HB-12220
for the XIV.15.5 mAb: HB-12221.

Preferably, an "acute" condition, e.g. acute myocardial infarction, is distinguished from a "chronic" condition, e.g., chronic congestive heart failure.

When used herein, the term, "antibody" suitably includes antibody-derived fragment(s), Fab, Fab fragment(s), $Fab_2$, CDR-derived regions, antibody-derived peptides, and/or single chain antibodies) as is known to those of ordinary skill in this art. Fab is preferred.

When used herein, the term, "cardiac dysfunction" may suitably include one or more indications selected from the group including cardiac dysfunction, irregularity in myocardial activity, depression in myocardial activity, burn-injury associated cardiac dysfunction, cardiac dysfunction following acute myocardial infarction, cardiodepression, and a combination thereof. These terms are understood by a physician of ordinary skill in this art.

Other embodiments of the present invention are given below.

A. A method for treating and/or preventing burn injury-associated cardiodepression and/or cardiac dysfunction in a subject, which includes:
administering to the subject an effective amount of at least one anti-MIF antibody.

B. A method for treating and/or preventing burn injury-associated cardiac dysfunction in a subject, which includes:
administering to the subject an effective amount of at least one anti-MIF antibody,
wherein the burn injury-associated cardiac dysfunction includes irregularity in myocardial activity or depression in myocardial activity or both.

C. A method for treating and/or preventing burn injury-associated cardiac dysfunction in a subject, which includes:
administering to the subject an effective amount of a composition comprising an MIF inhibitor,
wherein the MIF inhibitor includes at least one anti-MIF antibody.

D. A method for treating and/or preventing burn injury-associated cardiac dysfunction in a subject, which includes:
administering to the subject an effective amount of a composition that includes at least one MIF inhibitor,
wherein the MIF inhibitor includes at least one anti-MIF antibody, and wherein the antibody is a monoclonal antibody.

E. A method for treating and/or preventing burn injury-associated cardiac dysfunction in a subject, which includes:
administering to the subject an effective amount of a composition that includes at least one MIF inhibitor,
wherein the MIF inhibitor includes at least one anti-MIF monoclonal humanized antibody.

F. A method for treating and/or preventing burn injury-associated cardiac dysfunction in a subject, which includes:
administering to the subject an effective amount of a composition that includes at least one MIF inhibitor, wherein the composition is administered via at least one route selected from the group including intramuscular injection, intraperitoneal injection, subcutaneous injection, intravascular injection, and a combination thereof.

G. A pharmaceutical composition for the treatment and prevention of burn injury-associated cardiac dysfunction in a subject, which includes:
at least one anti-MIF antibody; and
at least one pharmaceutically acceptable carrier.

H. A pharmaceutical composition for the treatment and prevention of burn injury-associated cardiac dysfunction in a subject, which includes:
at least one MIF inhibitor; and
at least one pharmaceutically acceptable carrier wherein said MIF inhibitor includes at least one anti-MIF antibody.

I. A method for treating and/or preventing cardiodepression and/or cardiac dysfunction in a subject, the method including:
administering to the subject an effective amount of a composition that includes at least one anti-CD74 antibody.

J. A method for treating and/or preventing cardiodepression and/or cardiac dysfunction in a subject, the method including:
administering to the subject an effective amount of a composition that includes at least one anti-CD74 antibody, wherein the cardiac dysfunction and/or cardiodepression includes irregularity in myocardial activity or depression in myocardial activity, or both.

K. A method for treating and/or preventing cardiac dysfunction in a subject, the method including:
administering to the subject an effective amount of at least one anti-CD74 antibody, wherein the cardiac dysfunction includes at least one burn injury-associated cardiac dysfunction.

L. A method for treating and/or preventing cardiac dysfunction in a subject, the method including:
administering to the subject an effective amount of a composition that includes at least one CD74 inhibitor, wherein the CD74 inhibitor includes at least one anti-CD74 antibody.

M. A method for treating and/or preventing cardiac dysfunction and/or cardiodepression in a subject, the method including:
administering to the subject an effective amount of a composition that includes at least one CD74 inhibitor, wherein the CD74 inhibitor includes at least one anti-CD74 monoclonal antibody.

N. A method for treating and/or preventing cardiac dysfunction in a subject, the method including:
administering to the subject an effective amount of a composition that includes at least one CD74 inhibitor, wherein the CD74 inhibitor includes at least one anti-CD74 monoclonal humanized antibody.

O. A method for treating and/or preventing cardiac dysfunction in a subject, the method including:
administering to the subject an effective amount of a composition that includes at least one anti-CD74 antibody, wherein the composition is administered via at least one route selected from the group including intramuscular injection, intraperitoneal injection, subcutaneous injection, intravascular injection, and a combination thereof.

P. A pharmaceutical composition for the treatment and prevention of cardiac dysfunction and/or cardiodepression in a subject, which includes:
at least one anti-CD74 antibody; and
at least one pharmaceutically acceptable carrier.

Q. A pharmaceutical composition for the treatment and prevention of cardiac dysfunction in a subject, which includes:
at least one CD74 inhibitor; and
at least one pharmaceutically acceptable carrier,
wherein the CD74 inhibitor includes at least one anti-CD74 antibody.

R. A method for improving cardiac function in a subject following acute myocardial infarction, the method including:
administering to the subject an effective amount of a composition that includes at least one anti-MIF antibody.

S. A method for improving cardiac function in a subject following acute myocardial infarction, the method including:
administering to the subject an effective amount of at least one MIF inhibitor,
wherein the MIF inhibitor includes at least one anti-MIF antibody.

T. A method for improving cardiac function in a subject following acute myocardial infarction, the method including:
administering to the subject an effective amount of at least one MIF inhibitor,
wherein the MIF inhibitor includes at least one anti-MIF monoclonal antibody.

U. A method for improving cardiac function in a subject following acute myocardial infarction, the method including:
administering to the subject an effective amount of at least one MIF inhibitor,
wherein the MIF inhibitor includes at least one anti-MIF monoclonal humanized antibody.

V. A method for improving cardiac function in a subject following acute myocardial infarction, the method including:

administering to the subject an effective amount of at least one anti-MIF antibody and at least one anti-CD74 antibody.

W. A method for improving cardiac function in a subject following acute myocardial infarction, the method including:
administering to the subject an effective amount of a composition that includes at least one MIF inhibitor and at least one CD74 inhibitor, wherein said CD74 inhibitor includes at least one anti-CD74 antibody.

X. A method for improving cardiac function in a subject following acute myocardial infarction, the method including:
administering to the subject an effective amount of a composition that includes at least one MIF inhibitor and at least one CD74 inhibitor, wherein the CD74 inhibitor includes at least one anti-CD74 monoclonal antibody.

Y. A method for improving cardiac function in a subject following acute myocardial infarction, the method including:
administering to the subject an effective amount of a composition that includes at least one MIF inhibitor and at least one CD74 inhibitor, and wherein the CD74 inhibitor includes at least one anti-CD74 monoclonal humanized antibody.

Z. A method for improving cardiac function in a subject following acute myocardial infarction, the method including:
administering to the subject an effective amount of a composition that includes at least one anti-MIF antibody,
wherein the composition is administered via at least one route selected from
the group including intramuscular injection, intraperitoneal injection, subcutaneous injection, intravascular injection, and a combination thereof.

AA. A pharmaceutical composition for the treatment and prevention of cardiac dysfunction and/or cardiodepression in a subject, including:
at least one anti-MIF antibody; and
at least one pharmaceutically acceptable carrier.

BB. A pharmaceutical composition for the treatment and prevention of cardiac dysfunction and/or cardiodepression in a subject, including:
at least one anti-MIF antibody;
at least one anti-CD74 antibody; and
at least one pharmaceutically acceptable carrier.

CC. A method for treating and/or preventing cardiac dysfunction in a subject following acute myocardial infarction, the method including:
administering to the subject an effective amount of at least one anti-TNFR antibody and at least one anti-MIF antibody.

DD. A method for treating and/or preventing cardiac dysfunction in a subject following acute myocardial infarction, the method including:
administering to the subject an effective amount of a composition that includes at least one TNFR inhibitor and at least one MIF inhibitor,
wherein the TNFR inhibitor includes at least one anti-TNFR antibody and wherein the MIF inhibitor includes at least one anti-MIF antibody.

EE. A method for treating and/or preventing cardiac dysfunction in a subject following acute myocardial infarction, the method including:
administering to the subject an effective amount of a composition that includes at least one TNFR inhibitor and at least one MIF inhibitor,
wherein the TNFR inhibitor includes at least one anti-TNFR antibody and wherein the MIF inhibitor includes at least one anti-MIF antibody,
wherein the anti-TNFR antibody includes at least one monoclonal antibody.

FF. A method for treating and/or preventing cardiac dysfunction in a subject following acute myocardial infarction, the method including:
administering to the subject an effective amount of a composition that includes at least one TNFR inhibitor and at least one MIF inhibitor,
wherein the TNFR inhibitor includes at least one anti-TNFR antibody and wherein the MIF inhibitor includes at least one anti-MIF antibody,
and wherein the anti-TNFR antibody includes at least one monoclonal humanized antibody.

GG. A method for treating and/or preventing cardiac dysfunction in a subject following acute myocardial infarction, the method including:
administering to the subject an effective amount of a composition that includes at least one TNFR inhibitor and at least one MIF inhibitor,
wherein the TNFR inhibitor includes at least one anti-TNFR antibody and wherein the MIF inhibitor includes at least one anti-MIF monoclonal antibody.

HH. A method for treating and/or preventing cardiac dysfunction in a subject following acute myocardial infarction, the method including:
administering to the subject an effective amount of a composition that includes at least one TNFR inhibitor and at least one MIF inhibitor,
wherein the TNFR inhibitor includes at least one anti-TNFR antibody and wherein the MIF inhibitor includes at least one anti-MIF monoclonal humanized antibody.

II. A method for treating and/or preventing cardiac dysfunction in a subject following acute myocardial infarction, the method including:
administering to the subject an effective amount of a composition that includes at least one TNFR inhibitor and at least one MIF inhibitor,
wherein the TNFR inhibitor includes at least one anti-TNFR monoclonal humanized antibody and wherein the MIF inhibitor includes at least one anti-MIF monoclonal humanized antibody.

JJ. A pharmaceutical composition for the treatment and prevention of cardiac dysfunction and/or cardiodepression in a subject, including:
at least one anti-TNFR antibody;
at least one anti-MIF antibody.

KK. A pharmaceutical composition for the treatment and prevention of cardiac dysfunction in a subject, including:
at least one TNFR inhibitor;
at least one MIF inhibitor; and
at least one pharmaceutically acceptable carrier;
wherein the TNFR inhibitor includes at least one anti-TNFR antibody.

LL. A pharmaceutical composition for the treatment and prevention of cardiac dysfunction in a subject, including:
at least one TNFR inhibitor;
at least one MIF inhibitor; and
at least one pharmaceutically acceptable carrier;
wherein the MIF inhibitor includes at least one anti-MIF antibody.

MM. A pharmaceutical composition for the treatment and prevention of cardiac dysfunction in a subject, including:
at least one TNFR inhibitor;
at least one MIF inhibitor; and
at least one pharmaceutically acceptable carrier;
wherein the TNFR inhibitor includes at least one anti-TNFR antibody and wherein the MIF inhibitor includes at least one anti-MIF antibody.

NN. A pharmaceutical composition for the treatment and prevention of cardiac dysfunction in a subject, including:
- at least one TNFR inhibitor;
- at least one MIF inhibitor; and
- at least one pharmaceutically acceptable carrier;
- wherein the TNFR inhibitor includes at least one anti-TNFR monoclonal antibody and wherein the MIF inhibitor includes at least one anti-MIF monoclonal antibody.

OO. A pharmaceutical composition for the treatment and prevention of cardiac dysfunction in a subject, including:
- at least one TNFR inhibitor;
- at least one MIF inhibitor; and
- at least one pharmaceutically acceptable carrier;
- wherein the TNFR inhibitor includes at least one anti-TNFR monoclonal humanized antibody and wherein the MIF inhibitor includes at least one anti-MIF monoclonal humanized antibody.

PP. A method for treating and/or preventing cardiac dysfunction in a subject, the method including:
- administering to the subject an effective amount of at least one anti-MIF antibody.

QQ. A method for treating and/or preventing cardiac dysfunction in a subject, the method including:
- administering to the subject an effective amount of a composition that includes at least one anti-MIF antibody,
- wherein the cardiac dysfunction includes at least one selected from the group including irregularity in myocardial activity, depression in myocardial activity, and a combination thereof.

RR. A method for treating and/or preventing cardiac dysfunction and/or cardiodepression in a subject, the method including:
- administering to the subject an effective amount of a composition that includes at least one MIF inhibitor,
- wherein the MIF inhibitor includes at least one anti-MIF antibody.

SS. A method for treating and/or preventing cardiac dysfunction in a subject, the method including:
- administering to the subject an effective amount of a composition that includes at least one MIF inhibitor,
- wherein the MIF inhibitor includes at least one anti-MIF monoclonal antibody.

TT. A method for treating and/or preventing cardiac dysfunction in a subject, the method including:
- administering to the subject an effective amount of a composition that includes at least one MIF inhibitor,
- wherein the MIF inhibitor includes at least one anti-MIF humanized antibody.

UU. A pharmaceutical composition, that includes:
- a therapeutically effective amount of at least one anti-MIF antibody; and
- at least one pharmaceutically acceptable carrier.

VV. A pharmaceutical composition, which includes:
- at least one MIF inhibitor; and
- at least one pharmaceutically acceptable carrier,
- wherein the MIF inhibitor includes at least one anti-MIF antibody.

WW. A method for identifying an MIF inhibitor, the method including:
- exposing at lease one myocyte to MIF;
- determining at least one MIF-related myocyte activity;
- exposing the myocyte to at least one MIF and at least one candidate agent;
- determining at least one MIF-related myocyte activity in the presence of the candidate agent; and
- determining whether the candidate agent affects the MIF-related myocyte activity.

XX. A method for identifying an MIF inhibitor, the method including:
- exposing at lease one myocyte to MIF;
- determining at least one MIF-related myocyte activity;
- exposing the myocyte to at least one MIF and at least one candidate agent;
- determining at least one MIF-related myocyte activity in the presence of the candidate agent; and
- determining whether the candidate agent affects the MIF-related myocyte activity,
- wherein the MIF-related myocyte activity is determined by immunochemistry.

YY. A method for identifying an MIF inhibitor, the method including:
- exposing at lease one myocyte to MIF;
- determining at least one MIF-related myocyte activity;
- exposing the myocyte to at least one MIF and at least one candidate agent;
- determining at least one MIF-related myocyte activity in the presence of the candidate agent; and
- determining whether the candidate agent affects the MIF-related myocyte activity,
- wherein the MIF-related myocyte activity is determined by Langendorff assay.

ZZ A method for identifying an MIF inhibitor, the method including:
- exposing at lease one myocyte to MIF;
- determining at least one MIF-related myocyte activity;
- exposing the myocyte to at least one MIF and at least one candidate agent;
- determining at least one MIF-related myocyte activity in the presence of the candidate agent; and
- determining whether the candidate agent affects the MIF-related myocyte activity,
- wherein the related myocyte activity is determined by echocardiography.

AAA. A method for at least one selected from the group including treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, and a combination thereof, which includes:
- administering to the subject an effective amount of at least one small molecule MIF inhibitor and/or salt thereof.

BBB. A method for at least one selected from the group including treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, and a combination thereof, which includes:
- administering to the subject an effective amount of a composition that includes:
- at least one small molecule MIF inhibitor and/or salt thereof; and
- at least one pharmaceutically acceptable carrier.

CCC. A method for treating and/or preventing burn injury-associated cardiodepression and/or cardiac dysfunction in a subject, which includes:
 administering to the subject an effective amount of at least one small molecule MIF inhibitor and/or salt thereof.

DDD. A method for treating and/or preventing burn injury-associated cardiac dysfunction in a subject, which includes:
 administering to the subject an effective amount of at least one small molecule MIF inhibitor and/or salt thereof,
 wherein the burn injury-associated cardiac dysfunction includes irregularity in myocardial activity or depression in myocardial activity or both.

EEE. A method for treating and/or preventing burn injury-associated cardiac dysfunction in a subject, which includes:
 administering to the subject an effective amount of a composition that includes at least one small molecule MIF inhibitor and/or salt thereof.

FFF. A method for treating and/or preventing burn injury-associated cardiac dysfunction in a subject, which includes:
 administering to the subject an effective amount of a composition that includes at least one small molecule MIF inhibitor and/or salt thereof, wherein the composition is administered via at least one route selected from the group including intramuscular injection, intraperitoneal injection, subcutaneous injection, intravascular injection, and a combination thereof.

GGG. A pharmaceutical composition for the treatment and prevention of burn injury-associated cardiac dysfunction in a subject, which includes:
 at least one small molecule MIF inhibitor and/or salt thereof; and
 at least one pharmaceutically acceptable carrier.

HHH. A method for improving cardiac function in a subject following acute myocardial infarction, the method including:
 administering to the subject an effective amount of at least one small molecule MIF inhibitor and/or salt thereof.

III. A method for improving cardiac function in a subject following acute myocardial infarction, the method including:
 administering to the subject an effective amount of a composition that includes at least one small molecule MIF inhibitor and/or salt thereof,
 wherein the composition is administered via at least one route selected from the group including intramuscular injection, intraperitoneal injection, subcutaneous injection, intravascular injection, and a combination thereof.

JJJ. A method for treating and/or preventing cardiac dysfunction in a subject following acute myocardial infarction, the method including:
 administering to the subject an effective amount of a composition that includes at least one small molecule MIF inhibitor and/or salt thereof.

KKK. A pharmaceutical composition effective for at least one selected from the group including treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, and a combination thereof, which includes an effective amount of a combination that includes:
 at least one anti-TNFR antibody;
 at least one anti-MIF antibody; and
 at least one pharmaceutically acceptable carrier.

LLL. A pharmaceutical composition effective for at least one selected from the group including treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, and a combination thereof, which includes an effective amount of a combination that includes:
 at least one anti-CD-74 antibody;
 at least one anti-MIF antibody; and
 at least one pharmaceutically acceptable carrier.

MMM. A method for at least one selected from the group including treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, and a combination thereof, which includes administering to the subject an effective amount of a combination that includes:
 at least one anti-TNFR antibody;
 at least one anti-MIF antibody; and
 at least one pharmaceutically acceptable carrier.

NNN. A method for at least one selected from the group including treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, and a combination thereof, which includes administering to the subject an effective amount of a combination that includes:
 at least one anti-CD-74 antibody;
 at least one anti-MIF antibody; and
 at least one pharmaceutically acceptable carrier.

OOO. Another embodiment of the invention relates to administering an effective amount of one or more of the soluble MIF receptor and/or MIF receptor antagonist (optionally in a pharmaceutically acceptable carrier) to a subject in need thereof for at least one selected from the group including treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, and a combination thereof.

PPP. Another embodiment of the invention relates to administering an effective amount of one or more of the following, in any combination:

small molecule MIF inhibitor;
    soluble MIF receptor;
    MIF receptor antagonist;
    anti-CD74 antibody;
    anti-MIF antibody;
    anti-TNFR antibody; and
    optionally, a pharmaceutically acceptable carrier
    to a subject in need thereof for at least one selected from the group including treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, and a combination thereof.

QQQ. Another embodiment of the invention relates to a composition, that includes an effective amount of one or more of the following, in any combination:

small molecule MIF inhibitor;
    soluble MIF receptor;
    MIF receptor antagonist;
    anti-CD74 antibody;
    anti-MIF antibody;
    anti-TNFR antibody; and
    optionally, a pharmaceutically acceptable carrier
    wherein the composition is effective for at least one selected from the group including treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, and a combination thereof.

RRR. Another embodiment of the invention relates to administering an effective amount of anti-TNFR antibody; and optionally, a pharmaceutically acceptable carrier
to a subject in need thereof for at least one selected from the group including treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, and a combination thereof.

SSS. Another embodiment of the invention relates to a composition that includes an effective amount of anti-TNFR antibody; and optionally, a pharmaceutically acceptable carrier
    wherein the composition is effective for at least one selected from the group including treating and/or preventing cardiac dysfunction in a subject in need thereof, treating and/or preventing irregularity in myocardial activity in a subject in need thereof, treating and/or preventing depression in myocardial activity in a subject in need thereof, treating and/or preventing burn-injury associated cardiac dysfunction in a subject in need thereof, treating and/or preventing cardiac dysfunction following acute myocardial infarction in a subject in need thereof, treating and/or preventing cardiodepression in a subject in need thereof, and a combination thereof.

EXAMPLES

Having generally described this invention, a further understanding can be obtained by certain specific examples, which are provided herein for purposes of illustration only, and are not intended to be limiting unless otherwise specified.

Example 1

Antibodies and cytokines. Goat anti-hMIF IgG and rhMIF (R&D Systems, Minneapolis, Minn.) were reconstituted in PBS and 0.1% BSA in PBS respectively, aliquoted, and stored at −20° C. until use. Rabbit anti-goat IgG-HRP (BioRad Corp., Hercules, Calif.) stored at 4° C. until use.

Animals and Experimental Vesign. C57BL/6J and C3H/HeJ mice were obtained at 6-10 weeks of age (Jackson Labs, Bar Harbor, Me.). Adult Sprague-Dawley rats (Harlan Laboratories, Houston, Tex.) weighing 325-360 g were used in this study. Commercial chow and tap water were made available ad libitum. All animal protocols were reviewed and approved by the University of Texas Southwestern Medical Center Institutional Animal Care Advisory Committee and were in compliance with the rules governing animal use as published by the NIH. C57BL/6J mice were injected i.p. with 4 mg/kg $E.\ coli$ 0111:B4 LPS (Sigma-Aldrich Corp., St. Louis, Mo.) and sacrificed post injection at time points indicated in the text by $cO2$ asphyxiation and subsequent cervical dislocation. Uninjected mice were used as controls. Two anti-MIF antibodies (III.D.9 and XIV.15.5, Rockland Immunochemicals, Inc., Gilbertsville, Pa.) and their isotype control (HB-49, Rockland Immunochemicals, Inc., Gilbertsville, Pa.) were injected (100 µg in 200 µl PBS) i.p. 90 m before the LPS challenge in the echocardiogram studies. Whole hearts were removed and snap frozen in liquid nitrogen and stored at −80° C. or fixed in 10% neutral-buffered formalin for 24 h and placed in 70% ethanol for immunohistochemistry.

Example 2

Protein Extraction and Western Blotting. Hearts were thawed and homogenized on ice in Tris-Buffered Saline (TBS, 50 mM Tris, 150 mM NaCl, pH 7.5) containing 1% NP40, 0.5% deoxycholic acid, 0.1% SDS, 2 mM EDTA, and 1 mM PMSF. Lysate concentration was quantified using the Bio-Rad Protein Assay (Hercules, Calif.). Protein (20 µg) was diluted 1:1 with Laemmli sample buffer (Bio-Rad, Hercules, Calif.) and resolved on an 18% SDS polyacrylamide gels under reducing conditions. The gel was transferred to PVDF membranes (NEN, Boston, Mass.) using a semi-dry transfer apparatus (Bio-Rad, Hercules, Calif.) at 15 V for 15 m. Membranes were blocked with TBS/0.1% Tween-20 (TBS-T) with 0.5% nonfat dry milk for 30 in and incubated with goat anti-hMIF IgG (1:750) in TBS/0.1% Tween-20/5% nonfat milk overnight at 4° C. The membranes were washed 3 times for 10 m in TBS-T, incubated with rabbit anti-goat IgG-HRP (1:1000) for 1 h at RT, and washed 4 times for 10 m with TBS-T. The membranes were exposed to 5 ml of a mixture of luminol plus hydrogen peroxide under alkaline conditions (SuperSignal West Pico, Pierce, Rockford, Ill.) for 5 min and the resulting chemiluminescent reaction was detected by Kodak X-OMAT AR Film (Eastman Kodak Co., Rochester, N.Y.).

Example 3

RNA Extraction, probe preparation and Northern Blotting. Total RNA was extracted with Trizol (Invitrogen, Carlsbad, Calif.) from hearts thawed on ice according to the manufacturer's protocol and quantified by spectrophotometry. A MIF specific Northern probe was prepared by isolating DNA (DNeasy Tissue Kit, Qiagen, Valencia, Calif.) from the MIF plasmid (Research Genetics, Huntsville, Ala.) and subsequently cutting it with ECOR1 and NOT I restriction enzymes (Fisher Scientific, Pittsburgh, Pa.). The resultant DNA was resolved on a 1.2% agarose gel, purified (GenElute Agarose Spin Columns, Supelco, Bellefonte, Pa.), labeled with 5 µl $^{32}$p-dCTP (3000 Ci/mmol) (PerkinElmer, Boston, Mass.) using Ready-To-Go Labeling Beads (Amersham Pharmacia, Piscatany, N.J.), and purified in ProbeQuant Microcolumns (Amersham Pharmacia, Piscatany, N.J.) according to manufacturer's protocols.

mRNA (10 µg) was resolved on 1.2% agarose gels at 100 V for 1 h and transferred to Hybond-N+ membranes (Amersham Pharmacia, Buckingham, England) at 100 V for 1 h on a transfer electrophoresis unit (TransPhor PowerLid, Hoefer Scientific Instruments, San Francisco). RNA was linked to the membranes for 2 m using a GS Gene Linker (Bio-Rad, Hercules, Calif.). Membranes were prehybridized in Perfect-Hyb Plus (Sigma, St. Louis, Mo.) for 4-5 h at 42° C. and then incubated with $^{32}$P labeled MIF DNA probe at 42° C. overnight. The membranes were washed twice for 30 m in 2×SSC/0.1% SDS at 46° C., and washed twice for 30 m in 0.2×SSC/0.1% SDS at 46° C., and detected by Kodak X-OMAT AR Film (Eastman Kodak Co., Rochester, N.Y.). The same membranes were then probed with radiolabeled β-actin to ensure equal loading of protein.

Example 4

Immunohistochemistry. Tissue was fixed in neutral buffered formalin and processed to paraffin and subsequently immunostained at RT on a BioTek Solutions Techmate™ 1000 automated immunostainer (Ventana Medical Systems, Tucson, Ariz.) using the Ultra-streptavidin biotin system with horseradish peroxidase and diaminobenzidine (DAB) chromogen (Signet Laboratories, Dedham, Mass.). Optimum primary antibody dilutions were predetermined using known positive control tissues (rat post-LPS challenge). Paraffin sections were cut at 3 µm on a rotary microtome, mounted on positively charged glass slides (POP 100 capillary gap slides, Ventana Medical Systems, Tucson, Ariz.) and air-dried overnight. Sections were then deparaffinized in xylene and ethanol, quenched with fresh 3% hydrogen peroxide for 10 m to inhibit endogenous tissue peroxidase activity, and rinsed with deionized water. Sections were incubated in unlabeled blocking serum for 15 m to block nonspecific binding of the secondary antibody and then incubated for 25 m with either rabbit anti-MIF (1:400, Torrey Pines BioLabs, Inc., Houston, Tex.) diluted in 1% citrate buffer (BioPath, Oklahoma City, Okla.), or with buffer alone as a negative reagent control. Following washes in buffer, sections were incubated for 25 in with a biotinylated polyvalent secondary antibody solution (containing goat anti-rabbit immunoglobulins). Next, sections were washed with buffer, incubated in horseradish peroxidase-conjugated streptavidin-biotin complex for 15 in, washed again in buffer, and then incubated with 2 changes, 5 in each, of a freshly prepared mixture of DAB and $H_2O_2$ in buffer, followed by washing in buffer and then water. Sections were then counterstained with hematoxylin, dehydrated in a graded series of ethanol and xylene, and coverslipped. Slides were reviewed by light microscopy and positive reactions with DAB were identified as a dark brown reaction product.

Example 5

Determination of cardiac function in response to rMIF. C57BL/6J and C3H/HeJ mice were used in the Langendorff assays. Briefly, 200 U heparin sulfate was given i.p., the mice sacrificed 20 m later, and the heart immediately removed and placed on ice in Krebs-Hanseleit Buffer (2 mM $NaHCO_3$, 118 mM NaCl, 4.7 mM KCL, 1.2 mM KH2PO$_4$, 1.2 mM $MgSO_4$, 2.5 mM $CaCl_2$, 11.1 mM glucose, pH 7.4, which was prepared fresh with demineralized, deionized water and bubbled with 95% $O_2$ and 5% $CO_2$ ($pO_2$ 590 mmHg, $pCO_2$ 38 mmHg)). The aorta was cannulated with PE50 tubing, the heart perfused in a retrograde manner through the aortic root with prefiltered, oxygenated Krebs-Hanseleit Buffer at a constant flow rate of 1.5 ml/m (T 37° C.) and a recirculating volume of 100 ml. The heart was placed in a water-jacketed chamber to maintain constant temperature and humidity. PE60 intratnedic polyethylene tubing was connected to a Statham pressure transducer inserted into the left ventricle (LV) to measure LV pressure. Temperature was monitored using a 27G thertnistor needle inserted into the LV muscle. After instrumentation, hearts were allowed to stabilize for 10 m and hearts that failed to achieve a stable pressure or developed persistent arrhythmias during this time were excluded from the study. Following stabilization, LV pressure and its first derivative (dP/dt), heart rate, and coronary perfusion were measured simultaneously with a multichannel Grass 7D polygraph (Grass Instruments, Quincy, Mass.). Cardiac function for all hearts was determined by plotting peak systolic LV pressure and±dP/dt,Ia, values against changes in coronary flow rate. Hearts were perfused with or without 20 ng/ml RMIF added to the perfusate.

Example 6

Determination of cardiac dysfunction by echocardiography Echocardiograms to assess systolic function were performed using M-mode measurements. Mice were anesthestized with 5% isofluorane with 2.5 L/m $O_2$ for 20 seconds (until unconscience) followed by 2% isofluorane and $O_2$ for an average of 12-15 m. Hair was removed from the thorax and upper abdomen using Nair® hair remover after sitting for 3 m using gauze. Echocardiography measurements were obtained on anesthetized mice approximately 5-8 m after induction to allow any transient cardiac depression to pass. These transient, minimal changes in cardiac function detected by echocardiography have been reported using inhaled isofluorane, although FS (%) has been reported to be stable. Cardiac echocardiography was performed using a Hewlett-Packard Sonos 5500 (Agilent Technologies; Edmonton, Alberta, Canada) with a frame rate of 300-500 frames/s in a random and blinded manner. A 12 MHz linear transducer was placed on the left hemithorax interfaced with a layer of US transmission gel (Aquasonic 100, Parker Laboratories; Fairfield, N.J.). The two dimensional parastemal short-axis imaging plane guided LV M-mode tracings close to the papillary muscle level. Depth was set at a minimum of 2 cm with a sweep speed of 150 m/s. Tracings were printed on a Sony color printer (UP-5200, Sony).

Example 7

M-mode measurements. Data represented the average of at least two separate scans, each of which represent the average of at least three selected beats. End diastole was defined as the maximal LV diastolic dimension, and end systole was defined as the peak of posterior wall motion. Systolic function was calculated from LV dimensions as fractional shortening (FS) as follows: FS (%): LVED-LVES/LVED×100, as shown in FIG. 5A.

Example 8

Statistical Analysis. Northern and Western data are expressed as mean±standard error and statistically analyzed using a One Way Analysis of Variance. Determination of significance between experimental and control groups was performed using the Tukey method (p≤0.05). Cardiac function determined by the Langendorff preparation is expressed as mean±standard error and separate analyses were performed for each of LVP, +dP/dt$_{max}$, and −dP/dt$_{max}$, as a function of treatment group and coronary flow rate using a Repeated Measures Analysis of Variance. A multiple comparison procedure employing the Bonferroni method was used to determine significant differences between groups (p<0.05). Cardiac function determined by echocardiogram is expressed by fractional shortening % (LVED-LVES/LVEP× 100.)±standard deviation and analyzed using a One Way Repeated Measures Analysis of Variance. Additional comparisons were performed using the Tukey Test to determine significant differences between specific groups (p<0.05). All statistical analyses were performed using SigmaStat 2.03 (SPSS Inc., Chicago, Ill.) and Microsoft Excel (Microsoft Corp., Seattle, Wash.).

Example 9

Figure 2:
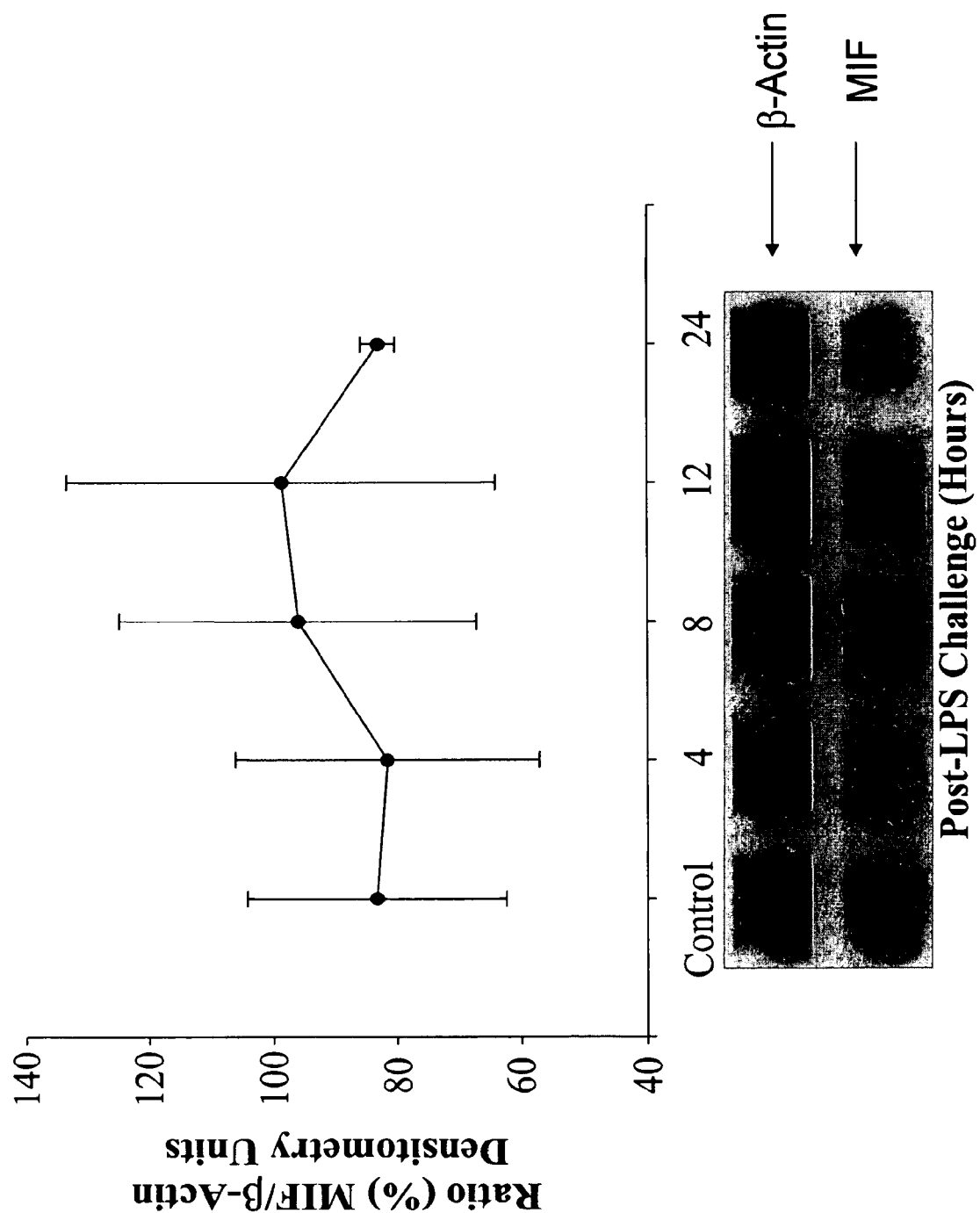
FIG. 2: LPS challenge does not upregulate MIF mRNA in cardiac tissue. Each data point in the graph is the mean (+/−standard error) of 3 independent Northern blot experiments. A representative Northern blot is shown below the graph. No significant differences between time points were identified ($p>0.05$).

MIF protein is constituitively expressed by cardiac myocytes in vivo and is released in response to LPS Challenge. Both immunochemistry and Western analysis performed on cardiac tissue documented the presence of MIF in cardiac cells, including ventricular and atrial myocytes, under baseline control conditions (FIGS. 1 and 2). Following endotoxin challenge, both immunochemistry and immunoblot analysis document a significant decrease in cardiac tissue MIF following endotoxin. This decrease was most profound (75% decrease) at 12 h, but returned to near baseline control levels by 24 h. This expression pattern in the heart is similar to that witnessed in the liver and spleen (FIG. 2), and consistent with the hypothesis that MIF is released from preformed stores within tissue following LPS challenge. The release of MIF from tissue is evident at 4 hours on immunoblot (FIG. 1) correlates with the increase in serum levels following endotoxin exposure (Table 1).

TABLE 1

Serum Levels of MIF Following a 4 mg/kg Endotoxin Challenge. 3 mice/group; perform statistics (One Way ANOVA)

| Baseline | 4 hours | 8 hours | 12 hours | 24 hours | 48 hours |
|---|---|---|---|---|---|
| 79.1 ± 4.6 | 90.9 ± 8.7 | 118.1 ± 5.6* | 81.4 ± 5.8 | 70.1 ± 5.1 | 69.9 ± 9.0 |

Example 10

Figure 3:
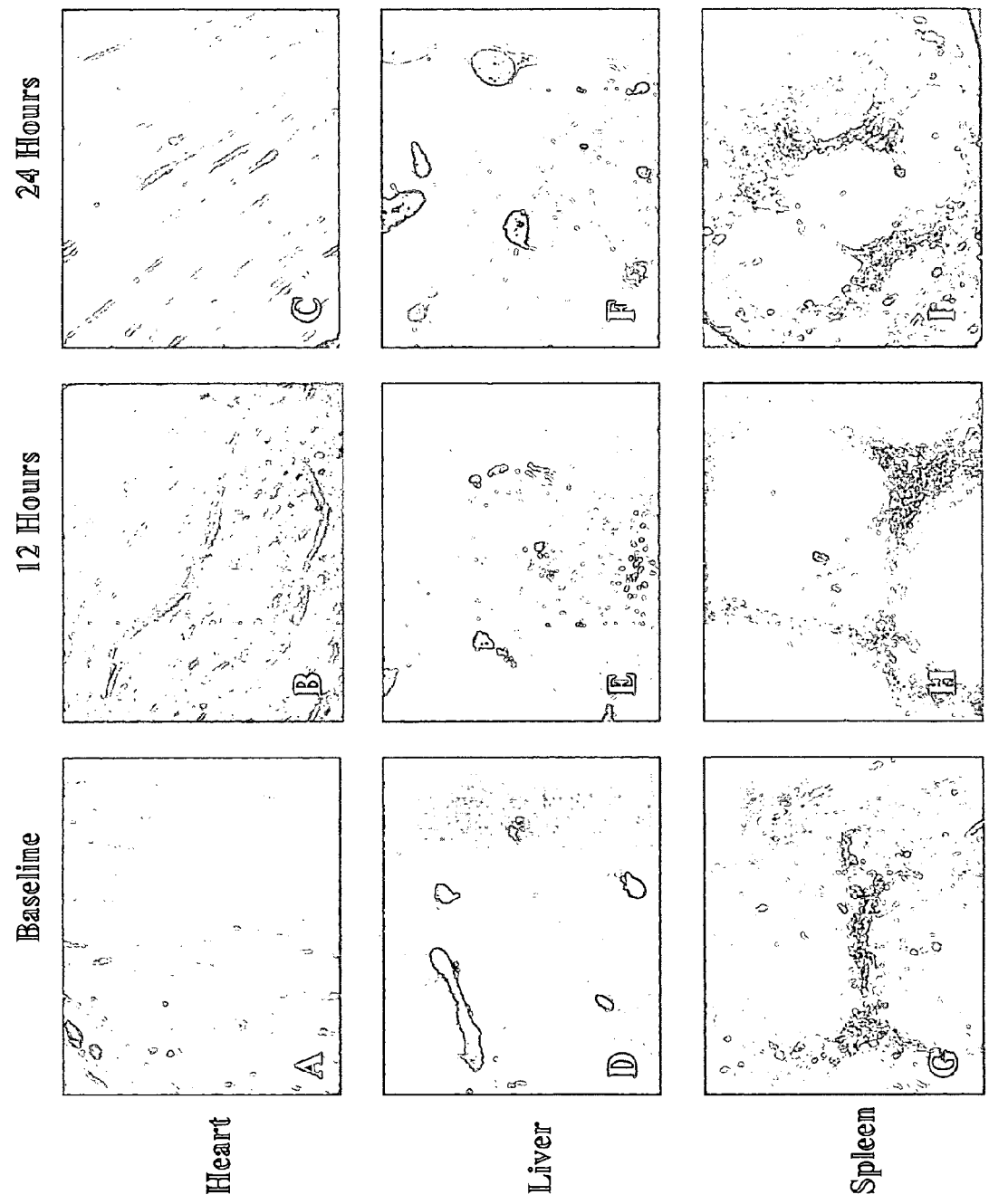
FIG. 3: The presence of MIF in the heart, liver, and spleen before and after LPS challenge. Preformed MIF in the heart, liver, and spleen (A, D, G) decreases 12 h after LPS challenge (B, E, and H) and is replenished after 24 b (C, F, and 1) as demonstrated by immunohistochemistry. Magnification: 100× (Kidney, Spleen), 400× (Heart).

Myocardial MIF mRNA Expression Following Endotoxin Challenge. Northern analysis of RNA obtained from the hearts of either control mice or from LPS challenged mice at given time points indicates that MIF mRNA is constitutively expressed in control mice, and that after LPS challenge, no significant change in MIF mRNA concentration is detectable in whole heart preparations (FIG. 3).

Example 11

Figure 4:
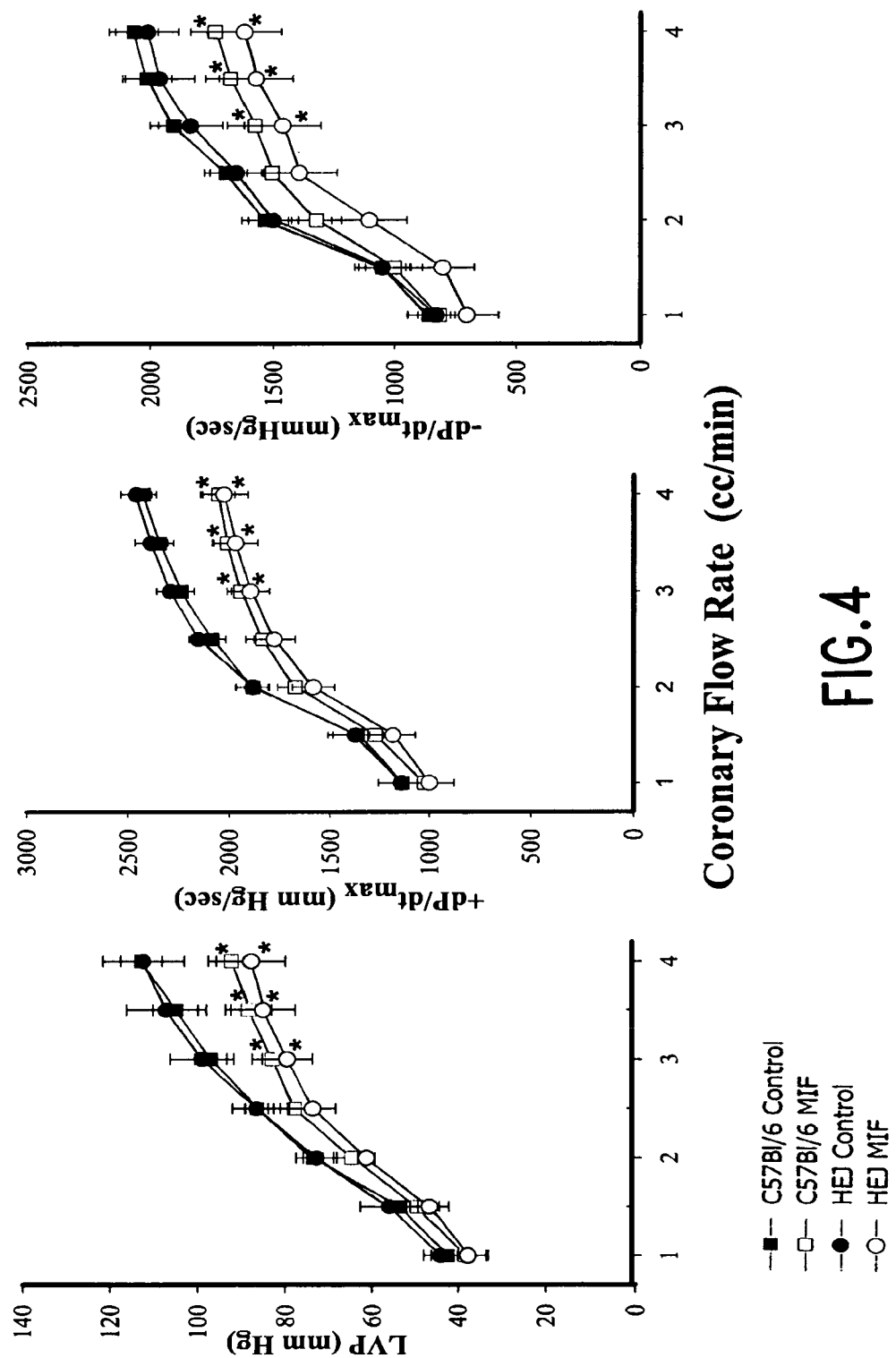
FIG. 4: Cardiac function determined by Langendorff preparation post-rMIF challenge in C57BL/6J mice and endotoxin-resistant C3H/HeJ mice demonstrates rMIF mediates cardiac dysfunction in an LPS-independent mechanism. Data represents the average of 7 (C3H/HeJ) to 10 (C57BL/6J) independent Langendorff experiments per group. *$p<0.05$.
Figure 6:
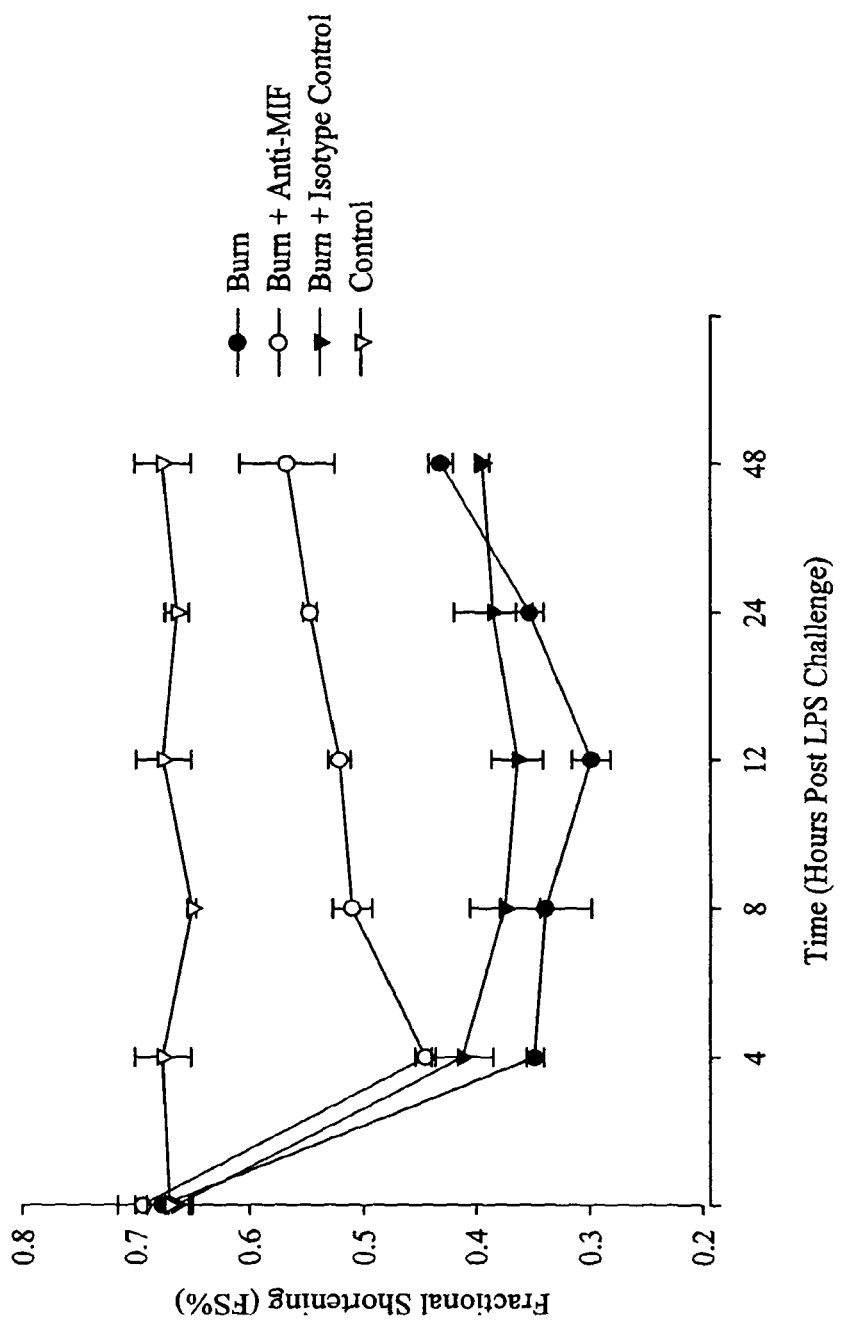
FIG. 6: Burn model demonstrating inhibition of MIF with anti-MIF antibody following LPS Challenge. The burn data demonstrates inhibition of MIF with the anti-MIF antibody and restores cardiac function following burning.

MIF induces systolic and diastolic cardiac dysfunction. To determine if MIF directly influences cardiac function, spontaneously beating normal mouse hearts (Langendorff preparation) were perfused with recombinant MIF (rMIF) at a concentration of 20 ng/ml, approximating that documented in the serum of humans with septic shock (20). Responses to MIF were determined in hearts from both C57BL/6J mice, and C3H/HeJ mice. C3H/HeJ mice are resistant to endotoxin (41-43), therefore controlling for the possibility that any depression observed might be due to trace endotoxin in the perfusate. Table 2 illustrates the responses of both mouse strains to retrograde aortic perfusion at 1.5 ml/m with control perfusate or perfusate containing 20 ng/ml recombinant MIF. Perfusion with MIF led to a significant decrease in LVP, +dP/dt$_{max}$, and −dP/dt$_{max}$ in both mouse strains. FIG. 4 illustrates the effect of MIF over a range of coronary flow rates. There is a step-wise increase in contractile performance in all hearts regardless of experimental group assignment. Comparison of the MIF exposed hearts with control hearts revealed a downward shift in the function curves, indicating significant systolic and diastolic depression in response to 20 ng/ml rMIF (p<0.05). The effect of MIF was statistically identical in both endotoxin sensitive (C57BL/6J) and endotoxin resistant (C3H/HeJ) strains. Likewise, there were no differences in LVP, +dP/dt$_{max}$, and −dP/dt$_{max}$ between the C57BL/6J and C3H/HeJ study hearts perfused with rMIF.

TABLE 2

Mean peak cardiac function before and after treatment with rMIF in a Landendorf preparation in C57BL/6J mice and LPS-resistant C3H/HeJ mice. *p < 0.05

| | LVP (mm Hg) | +dP/dt$_{max}$ (mm Hg/sec) | −dP/dt$_{max}$ (mm Hg/sec) |
|---|---|---|---|
| C57BL/6J Control (n = 10) | 92.9 ± 2.3 | 2180 ± 60 | 1856 ± 65 |
| C57BL/6J rMIF (n = 10) | 77.9 ± 5.1* | 1920 ± 89* | 1545 ± 122* |
| C3H/HeJ Control (n = 7) | 93.7 ± 3.5 | 2250 ± 42 | 1809 ± 84 |
| C3H/HeJ rMIF (n = 7) | 75.2 ± 5.5* | 1800 ± 106* | 1343 ± 138* |

Example 12

Anti-MIF antibodies improve LPS-induced cardiac depression in vivo. To determine the influence of MIF in the pathogenesis of cardiac dysfunction in vivo, serial echocardiography (M-mode) was performed on LPS challenged mice which had been pre-treated (90 minutes prior) with either anti-MIF monoclonal antibodies, an isotype control antibody, or no treatment (FIG. 5). At four hours post-LPS challenge, the fractional shortening % (FS %) of all LPS challenged mice were similarly depressed (50% reduction in FS %), irrespective of group assignment. Eight hours post-LPS challenge, however, mice injected with either anti-MIF monoclonal antibody demonstrated statistically significant recovery of FS % compared to LPS challenged groups receiving either no treatment or isotype antibody control (FIG. 5). This enhanced recovery of function continued at 12, 24, and 48 h. At 48 hours following challenge, anti-MIF treated groups had near total restoration of FS %, whereas LPS challenged groups remained profoundly depressed. Throughout the 48 hours, the FS % of sham mice did not significantly change, indicating that cardiac function was unaffected by anesthesia or the testing regimen itself. Additionally, at all time points, the mice injected with isotypic antibody controls were identical to animals challenged with LPS, indicating specificity of the anti-MIF antibody effects.

Example 13

Materials and Methods

Antibodies and cytokines. A polyclonal rabbit anti-rat MIF IgG (Torrey Pines BioLabs, Inc., Houston, Tex.) was used for western immunoblot and immunohistochemistry. This antibody has previously been shown to cross react with murine MIF and was prepared as previously described (23). A polyclonal goat anti-rabbit IgG-HRP (BioRad Corp., Hercules, Calif.) was used as a secondary antibody for western immunoblots and was stored at 4° C. Two monoclonal mouse anti-mouse (and human) MIF IgG1 antibodies (XIV. 15.5 and III.D.9, gift of Cytokine PharmaSciences, Inc.) and a monoclonal mouse IgG1 isotype control antibody (HB-49, gift from Cytokine PharmaSciences, Inc.) were used in the echocardiographic studies. In vivo neutralization of MIF activity by both the XIV.15.5 and III.D.9 clones have been previously demonstrated.

Animals, Experimental Design, and Burn Injury. Male C57BL/6J mice ages 6-10 weeks (Jackson Labs, Bar Harbor, Me.) were maintained in a specific pathogen free environment. Commercial chow and tap water were made available ad libitum. All animal protocols were reviewed and approved by the University of Texas Southwestern Medical Center Institutional Animal Care Advisory Committee and were in compliance with the rules governing animal use as published by the NIH. Mice were subjected to a 40% TBSA burn injury. Briefly, mice were anesthetized with isoflourane (1-2%) with 2.5 L/minute oxygen to effect. Hair was then removed from their back and sides using a surgical prep blade and 70% ethanol. Brass probes heated to 100° C. in boiling water were then applied in pairs (total of 8 probe surface areas) on the animal's side and back for 5 seconds. Alternatively, sham mice received anesthesia and were shaven but not given the burn injury. Intraperitoneal injection of Lactated Ringer's with Buprenex (2 cc LR+0.2 cc Buprenex (=0.05 mg/kg)) was given after the burn injury after the anesthesia was removed (with oxygen continued). Mice were then placed in individual cages under a heat lamp for approximately 1 hour and on a heating pad for the duration of the study and monitored closely. Mice were sacrificed at time points indicated in the figures by $CO_2$ asphyxiation followed by cervical dislocation. Monoclonal anti-MIF antibodies (III.D.9 and XIV.15.5) or an isotypic control (HB-49) were injected (100 µg in 200 µl PBS) intraperitoneally 90 minutes prior to burn injury in the echocardiogram studies. Whole hearts were removed, snap frozen in liquid nitrogen, and stored at −80° C. In parallel experiments, hearts were fixed in 10% neutral-buffered formalin for 24 hours and were then placed in 70% ethanol until they were processed for immunohistochemistry. Whole blood was collected by retro-orbital bleeding and serum collected and stored.

Protein Extraction and Western Blotting. Hearts stored at −80° C. were homogenized on ice in lysate buffer (10 mM HEPES, 2 mM EDTA, 0.1% Chaps, pH 7.4 with one Complete Mini-EDTA-Free Protease inhibitor cocktail tablet per 10 ml buffer, Roche Diagnostics, Mannheim, Germany). Protein concentration was quantified using the Bio-Rad Protein Assay (Hercules, Calif.). Fifty µg of total protein (lysate) diluted in Laemmeli sample buffer (Bio-Rad) in a 1:1 ratio to a final volume of 10 µl was then resolved on a 12% SDS polyacrylamide gel under reducing conditions. Prestained SDS-PAGE standards (Kaleidoscope Broad range, Bio-Rad Laboratories, Inc., Hercules, Calif.) were run with each gel in order to determine the approximate M.W. of detected bands. The gel was transferred to a PVDF membrane (NEN, Boston, Mass.) using a mini transblot transfer apparatus (Bio-Rad, Hercules, Calif.) at 100 V for 70 minutes and cooled with ice packs. The membrane was re-wet with methanol, washed a minimum of 3 times with 100+ ml water, and blocked (5% nonfat dry milk (Bio-Rad)/TBS/0.1% Tween-20 (TBS-T) overnight at 4° C. The membrane was then incubated with the primary rabbit anti-MIF (1:1250 dilution) for 2 hours at room temperature in 5% milk/TBS-T and washed once for 15 minutes in TBS-T, followed by five washes (5 minutes each) in TBS-T. It was then incubated for 1 hour with a HRP conjugated goat anti-rabbit antibody in TBS-T (1:5000) at room temperature, washed twice for 15 minutes, followed by five additional washes (5 minutes each) in TBS-T. To develop, 5 ml of ECL reagent (SuperSignal West Pico, Pierce, Rockford, Ill.) was placed on the PVDF membranes for 5 minutes, and the resulting chemiluminescent reaction was detected by Kodak X-OMAT AR Film (Eastman Kodak Co., Rochester, N.Y.).

The quantification of the single band density with the approximate molecular weight of MIF (12.5 kD) was determined using Quantity One software (Bio-Rad, Hercules, Calif., Ver. 4.4.0, Build 36) following conversion of radiographic film to TIFF files (8 bit grayscale) using a Scanjet 3400c (Hewlett Packard, Palo Alto, Calif.) and reported in arbitrary units (A.U.)/$mm^2$.

Immunohistochemistry. Tissue was fixed in neutral buffered formalin, processed to paraffin, and subsequently immunostained at room temperature on a BioTek Solutions Techmate™ 1000 automated immunostainer (Ventana Medical Systems, Tucson, Ariz.) using the Ultra-streptavidin biotin system with horseradish peroxidase and diaminobenzidine (DAB) chromogen (Signet Laboratories, Dedham, Mass.). Optimum primary antibody concentrations were predetermined using known positive control tissues (LPS challenged rat). Paraffin sections were cut at 3 µm on a rotary microtome, mounted on positively charged glass slides (POP100 capillary gap slides, Ventana Medical Systems, Tucson, Ariz.), and air-dried overnight. Sections were then deparaffinized in xylene and ethanol, quenched with fresh 3% hydrogen peroxide for 10 minutes to inhibit endogenous tissue peroxidase activity, and rinsed with de-ionized water. Sections were incubated in unlabeled blocking serum for 15 minutes to block nonspecific binding of the secondary antibody and then incubated for 25 minutes with either the polyclonal rabbit anti-rat MIF IgG (1:400, Torrey Pines BioLabs, Inc., Houston, Tex.) diluted in 1% citrate buffer (BioPath, Oklahoma City, Okla.) or with buffer alone as a negative reagent control. A negative reagent control was run for each time point and for each organ. Following washes in buffer, sections were incubated for 25 minutes with a biotinylated polyvalent secondary antibody solution (containing goat anti-rabbit immunoglobulins). Next, sections were washed with buffer, incubated in horseradish peroxidase-conjugated streptavidin-biotin complex for 15 minutes, washed again in buffer, and then incubated with 2 changes, 5 minutes each, of a freshly prepared mixture of DAB and $H_2O_2$ in buffer, followed by washing in buffer and then water. Sections were then counterstained with hematoxylin, dehydrated in a graded series of ethanol and xylene, and coverslipped. Slides were reviewed by light microscopy, and positive reactions with DAB were identified as a dark brown reaction product.

Determination of serum MIF levels. Sera from six mice were assayed for mouse MIF using the Chemikine™ Rat/Mouse macrophage inhibitory factor (MIF) EIA kit (Chemicon International, Inc., Temecula, Calif.) according to the manufacture's instructions. Briefly, 5 µl of standards, samples, or reaction buffer (blank) were added to each well in triplicate. Next, 100 µl of diluted MIF-HRP antibody conjugate was added to each well and allowed to incubate for 2 hours at room temperature. Wells were then washed five times, and 100 µl of 3,3',5,5'-tetramethylbenzidene (TMB) substrate was added and allowed to incubate in the dark for 30 minutes at room temperature. The stop reagent was added to each well, gently mixed, and the ELISA was read on an ELISA plate reader (EL 312e Microplate Reader, Bio-Tek Instruments, Winooski, Vt.) at 450 nm (630 nm background) within 30 minutes of completion of the assay.

Multiplex cytokine detection by Luminex. Plasma inflammatory cytokine (IL-1β, IL-2, IL-4, IL-5, IL-6, IL-10, IL-12, IFN-γ, TNF-α, and GM-CSF) concentrations were determined using the Mouse Cytokine Ten-Plex Antibody Bead Kit (Biosource International, Inc., Camarillo, Calif.) on a Luminex xMAP™ system (Luminex Corp., Austin, Tex.) according to the manufacturer's instructions. The plate was loaded onto the Luminex XYP™ platform, the instrument set to remove 50 µl, and the total event set to equal the 100 per bead set. At least 100 events (most >200) for each cytokine were collected in each sample in order to determine statistically significant results. Data was collected using the Luminex™ Data Collector Software (Luminex Corp., Austin, Tex.). The concentrations of the lot specific reconstituted standards used in each run were entered into the software and the analyte concentrations for unknown samples were then extrapolated from the cytokine specific standard curve using MasterPlex™ QT software (Version 1.2.8.58, Mirai Bio, Inc., Alameda, Calif.). Final concentrations were multiplied by 2 in order to account for the initial dilution factor. No samples were detected that were higher than the standards curves for any cytokine.

Total RNA isolation, MIF and β-actin probe preparation, and northern blotting. Hearts stored at −80° C. were placed in a liquid nitrogen filled pestle and ground to a fine powder with a mortar. Each powdered heart was then immediately placed in 2 ml Trizol (Invitrogen, Carlsbad, Calif.) and total RNA was isolated according to the manufacturer's protocols and quantified by spectrophotometry. An MIF specific Northern probe was prepared from an MIF containing plasmid (Image Clone I.D. 634910, Research Genetics, Huntsville, Ala.) isolated using Genelute HP Plasmid MidiPrep kit (Sigma, St. Louis, Mo.). The fragment was prepared by an EcoR1 and Not1 digestion (Fisher Scientific, Pittsburgh, Pa.) and gel purified and isolated on a 1.2% agarose gel using GenElute Agarose Spin Columns (Supelco, Bellefonte, Pa.). The β-actin probe DNA fragment was purchased from Ambion (Austin, Tex.). Both MIF and β-actin probes were labeled with 5 µl [α-$^{32}$P]dATP (3000 Ci/mmol, 10 mCi/ml) (PerkinElmer, Boston, Mass.) using Strip-EZ™ DNA probe synthesis kit (Ambion, Austin, Tex.) and purified in ProbeQuant Microcolumns (Amersham Pharmacia, Piscatany, N.J.) according to manufacturers' protocols.

RNA (10 µg) was resolved on 1.2% agarose gels at 100 volts for 1 hour and transferred to a Hybond-N+ membrane (Amersham Pharmacia, Buckingham, England) at 1.5 amps for 70 minutes on a transfer electrophoresis unit (TransPhor PowerLid, Hoefer Scientific Instruments, San Francisco). RNA was linked to the membrane for approximately 2 minutes using a GS Gene Linker (Bio-Rad, Hercules, Calif.). The membrane was prehybridized in a hybridization oven (Sorvall Life Science, Inc., Greensboro, N.C.) in Perfect-Hyb Plus (Sigma, St. Louis, Mo.) for 1 hour at 68° C. Sheared, denatured salmon or herring testis DNA (100 µg/ml) was then added for 1 hour, followed by the addition of approximately 0.1 µg probe labeled at >5×10$^8$ cpm/µg. The blot was then hybridized for 12 hours at 68° C. in the hybridization oven followed by washing at 68° C. in 2×SSC, 0.1% SDS. The membrane was washed for 1 hour, the buffer was exchanged, and then the membrane was washed for an additional hour at 68° C. The membrane was wrapped in Saran wrap, and mRNA was detected by Kodak X-OMAT AR Film after 24 hours (Eastman Kodak Co., Rochester, N.Y.). The same membrane was then re-probed in a similar manner with radiolabeled β-actin (0.1 µg probe labeled at >5×10$^8$ cpm/µg) (Ambion, Austin, Tex.). Densitometry was performed as described above for the western blots. The β-actin mRNA bands served as a control against which to normalize the MIF mRNA densitometry.

Ex vivo cardiac function determination by Langendorff. Mouse heart function was determined using the Langendorff assay procedure. Briefly, 200 Units heparin sulfate were injected intraperitoneally and the mice were sacrificed 20 minutes later. The heart was immediately removed and placed on ice in Krebs-Henseleit Buffer (2 mM NaHCO$_3$, 118 mM NaCl, 4.7 mM KCL, 1.2 mM KH$_2$PO$_4$, 1.2 mM MgSO$_4$, 2.5 mM CaCl$_2$, 11.1 mM glucose, pH 7.4, which was prepared fresh with demineralized, deionized water and bubbled with 95% O$_2$ and 5% CO$_2$ (pO$_2$ 590 mmHg, pCO$_2$ 38 mmHg)). The aorta was cannulated with PE50 tubing, the heart perfused in a retrograde manner through the aortic root with pre-filtered, oxygenated Krebs-Henseleit Buffer at a constant flow rate of 1.5 ml/minute (T 37° C., 100 ml recirculating volume). The heart was placed in a water-jacketed chamber to maintain constant temperature and humidity. PE60 intramedic polyethylene tubing, connected to a Statham pressure transducer, was inserted into the left ventricle (LV) to measure LV pressure. Temperature was monitored using a 27 gauge thermistor needle inserted into the LV muscle. After instrumentation, hearts were allowed to stabilize for 10 minutes, and hearts that failed to achieve a stable pressure or developed persistent arrhythmias during this time were excluded from the study. Following stabilization, LV pressure and its first derivative (dP/dt), heart rate, and coronary perfusion were measured simultaneously with a multi-channel Grass 7D polygraph (Grass Instruments, Quincy, Mass.). Ventricular performance as a function of coronary perfusion was determined for all hearts by plotting peak systolic LV pressure and $\pm dP/dt_{max}$ values against incremental increases in coronary flow rate.

Determination of cardiac dysfunction by echocardiography. Echocardiograms to assess systolic function were performed using M-mode measurements. Mice were anesthestized with 5% isofluorane with 2.5 L/m O$_2$ for 20 seconds (until unconscience) followed by 2% isofluorane and O$_2$ for an average of 12-15 minutes. Hair was removed from the thorax and upper abdomen using Nair® hair remover and gauze after sitting for 3 minutes. Echocardiographic measurements were obtained on anesthetized mice approximately 5-8 minutes after induction. Echocardiography was performed using a Hewlett-Packard Sonos 5500 (Agilent Technologies; Edmonton, Alberta, Canada) with a frame rate of 300-500 frames/second in a random and blinded manner. A 12 MHz linear transducer was placed on the left hemithorax interfaced with a layer of US transmission gel (Aquasonic 100, Parker Laboratories; Fairfield, N.J.). The two dimensional parasternal short-axis imaging plane guided LV M-mode tracings close to the papillary muscle level. Depth was set at a minimum of 2 cm with a sweep speed of 150 m/second. Tracings were printed on a Sony color printer (UP-5200, Sony).

M-mode measurements. Data represent the average of nine selected cardiac cycles from at least two separate scans. End diastole was defined as the maximal LV diastolic dimension, and end systole was defined as the peak of posterior wall motion. Fractional shortening % (FS %), a surrogate of systolic function, was calculated from LV dimensions as follows: FS (%)=LVED−LVES/LVED×100, as shown in FIG. 12.

Statistical Analysis. Northern and Western data are expressed as mean±standard error (SE) and statistically analyzed using a One Way-Analysis of Variance (ANOVA). A multiple comparison procedure was employed using the Tukey method to determine statistical significance between groups. Cardiac function determined by the Langendorff preparation (including stabilization data) is expressed as the mean±SE and separate analyses were performed for each LVP, +dP/dt$_{max}$, and −dP/dt$_{max}$ as a function of treatment group and coronary flow rate using a Repeated Measures-ANOVA. A multiple comparison procedure employing the Bonferroni method was used to determine significant differences between groups. Serum MIF levels are expressed as the mean±SE and were statistically analyzed using a One Way-ANOVA, with a multiple comparison procedure employing the Bonferroni method to determine significance between groups. Cardiac function determined by M-mode echocardiography is expressed as fractional shortening %±SE and analyzed using a One Way Repeated Measures-ANOVA. Additional comparisons were performed using the Tukey Test to determine significant differences between specific groups. Statistical significance for all analyses was defined as p≤0.05. All statistical analyses were performed using SigmaStat 2.03 (SPSS Inc., Chicago, Ill.) and Microsoft Excel (Microsoft Corp., Seattle, Wash.).

Results—Example 13

MIF protein is constitutively expressed by cardiac myocytes in vivo and is released in response to burn injury. The cytokine macrophage migration inhibitory factor (MIF) is present in both ventricular and atrial myocytes at baseline as demonstrated by western and immunohistochemistry (FIGS. 7 and 8). After burn injury, a significant decrease (2.1 fold) was identified at 8 hours with tissue concentrations of MIF returning to baseline levels by 12 hours (FIG. 7). This expression pattern was paralleled in liver, spleen, and the lung after burn injury (FIG. 8) and is consistent with the hypothesis that MIF is released in response mediators of burn injury.

Systemic MIF and IL-6 levels are increased after burn injury. Maximum systemic release of MIF (2.2 fold increase) was identified in serum at 4 hours and returned to baseline levels by 8 hours (FIG. 9). Maximum serum IL-6 levels were identified at 12 hours which returned to baseline levels by 48 hours. Serum IL-12 levels decreased after burn injury and were minimum at 24 hours and returned to baseline by 48 hours. No other cytokines tested (as listed in the materials and methods) were detected in the serum.

Figure 10:
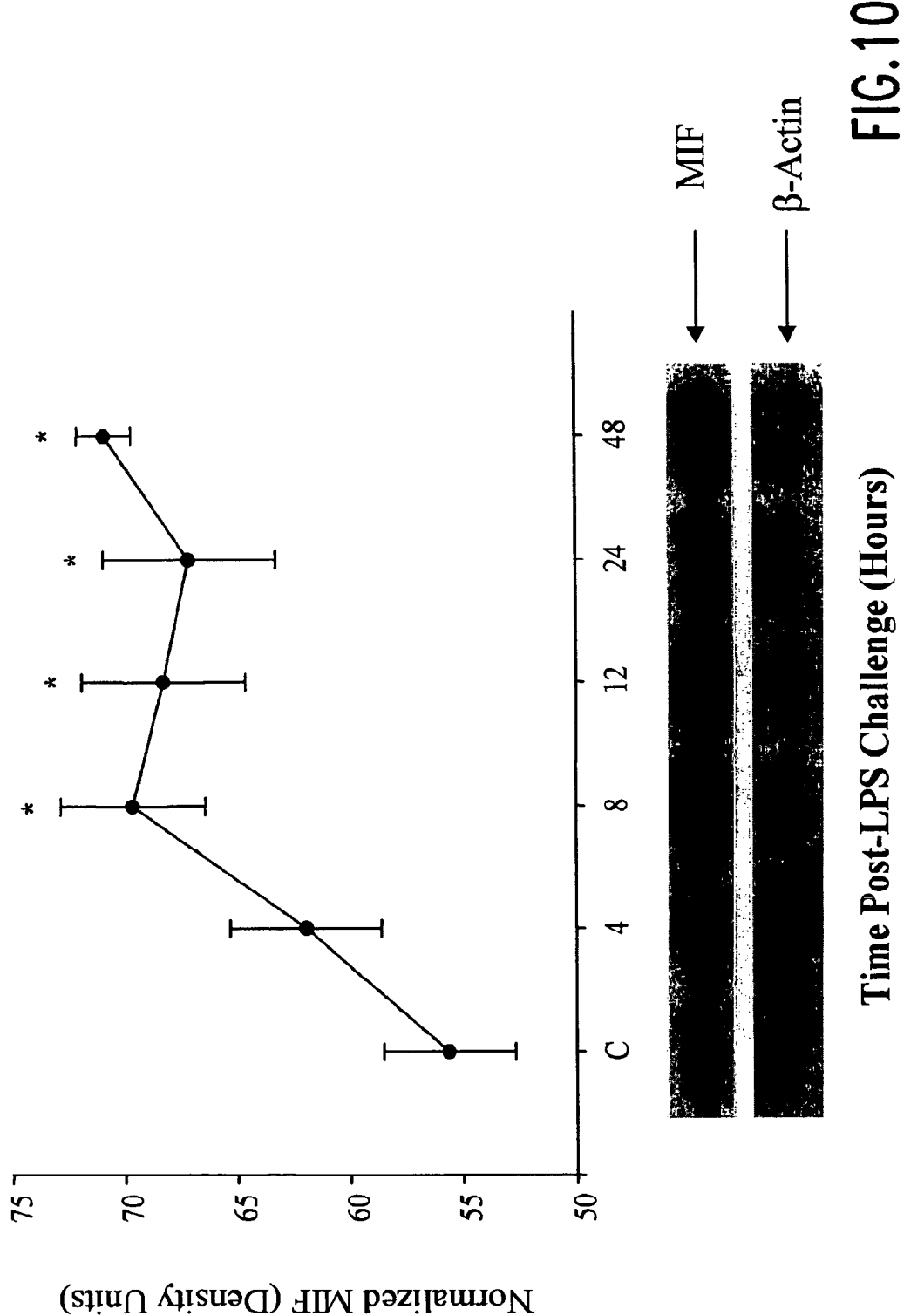
FIG. 10: Graphical representation and representative Northern Blot showing MIF mRNA upregulation following thermal trauma. Burn injury upregulates MIF mRNA expression in cardiac tissue significantly by 8 hours. MIF and β-actin mRNAs were detected using $^{32}$P radiolabeled probes complementary to MIF and β-actin mRNAs. Each data point represents the mean density in arbitrary units (A.U.)/mm$^2$±SE of 3 independent Northern blot experiments. A representative Northern blot is shown below the graph. Normalized MIF was determined by multiplying the MIF density by the relative β-actin density present. A One Way-ANOVA and a multiple comparison procedure using the Tukey method were employed to determine statistical significance compared to baseline (*p<0.05).

MIF mRNA in the heart significantly increases in the heart by 8 hours after burn injury. The levels of MIF mRNA were detected by Northern analysis from total RNA isolated from hearts of either sham mice or mice at 4, 8, 12, 24, and 48 hours following burn injury (FIG. 10). MIF mRNA is constitutively expressed in the heart, and significant increases in transcription initially occur at 8 hours, which are upregulated for the rest of the time course examined (48 hours) (FIG. 10).

Anti-MIF antibodies improve LPS-induced cardiac depression ex vivo. The responses of hearts to retrograde aortic perfusion at 1.5 ml/minute from mice undergoing the sham operation, burn injury, or burn injury with pre-treatment of anti-MIF antibodies were determined using a Langendorff analysis of heart function. Significant decreases in LVP, +dP/dt$_{max}$, −dP/dT$_{max}$, DR, dP40, TPP, RT90 and Time to Max −dP/dt were identified in mice 18 hours after undergoing burn injury (TABLE 3). Mice pre-treated with anti-MIF (Clone III.D.9) undergoing burn injury were completely protected by 18 hours (Table 3), while mice treated with the isotype control did not differ significantly from burn injury alone (data not shown).

Figure 11:
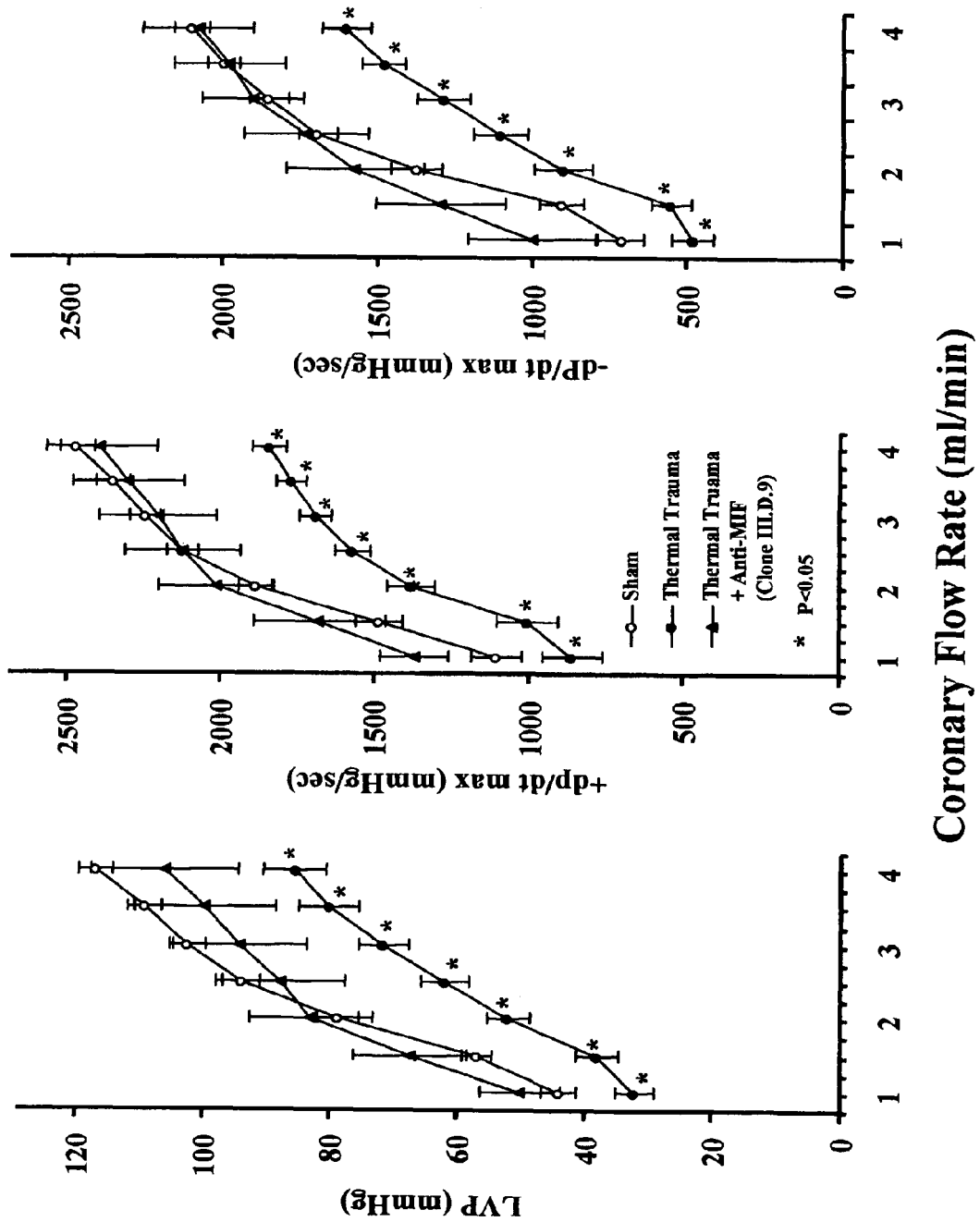
FIG. 11: Graphical representations of Coronary Flow Rates calculated three different ways comparing control measure of flow rate with untreated thermal trauma versus thermal trauma treated with Anti-MIF. Cardiac function determination by Langendorff preparation 18 hours after burn injury as a function of coronary flow (A) and Ca$^{2+}$. Cardiac function is expressed as the mean±SE of 25 independent Langendorff experiments (11 sham, 9 burn injury, 5 burn injury after anti-MIF treatment). Separate analyses were performed for each LVP, +dP/dt$_{max}$, and −dP/dt$_{max}$ as a function of treatment group and coronary flow rate using a Repeated Measures ANOVA and a multiple comparison procedure employing the Bonferroni method to determine significant differences between groups (*p<0.05).

FIG. 11 illustrates the function of hearts over a range of coronary flow rates from sham mice, burn injury mice, and burn injury mice pre-treated with anti-MIF antibodies 18 hours after the burn injury or sham procedure. Increases in coronary flow resulted in incremental increases in contractile performance in all hearts (groups) tested. Mice undergoing burn injury demonstrated a downward shift in the LVP, +dP/dt$_{max}$, and −dP/dT$_{max}$ function curves demonstrating significant systolic and diastolic dysfunction (FIG. 11). This dysfunction, however, was not present when anti-MIF antibodies were given where no significant differences to sham mice were identified (FIG. 11).

Anti-MIF monoclonal antibody therapy improves burn injury associated cardiac depression in vivo. Serial echocardiography was (M-mode) was performed on mice receiving burn injury, and mice pre-treated 90 minutes prior before burn injury with either of two anti-MIF antibodies, an isotype control, or no treatment (FIG. 12). At 4 and 8 hours, the fractional shortening percentage (FS %) of all burn injury treated mice were similarly depressed 21.4 FS (56.2 FS %-34.8 FS %), irrespective of anti-MIF treatment. At 12 hours post burn injury, however, mice injected with either of the two monoclonal anti-MIF antibodies demonstrated statistically significant recovery of FS % compared to burn injury mice receiving either no treatment of an isotype antibody control (FIG. 12). By 24 hours, the FS % of the treated mice was not significantly different from the controls indicating complete protection of the associated cardiac dysfunction. Throughout the 48 hours, the FS % of sham mice did not change significantly indicating that the testing regimen and anesthesia did not affect cardiac function. Lastly, mice receiving isotype control antibodies did not demonstrate significant differences from animals undergoing burn injury alone, indicating specificity of the anti-MIF antibody effects.

TABLE 3

In vitro stabilization data from isolated hearts in the Langendorff perfusion experiments. Cardiac function is expressed as the mean ± SE. Separate analyses were performed for each parameter (left column) as a function of treatment group. A Repeated Measures ANOVA with a multiple comparison procedure employing the Bonferroni method was used to determine significant differences between groups (*p < 0.05 compared to sham control).

| Cardiac Function Tested | Sham (n = 11) | Burn Injury (n = 9) | Burn Injury + Anti-MIF (n = 5) |
|---|---|---|---|
| LVP (mmHg) | 96.5 ± 1.5 | 63.2 ± 3.3* | 91.2 ± 9.6 |
| +dP/dt max (mmHg/sec) | 2217 ± 44 | 1631 ± 40* | 2256 ± 171 |

TABLE 3-continued

In vitro stabilization data from isolated hearts in the Langendorff perfusion experiments. Cardiac function is expressed as the mean ± SE. Separate analyses were performed for each parameter (left column) as a function of treatment group. A Repeated Measures ANOVA with a multiple comparison procedure employing the Bonferroni method was used to determine significant differences between groups (*p < 0.05 compared to sham control).

| Cardiac Function Tested | Sham (n = 11) | Burn Injury (n = 9) | Burn Injury + Anti-MIF (n = 5) |
|---|---|---|---|
| −dP/dt max (mmHg/sec) | 1855 ± 45 | 1187 ± 70* | 1840 ± 235 |
| DR | 1.22 ± 0.04 | 1.40 ± 0.05* | 1.29 ± .0.1 |
| dP40 (mmHg/sec) | 1868 ± 24 | 1383 ± 31* | 1960 ± 150 |
| TPP (msec) | 82.0 ± 2.5 | 72.8 ± 2.5* | 86.2 ± 2.0 |
| RT90 (msec) | 79.6 ± 4.5 | 68.8 ± 1.9* | 84.2 ± 2.8 |
| Time to Max +dP/dt (msec) | 49.1 ± 0.7 | 47.6 ± 0.6 | 53.0 ± 1.2 |
| Time to Max −dP/dt (msec) | 50.1 ± 0.5 | 45.7 ± 1.3* | 53.6 ± 1.7 |
| CPP (mmHg) | 89.2 ± 4.9 | 91.0 ± 6.3 | 84.2 ± 5.7 |
| CVR (mmHg) | 59.4 ± 3.3 | 60.6 ± 4.2 | 56.1 ± 3.8 |
| HR (bpm) | 321 ± 6 | 315 ± 7 | 322 ± 16 |

Example 14

To determine the role that TNF-α signaling has in MIF secretion and its associated cardiac dysfunction in a model of sublethal endotoxicosis, the following experiments were carried out in Example 14.

Materials and Methods

Antibodies and cytokines. A polyclonal rabbit anti-rat MIF IgG (Torrey Pines BioLabs, Inc., Houston, Tex.) which cross reacts with murine MIF was used for western immunoblot and immunohistochemistry. A polyclonal goat anti-rabbit IgG-HRP (BioRad Corp., Hercules, Calif.) was used as a secondary antibody for western immunoblots. Two monoclonal mouse anti-mouse (and human) MIF IgG1 antibodies (XIV.15.5 and III.D.9, gift of Cytokine PharmaSciences, Inc., King of Prussia, Pa.) and a monoclonal mouse IgG1 isotype control antibody (HB-49, gift from Cytokine PharmaSciences, Inc.) were used in the echocardiographic studies. In vivo neutralization of MIF activity by both the XIV.15.5 and III.D.9 clones have been previously demonstrated. Recombinant human TNFR:Fc (Enbrel®) used to neutralize TNF-α was a gift from Immunex Corp./Amgen, Inc., (Thousand Oaks, Calif.). Recombinant human MIF was synthesized according to the method of Bernhagen et al. and provided by Cytokine Pharmasciences, Inc.

Animals and Experimental Design. Pathogen-free, adult male C57BL/6J mice were obtained at 6-10 weeks of age and utilized at approximately 12 weeks of age (Jackson Labs, Bar Harbor, Me.). Breeding pairs of B6:129 PF1/J and B6; 129S-Tnfrsf1a$^{tm1\ Imx}$ Tnfrsf1b$^{tm1\ Imx}$ mice (TNFR−/−) were purchased from Jackson Laboratory (Bar Harbor, Me.) and male offspring were utilized after genotyping at 20-24 weeks (30-40 grams). Sterile commercial chow and water were made available ad libitum. All animal protocols were reviewed and approved by the University of Texas Southwestern Medical Center Institutional Animal Care Advisory Committee and were in compliance with the rules governing animal use as published by the NIH.

Mice were injected intraperitoneally with 4 mg/kg E. coli 0111:B4 LPS (Sigma-Aldrich Corp., St. Louis, Mo.) and sacrificed by $CO_2$ asphyxiation and subsequent cervical dislocation. Uninjected mice were used as controls. The two anti-MIF antibodies (III.D.9 and XIV.15.5, gift of Cytokine PharmaSciences, Inc., King of Prussia, Pa.) and their isotype control (HB-49, gift from Cytokine PharmaSciences, Inc.) were injected (100 μg in 200 μg PBS) intraperitoneally 90 minutes before the LPS challenge in the echocardiogram studies. Enbrel® (rhTNFR:Fc) was injected intraperitoneally (5 mg/kg or 300 μg in 0.5 ml PBS) 75 minutes prior to LPS challenge in wild type mice.

Whole hearts were removed and snap frozen in liquid nitrogen and stored at −80° C. or fixed in 10% neutral-buffered formalin for 24 hours and placed in 70% ethanol for immunohistochemistry. Whole blood was collected by retro-orbital bleeding and serum was separated using separator tubes. Serum was transferred to a sterile snap-top tube and frozen at −80° C. until assayed by ELISA.

Determination of serum MIF levels. Sera from six mice were assayed for mouse MIF using the Chemikine™ Rat/Mouse macrophage inhibitory factor (MIF) EIA kit (Chemicon International, Inc., Temecula, Calif.) according to the manufacturer's instructions. Briefly, 5 μl of standards, samples, or reaction buffer (blank) were added to each well in duplicate. Diluted MIF-HRP antibody conjugate was added to each well (100 μl) and allowed to incubate for 2 hours at room temperature. Wells were then washed five times, and TMB substrate (100 μl) was allowed to incubate in the dark for 30 minutes at room temperature. The stop reagent was added to each well, gently mixed, and the ELISA was read on an ELISA plate reader (EL 312e Microplate Reader, Bio-Tek Instruments, Winooski, Vt.) at 450 nm (630 mm background) within 30 minutes of completion of the assay.

Protein Extraction and Western Blotting. Hearts stored at −80° C. were homogenized on ice in lysate buffer (10 mM HEPES, 2 mM EDTA, 0.1% Chaps, pH 7.4) with one Complete Mini-EDTA-Free Protease inhibitor cocktail tablet per 10 ml buffer (Roche Diagnostics, Mannheim, Germany). Protein concentration was quantified using the Bio-Rad Protein Assay (Hercules, Calif.) and 50 μg of protein diluted in Laemmeli sample buffer (Bio-Rad) was added in a 1:1 ratio to a final volume of 10 μl and resolved on a 12% SDS polyacrylamide gel under reducing conditions. Prestained SDS-PAGE standards (Kaleidoscope Broad range, Bio-Rad Laboratories, Inc., Hercules, Calif.) were run (10 μl/lane) with each gel in order to determine the approximate M.W. of detected bands. The gel was transferred to a PVDF membrane (NEN, Boston, Mass.) using the Mini Transblot® electrophoretic transfer cell (Bio-Rad, Hercules, Calif.) at 100 V for 70 minutes and cooled with ice packs. Subsequently, the membrane was re-wet with methanol, washed a minimum of 3 times with 100 ml water, and placed in block (5% nonfat dry milk (Bio-Rad)/TBS/0.1% Tween-20 (TBS-T) overnight at 4° C. The membrane was then incubated with the primary rabbit anti-MIF (1:1250 dilution) for 2 hours at room temperature in 5% milk/TBS-T. The membrane was washed 1 time for 15 minutes in TBS-T, followed by five washes (5 minutes each). The membrane was then incubated for 1 hour with a HRP conjugated goat anti-rabbit antibody (diluted 1:5000) in TBS-T at room temperature. The membrane was then washed twice for 15 minutes, followed by five additional washes (5 minutes each). The membrane was then developed for 5 minutes with 5 ml of ECL reagents (SuperSignal West Pico, Pierce, Rockford, Ill.), and the resulting chemiluminescent reaction was detected by Kodak X-OMAT AR Film (Eastman Kodak Co., Rochester, N.Y.).

Quantification of the single band density with the approximate molecular weight of MIF (12.5 kD) was determined using Quantity One software (Bio-Rad, Hercules, Calif., Ver. 4.4.0, Build 36) following conversion of radiographic film to TIFF files (8 bit grayscale) using a Scanjet 3400c (Hewlett Packard, Palo Alto, Calif.) and reported in arbitrary units (A.U.)/mm$^2$.

Immunohistochemistry. Tissue was fixed in neutral buffered formalin and processed to paraffin and subsequently immunostained at room temperature on a BioTek Solutions Techmate™ 1000 automated immunostainer (Ventana Medical Systems, Tucson, Ariz.) using the Ultra-streptavidin biotin system with horseradish peroxidase and diaminobenzidine (DAB) chromogen (Signet Laboratories, Dedham, Mass.). Paraffin sections were cut at 3 µm on a rotary microtome, mounted on positively charged glass slides (POP100 capillary gap slides, Ventana Medical Systems, Tucson, Ariz.) and air-dried overnight. Sections were then deparaffinized in xylene and ethanol, quenched with fresh 3% hydrogen peroxide for 10 minutes to inhibit endogenous tissue peroxidase activity, and rinsed with deionized water. Sections were incubated in unlabeled blocking serum for 15 minutes to block nonspecific binding of the secondary antibody and then incubated for 25 minutes with either rabbit anti-MIF (1:400, Torrey Pines BioLabs, Inc., Houston, Tex.) diluted in 1% citrate buffer (BioPath, Oklahoma City, Okla.), or with buffer alone as a negative reagent control. Following washes in buffer, sections were incubated for 25 minutes with a biotinylated polyvalent secondary antibody solution (containing goat anti-rabbit antibodies). Next, sections were washed with buffer, incubated in horseradish peroxidase-conjugated streptavidin-biotin complex for 15 minutes, washed again in buffer, and then incubated with 2 changes, 5 minutes each, of a freshly prepared mixture of DAB and $H_2O_2$ in buffer, followed by washing in buffer and then water. Sections were then counterstained with hematoxylin, dehydrated in a graded series of ethanol and xylene, and coverslipped. Slides were reviewed by light microscopy and positive reactions with DAB were identified as a dark brown reaction product.

Total RNA isolation, MIF and β-actin probe preparation, and northern blotting. Hearts stored at −80° C. were placed in a liquid nitrogen filled pestle and ground to a fine powder with a mortar. Each powdered heart was then immediately placed in 2 ml Trizol (Invitrogen, Carlsbad, Calif.) and total RNA was isolated according to the manufacturer's protocols and quantified by spectrophotometry. An MIF specific Northern probe was prepared from an MIF containing plasmid (Image Clone I.D. 634910, Research Genetics, Huntsville, Ala.) isolated using Genelute HP Plasmid MidiPrep kit (Sigma, St. Louis, Mo.). The fragment was prepared by an EcoR1 and Not1 digestion (Fisher Scientific, Pittsburgh, Pa.) and gel purified and isolated on a 1.2% agarose gel using GenElute Agarose Spin Columns (Supelco, Bellefonte, Pa.). The β-actin probe DNA fragment was purchased from Ambion (Austin, Tex.). Both MIF and (β-actin probes were labeled with 5 µl [α$^{32}$P]dATP (3000 Ci/mmol, 10 mCi/ml) (PerkinElmer, Boston, Mass.) using Strip-EZ™ DNA probe synthesis kit (Ambion, Austin, Tex.) and purified in ProbeQuant Microcolumns (Amersham Pharmacia, Piscatany, N.J.) according to manufacturers' protocols.

Isolated total RNA (10 µg) was combined with formaldehyde loading dye (Ambion, Inc.) at a ratio of 1:3 sample: loading dye according to the manufacturer's protocols. Each gel had a 0.24-9.5 kB RNA ladder (Invitrogen Corp.) ran in parallel with samples (10 µg). Samples and RNA ladder were placed at 65° C. for 10 minutes prior to electrophoresis and resolved on a 1.2% agarose gels with 1×TAE buffer (Ambion, Inc.) at 100 volts for 1 hour and transferred to a Hybond-N+ membrane (Amersham Pharmacia, Buckingham, England) at 1.5 amps for 70 minutes on a transfer electrophoresis unit (TransPhor PowerLid, Hoefer Scientific Instruments, San Francisco) in 0.5×TAE. RNA was linked to the membrane for approximately 2 minutes using a GS Gene Linker (Bio-Rad, Hercules, Calif.). The membrane was prehybridized in a hybridization oven (Sorvall Life Science, Inc., Greensboro, N.C.) in Perfect-Hyb Plus (Sigma, St. Louis, Mo.) with sheared, denatured salmon sperm DNA (100 µg/ml) for 1 hour at 68° C. The probes were prepared by heating to 90° C. for 10 minutes (10 µl probe with 100 µl 10 mM EDTA), followed by the addition of approximately 0.1 µg probe labeled at >5×10$^8$ cpm/µg to the hybridization buffer. The blot was then hybridized for 12 hours at 68° C. followed by washing at 68° C. in 2×SSC, 0.1% SDS. The membrane was washed for 1 hour, the buffer was exchanged, and then the membrane was washed for an additional hour at 68° C. The membrane was wrapped in Saran wrap, and mRNA was detected by Kodak X-OMAT AR Film after 24 hours (Eastman Kodak Co., Rochester, N.Y.). The same membrane was then re-probed in a similar manner with radiolabeled β-actin (0.1 µg probe labeled at >5×10$^8$ cpm/µg) (Ambion, Austin, Tex.). Densitometry was performed as described above for the western blots. The β-actin mRNA bands served as a control against which to normalize the MIF mRNA densitometry.

Ex vivo cardiac function determination by Langendorff Mouse heart function was determined using the Langendorff assay procedure. Briefly, 200 Units heparin sulfate were injected intraperitoneally and the mice were sacrificed 20 minutes later. The heart was immediately removed and placed on ice in Krebs-Henseleit Buffer (2 mM NaHCO$_3$, 118 mM NaCl, 4.7 mM KCL, 1.2 mM KH$_2$PO$_4$, 1.2 mM MgSO$_4$, 2.5 mM CaCl$_2$, 11.1 mM glucose, pH 7.4, which was prepared fresh with demineralized, deionized water and bubbled with 95% O$_2$ and 5% CO$_2$(pO$_2$ 590 mmHg, pCO$_2$ 38 mmHg)). The aorta was cannulated with PE50 tubing, the heart perfused in a retrograde manner through the aortic root with pre-filtered, oxygenated Krebs-Henseleit Buffer at a constant flow rate of 1.5 ml/minute (constant temperature of 37° C., 100 ml recirculating volume). The heart was placed in a water-jacketed chamber to maintain constant temperature and humidity. Intramedic polyethylene tubing (PE60), connected to a Statham pressure transducer, was inserted into the left ventricle (LV) to measure LV pressure. Temperature was monitored using a 27 gauge thermistor needle inserted into the LV muscle. After instrumentation, hearts were allowed to stabilize for 10 minutes, and hearts that failed to achieve a stable pressure or developed persistent arrhythmias during this time were excluded from the study. Following stabilization, LV pressure and its first derivative (dP/dt), heart rate, and coronary perfusion were measured simultaneously with a multi-channel Grass 7D polygraph (Grass Instruments, Quincy, Mass.). Ventricular performance as a function of coronary perfusion was determined for all hearts by plotting peak systolic LV pressure and±dP/dt$_{max}$ values against incremental increases in coronary flow rate. Hearts were perfused with or without 20 ng/ml rMIF added to the perfusate.

Determination of cardiac dysfunction by echocardiography. Echocardiograms to assess systolic function were performed using M-mode measurements. Mice were anesthestized with 5% isofluorane with 2.5 L/m 0$_2$ for 20 seconds (until unconscience) followed by 2% isofluorane and 0$_2$ for an average of 12-15 minutes. Hair was removed from the thorax and upper abdomen using Nair® hair remover and gauze after sitting for 3 minutes. Echocardiographic measurements were obtained on anesthetized mice approximately 5-8 minutes after induction. Echocardiography was performed using an Acuson Sequoia™ Model C256 (Siemens Medical Solutions, USA, Inc., Mountain View, Calif.) with a frame rate of 300-500 frames/second in a random and blinded manner. A 15

MHz linear transducer (15L8, Siemens Medical Solutions, USA, Inc.) was placed on the left hemithorax interfaced with a layer of ultrasound transmission gel (Aquasonic 100, Parker Laboratories; Fairfield, N.J.). The two dimensional parasternal short-axis imaging plane guided LV M-mode tracings close to the papillary muscle level. Depth was set at a minimum of 2 cm with a sweep speed of 200 m/second.

Figure 18:
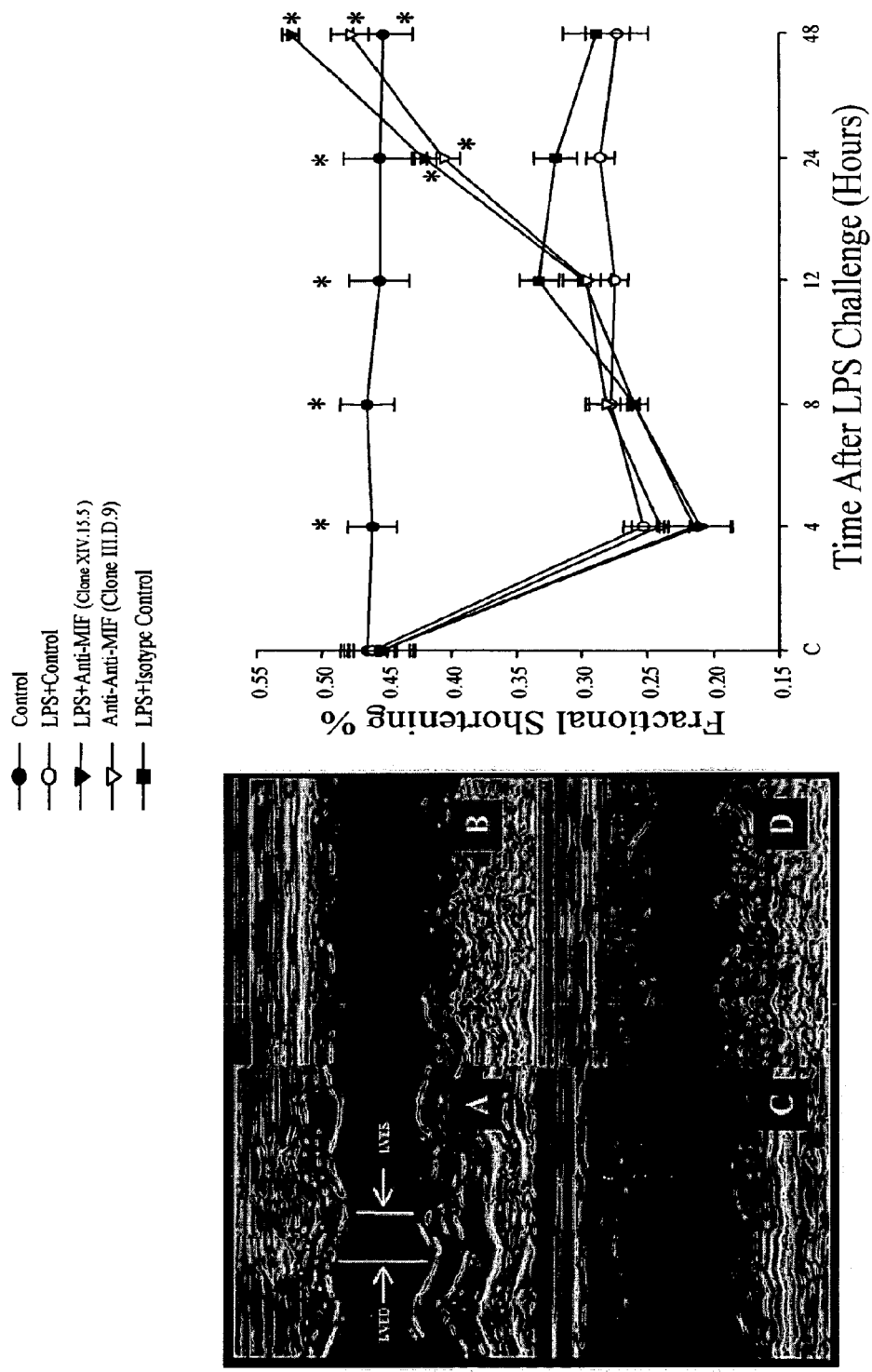
FIG. 18: Echocardiographic assessment of the effects of LPS and LPS plus anti-MIF antibody administration on cardiac function in TNFR−/− mice. Representative M-mode echocardiograms in wild-type mice at baseline and 4 h after LPS administration, A and B, respectively. C and D show, respectively, representative echocardiograms in LPS plus anti-MIF treated mice at 4 and 48 hours. A significant protection in cardiac function (FS %) is observed in LPS challenged mice when anti-MIF anti-bodies are given pre-treatment (E). Data represents the average of 9 cardiac cycles from 3 mice monitored at multiple time points. *p<0.05.

M-mode measurements. Data represent the average of nine selected cardiac cycles from at least two separate scans. End diastole was defined as the maximal LV diastolic dimension, and end systole was defined as the peak of posterior wall motion. Fractional shortening % (FS %), a surrogate of systolic function, was calculated from LV dimensions as follows: FS (%)=LVED−LVES/LVED×100, as shown in FIG. 18.

Multiplex cytokine detection by Luminex. Plasma inflammatory cytokine (IL-1β, IL-2, IL-4, IL-5, IL-6, IL-10, IL-12, IFN-γ, TNF-α, and GM-CSF) concentrations were determined using the Mouse Cytokine Ten-Plex Antibody Bead Kit (Biosource International, Inc., Camarillo, Calif.) on a Luminex xMAP™ system (Luminex Corp., Austin, Tex.) according to the manufacturer's instructions. The plate was loaded onto the Luminex XYP™ platform, the instrument set to remove 50 µl, and the total event set to equal the 100 per bead set (200 collected for most). Data was collected using the Luminex™ Data Collector Software (Luminex Corp., Austin, Tex.). The concentrations of the lot specific reconstituted standards used in each run were entered into the software and the analyte concentrations for unknown samples were then extrapolated from the cytokine specific standard curve using MasterPlex™ QT software (Version 1.2.8.58, Mirai Bio, Inc., Alameda, Calif.). Final concentrations were multiplied by 2 in order to account for the initial dilution factor. No samples were detected that were higher than the standards curves for any cytokine.

Statistical Analysis. Northern and Western data are expressed as mean±standard error (SE) and statistically analyzed using a One Way-Analysis of Variance (ANOVA). A multiple comparison procedure was employed using the Tukey method to determine statistical significance between groups. Cardiac function determined by the Langendorff preparation (including stabilization data) is expressed as the mean±SE and separate analyses were performed for each LVP, +dP/dt$_{max}$, and −dP/dt$_{max}$ as a function of treatment group and coronary flow rate using a Repeated Measures-ANOVA. A multiple comparison procedure employing the Bonferroni method was used to determine significant differences between groups. Serum MIF levels are expressed as the mean±SE and were statistically analyzed using a One Way-ANOVA, with a multiple comparison procedure employing the Bonferroni method to determine significance between groups. Cardiac function determined by M-mode echocardiography is expressed as fractional shortening %±SE and analyzed using a One Way Repeated Measures-ANOVA. Additional comparisons were performed using the Tukey Test to determine significant differences between specific groups. Statistical significance for all analyses was defined as p≤0.05. All statistical analyses were performed using SigmaStat 2.03 (SPSS Inc., Chicago, Ill.) and Microsoft Excel (Microsoft Corp., Seattle, Wash.).

Results—Example 14

Serum MIF levels in WT mice, WT mice pre-treated with Enbrel®, and TNFR−/− mice. Serum levels of MIF reach maximum (~1.5 fold baseline) at 8 hours in wild type mice after LPS challenge (FIG. 13A). When TNFR−/− mice are challenged with LPS, maximum serum MIF levels occur as 12 hours (~1.7 fold baseline) (FIG. 13B). Maximum serum MIF levels (~2.3 fold baseline) were identified in wild type mice pre-treated (60 minutes) with Enbrel® and challenged with LPS at 24 hours (FIG. 13C).

Figure 14:
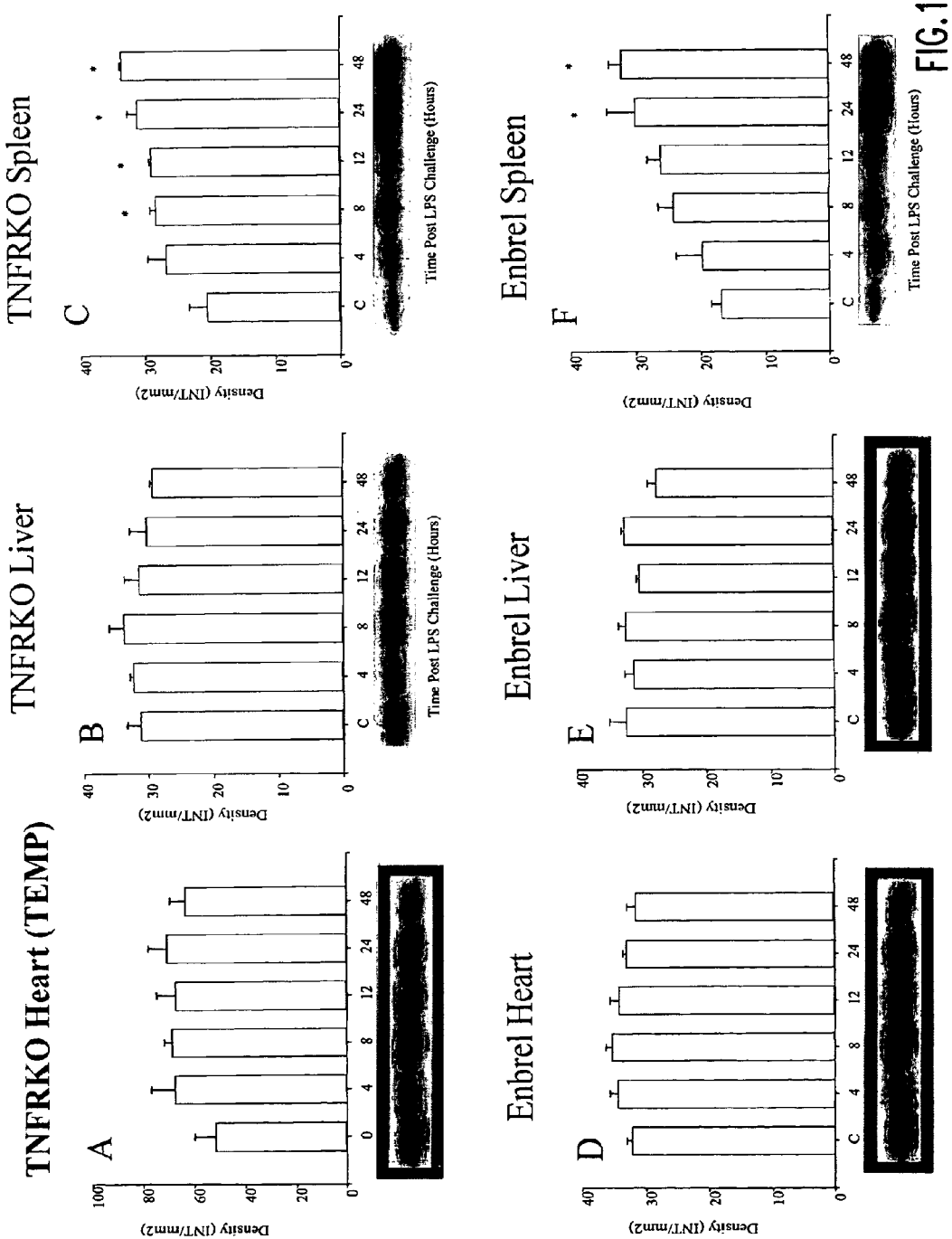
FIG. 14: MIF protein release is not detected after LPS challenge in cardiac tissue. Each data point is the mean (+/−standard error) of 3 independent Western blot experiments. A representative Western blot is shown below the graph. *p<0.05
Figure 15:
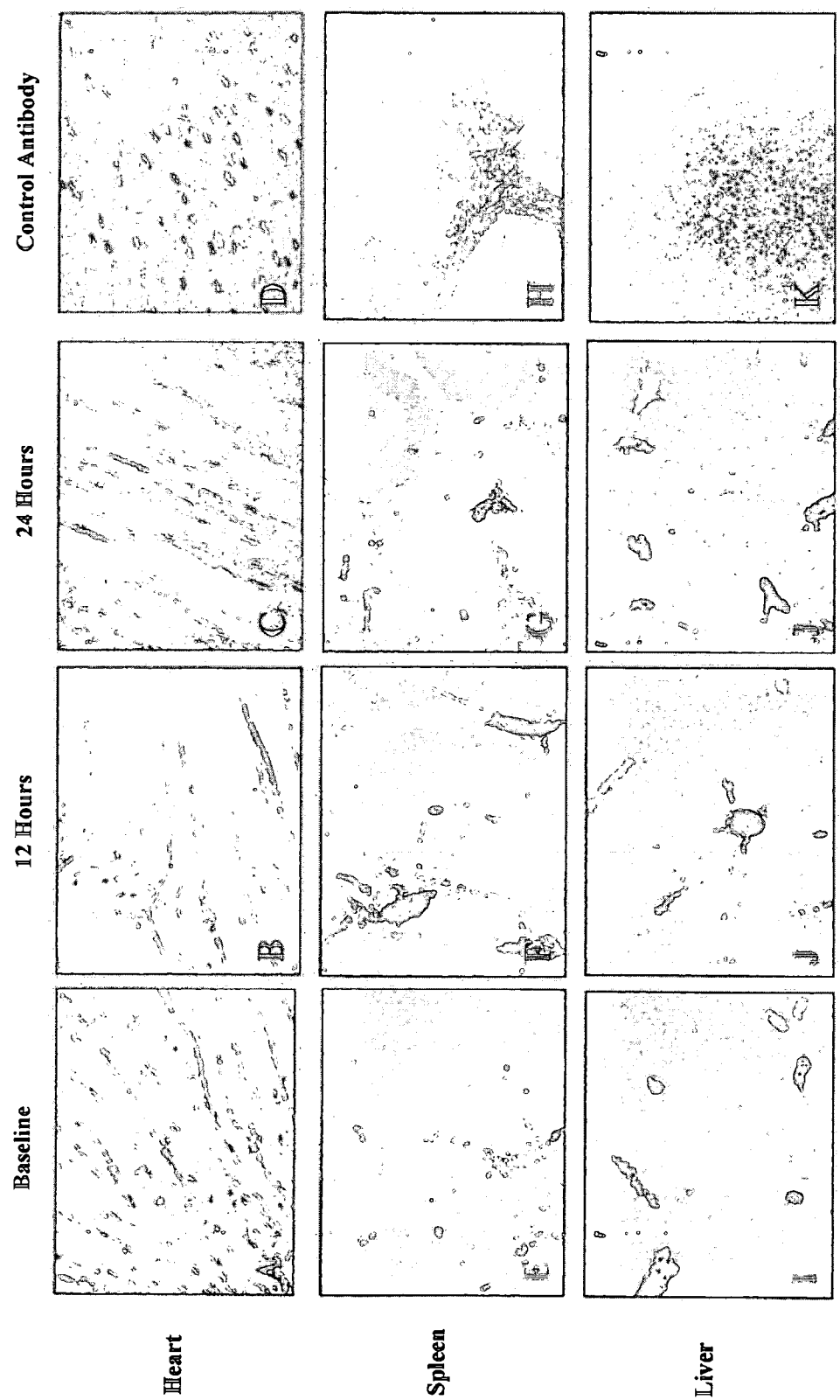
FIG. 15: The presence of MIF in the heart, liver, and spleen before and after LPS challenge in TNFR−/− mice. Preformed MIF in the heart, liver, and spleen (A, D, G) does not decrease 12 hours after LPS challenge (B, F, J) which is seen in wild type mice as demonstrated by immunohistochemistry. Magnification: 100× (Kidney, Spleen), 400× (Heart).

Cardiac MIF is not released from the heart, spleen, or liver in TNFR−/− mice after LPS challenge. Both western and immunohistochemistry analysis performed on cardiac, liver, and spleen demonstrated that previously documented release in wild type mice after LPS challenge did not occur at any time in TNFR−/− mice or wild type mice pre-treated with Enbrel®, both of which prevent TNF-α signaling (FIGS. 14 and 15).

Figure 16:
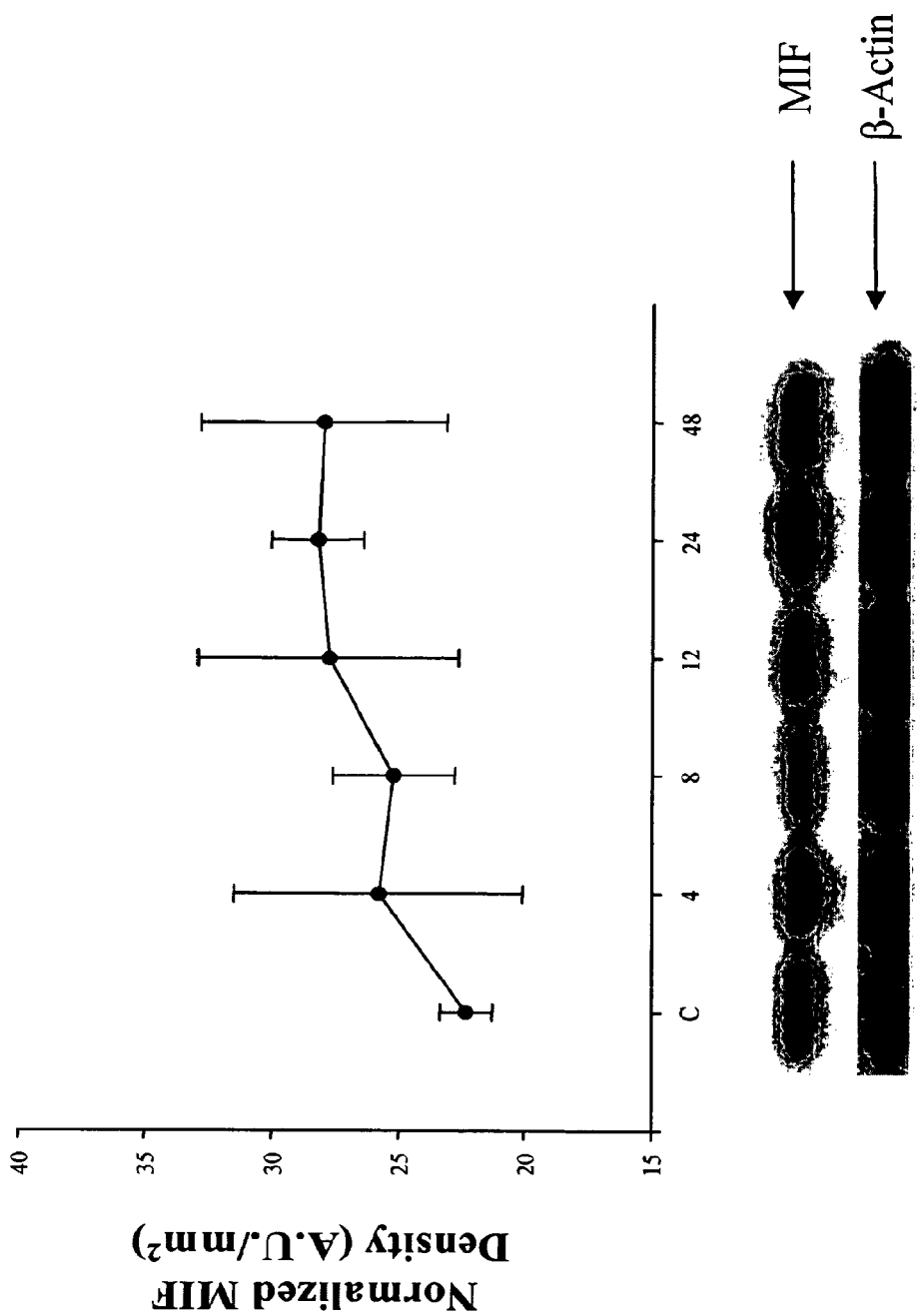
FIG. 16: LPS challenge does not upregulate MIF mRNA in cardiac tissue in TNFR−/−mice. Each data point in the graph is the mean (+/−standard error) of 3 independent Northern blot experiments. A representative Northern blot is shown below the graph. No significant differences between time points were identified (p>0.05).

Cardiac MIF transcription is not modulated in TNFR−/− mice after LPS challenge. Detection of MIF mRNA from isolated total RNA from heart tissue from TNFR−/− mice challenge with LPS demonstrates that transcription of MIF is not upregulated after LPS challenge (FIG. 16), which has been identified in wild type mice previously at 48 hours.

MIF has direct cardiodepressant effects in TNFR−/− mice to the same extent as in WT mice. To determine if MIF directly influences cardiac function independently of TNF, spontaneously beating normal mouse hearts (Langendorff preparation) were perfused with recombinant human MIF (rMIF) at a concentration of 20 ng/ml, approximating the documented serum levels in patients with septic shock (25). The human MIF used in the Langendorff perfusion studies has been shown to have an approximately 90% homology with murine MIF and has been shown to have cross species biologic function.

Table 4 demonstrates that the responses of the background strain of TNFR−/− mice, C57BL/6 mice, and the TNFR−/− mice to retrograde aortic perfusion at 1.5 ml/minute with control perfusate or perfusate containing 20 ng/ml rMIF. Perfusion with rMIF led to a significant decrease in LVP, +dP/dt$_{max}$, −dP/dT$_{max}$, and dp40 (mm Hg/sec) in both mouse strains while other parameters (time to max±dP/dt, CPP, CVR, and HR) were unaffected. FIG. 18 illustrates the effect of rMIF over a range of coronary flow rates. Increases in coronary resulted in a step-wise increase in contractile performance regardless of experimental group assignment. MIF challenged hearts demonstrated a downward shift in function curves, resulting in significant systolic (+dP/dt) and diastolic (−dP/dt) function curves in response to 20 ng/ml (p<0.05).

Figure 17:
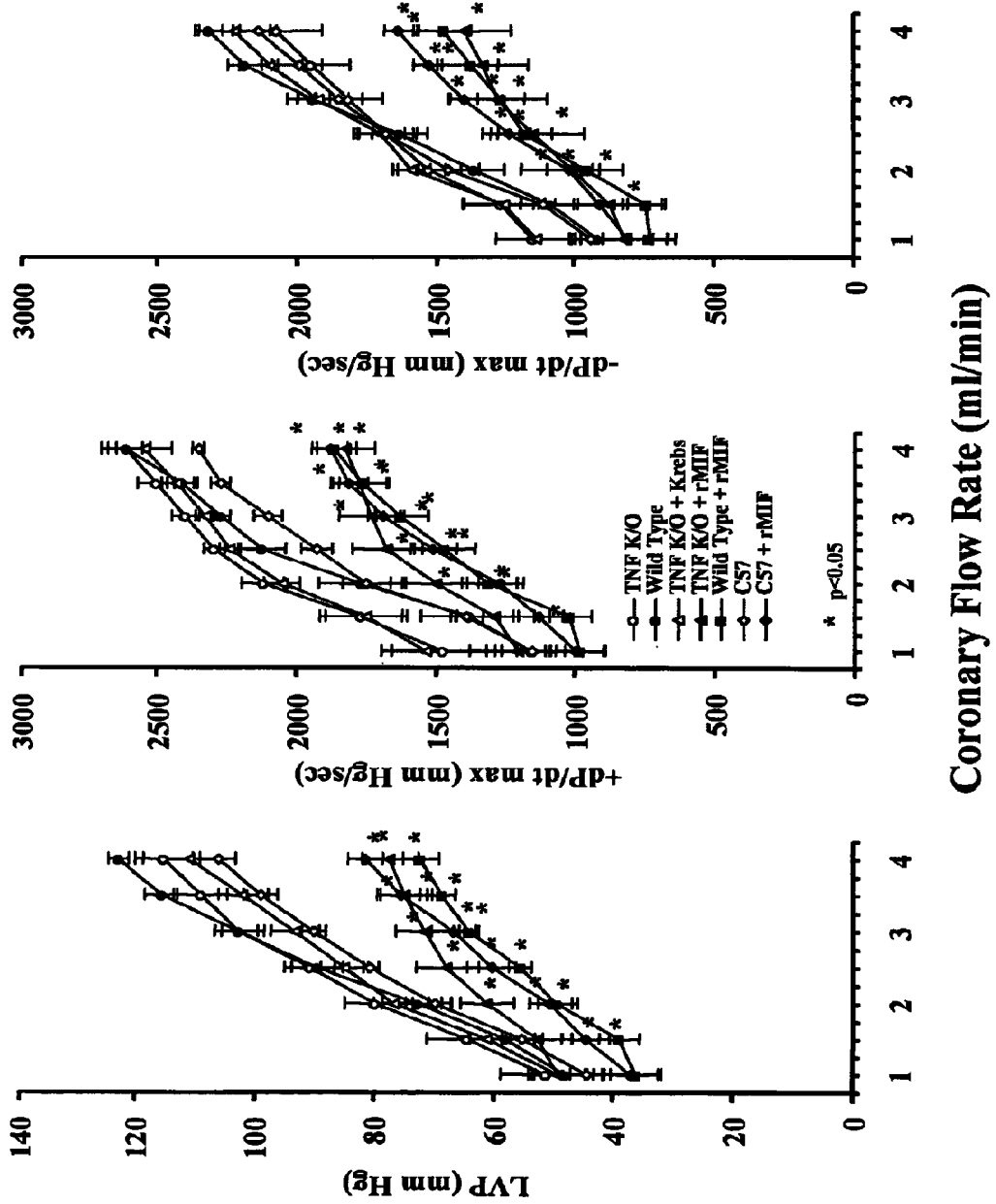
FIG. 17: Cardiac function determined by Langendorff preparation post-rMIF challenge in C57BL/6J, B6/129S, and TNFR−/− mice demonstrates rMIF mediates cardiac dysfunction independent of TNF-α signaling ex vivo. Data represents the average of 6 (C57BL/6J), 4 (B6/129S), and 4 (TNFR−/−) independent Langendorff experiments per group. *p<0.05.

MIF neutralization by anti MIF antibodies results in complete protection at 24-48 hours after LPS challenge in TNFR−/− mice. To determine the influence of TNF signaling on MIF in the pathogenesis of cardiac dysfunction in vivo, serial echocardiography (M-mode) was performed on LPS challenged TNFR−/− mice pretreated (90 minutes prior) with either of two anti-MIF monoclonal antibodies, an isotype control antibody, or no treatment (FIG. 17). At 4, 8, and 12 hours after LPS challenge, the fractional shortening percentage (FS %) of all LPS challenged mice was similarly depressed (27.7+/−0.01 FS %) compared to baseline (45.9+/− 0.002 FS %), irrespective of group assignment (FIG. 17B, C, E). At 24 hours after LPS challenge, however, mice treated with either of the two monoclonal anti-MIF antibodies demonstrated statistically significant recovery of FS % compared to LPS challenged group receive or LPS or LPS and the isotype antibody (FIG. 17). This enhanced recovery of function persisted at 48 hours where function was completely restored and LPS challenged mice receiving the isotype control were still profoundly depressed (FIG. 17D, 17E). Throughout the 48 hours, the FS % of untreated control TNFR−/− mice did not change significantly indicating that cardiac function was unaffected the testing regimen.

Serum cytokine release in wild type mice and TNFR−/− mice. Since other inflammatory cytokines have been shown to play a role in cardiac dysfunction in addition to TNF-α early after LPS challenge (i.e. IL-1β, IL-6), we determined serum levels of an inflammatory panel in wild type and TNFR−/− mice (FIG. 19). Not obvious in this figure are the release of TNF-α, IL-1β in wild type mice because of the significant increases in these cytokines in TNFR−/− mice (31.2 (4934/158 pg/ml) fold and 94.7 (7099/75 pg/ml) fold increase over wild type at 4 hours after LPS challenge) as shown in FIGS. 19A and 19B. Similarly, and IL-12 was increased in the TNFR−/− mice compared to wild type mice (and 1.7 (5128/2937 pg/ml) fold) (FIG. 19C), while IFN-γ levels were decreased 3.6 (210/58 pg/ml) fold (FIG. 19D). IL-10 and IL-6 increased similarly in wild type and TNFR−/− mice, although the delay of each of these cytokines was diminished in the TNFR−/− mice (FIGS. 19E and 19F). IL-6 levels were 8.5 fold in the TNFRKO mice at 4 hours compared to wild type mice (7099/835 pg/ml). Systemic increases in GM-CSF were identified in both wild type and TNFR−/− mice and the temporal response was nearly identical (FIG. 19G). The cytokines IL-2, IL-4, and IL-5 demonstrated no negligible modulation after LPS challenge in either wild type or TNFR−/− mice.

Serum cytokine release after MIF neutralization in wild type mice. Of the cytokines assayed for in this study, MIF neutralizing antibodies (pre-LPS challenge) only affected the modulation (increase or decrease) of serum IFN-γ and IL-10 levels after LPS challenge in wild type mice (FIG. 20). Specifically, the release of IFN-γ peak at 8 hours after LPS challenge (FIG. 19C) was attenuated 3 fold (210/69 pg/ml) (FIG. 20A). The delayed release of IL-10 in wild type mice which peaked at 48 hours was attenuated 2.9 fold (244/84 pg/ml) (FIG. 20B) after LPS challenge in wild type mice.

Coronary artery ligation: Mice were anesthetized with 1-1.5% isoflurane after which coronary artery ligation was performed. Atropine (0.75 mg/kg given intramuscularly), lidocaine (1 mg/kg intramuscularly), and saline (1 ml intraperitoneally) were given pre-operatively. Ventilation was achieved using a custom mask fitted to the mouse snout and a small animal ventilator (Harvard Apparatus, Inc., Holliston, Mass.). An incision (~5 mm) was made in the left thorax in the fourth intercostal space and pericardiotomy was performed to expose the left ventricle. The left coronary artery was occluded using 8-0 prolene approximately 2 mm under the left auricle. Subsequently, the chest was closed in layers and the negative pressure of the chest returned by syringe evacuation. Buprenorphine (0.10 mg/kg) was given once post-operatively for pain. Sham procedures were performed identically without the coronary ligation.

Figure 21:
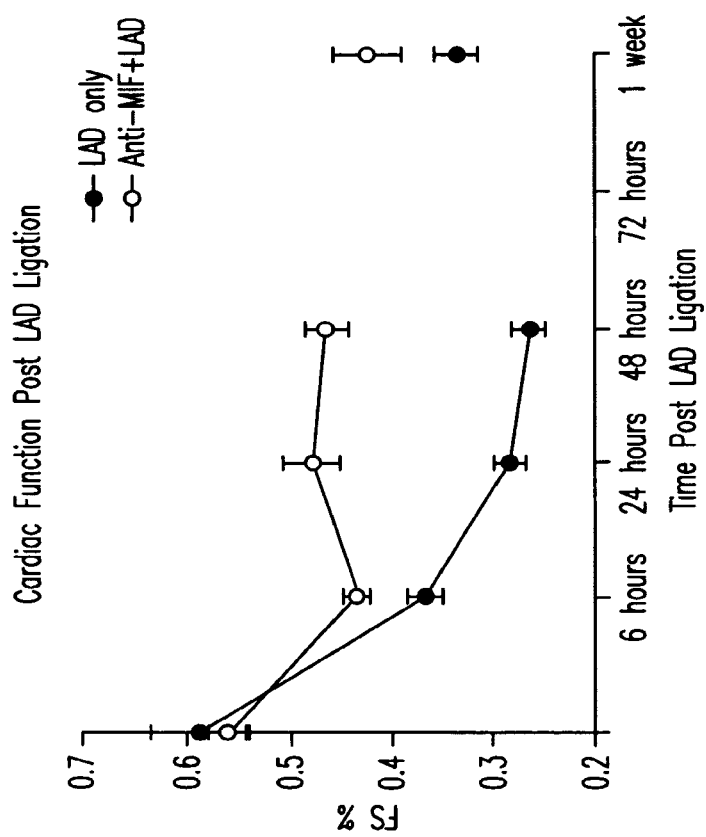
FIG. 21: Compares cardiac function (fractional shortening) in post LAD ligation with LAD only and anti-MIF+LAD.
Figure 22:
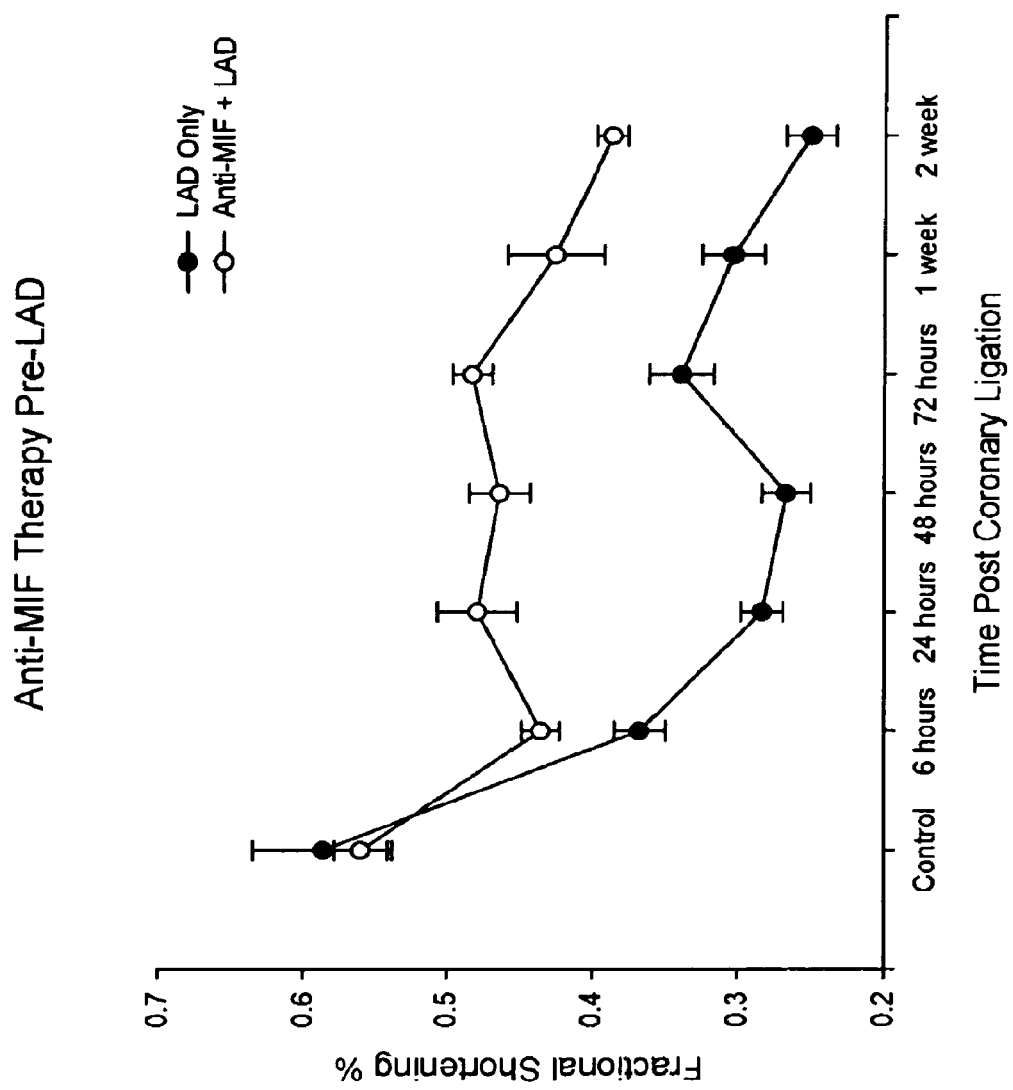
FIG. 22: Shows the effect of anti-MIF therapy pre-LAD with LAD only and anti-MIF+LAD.
Figure 24:
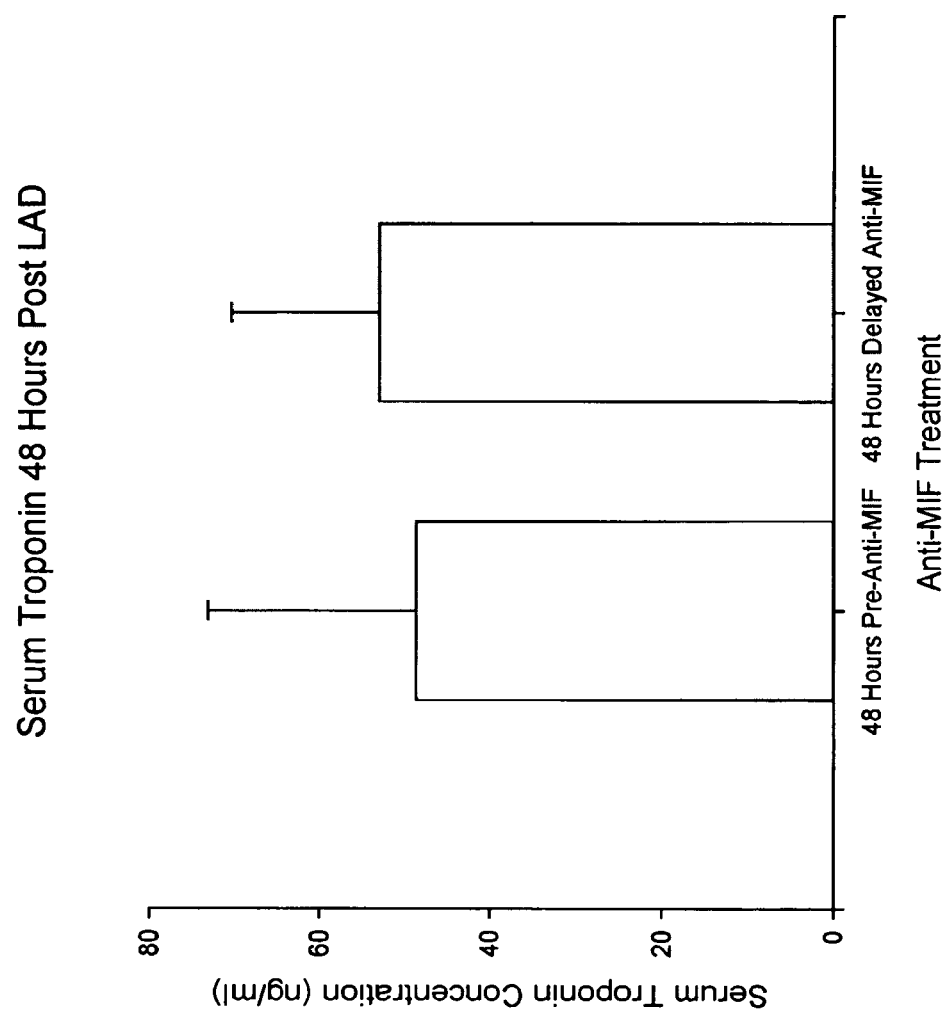
FIG. 24: Shows the serum troponin concentration 48 hrs post-LAD with pre- and delayed anti-MIF treatment.
Figure 25:
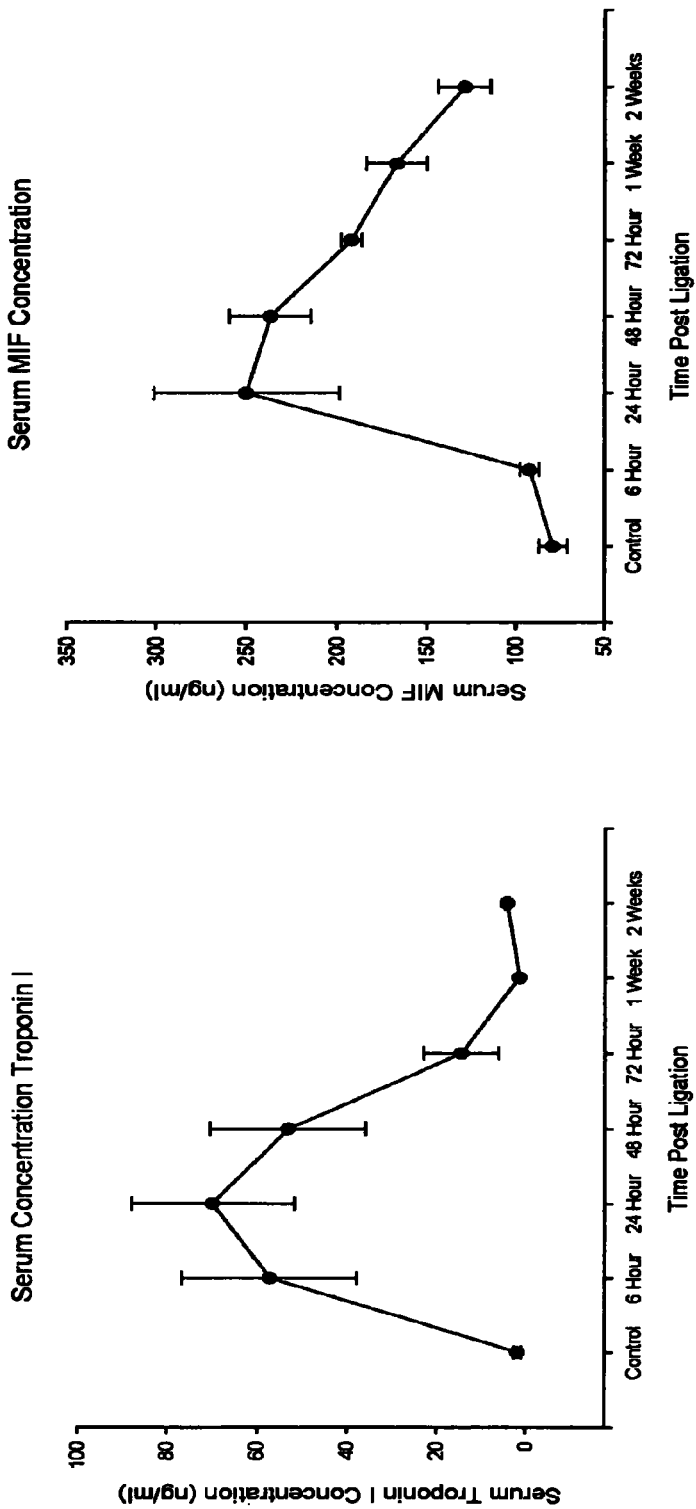
FIG. 25: Shows the serum troponin I and MIF concentrations through two weeks post ligation.
Figure 27:
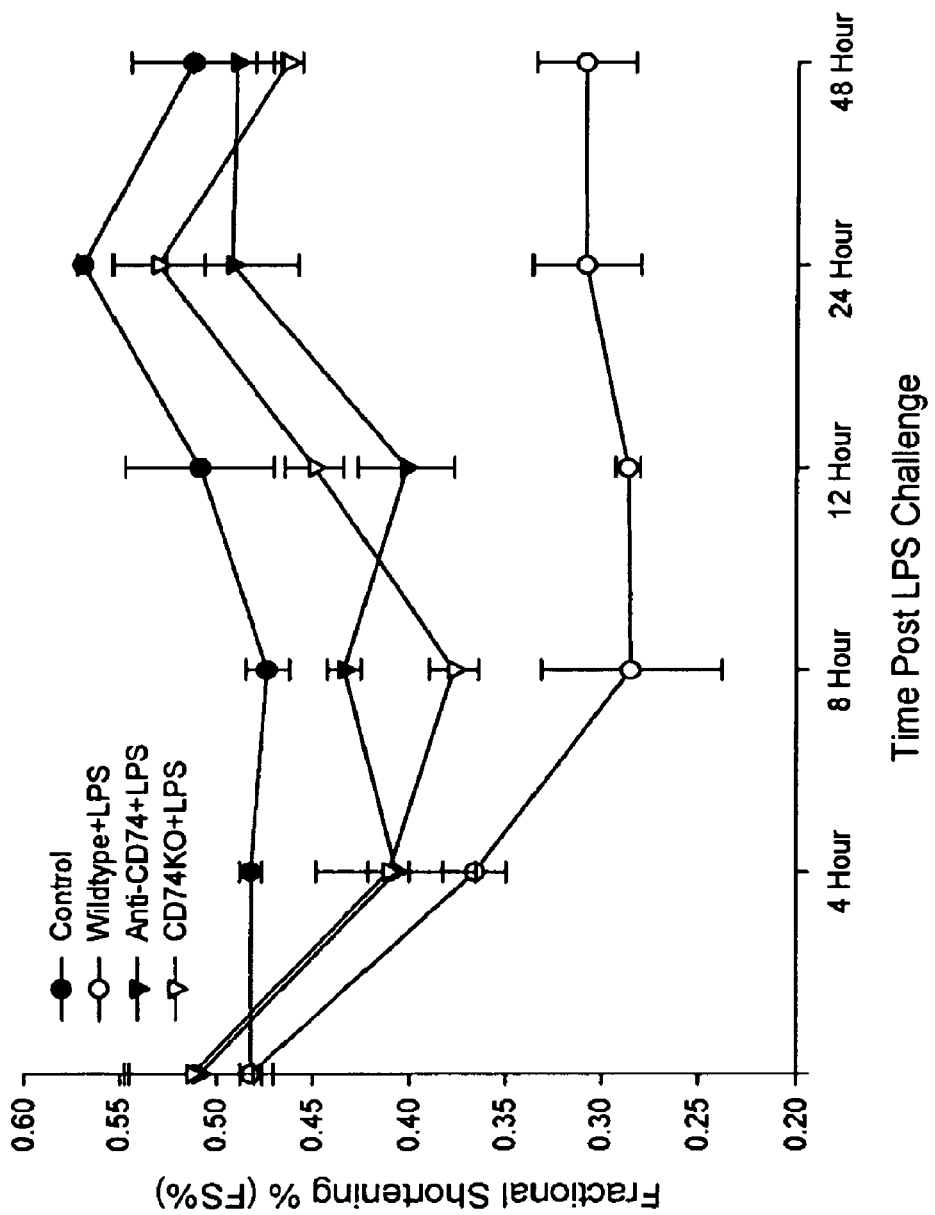
FIG. 27: Shows the echocardiography/fractional shortening of several groups from t=0 to t=48 hrs post LPS challenge.
Figure 28:
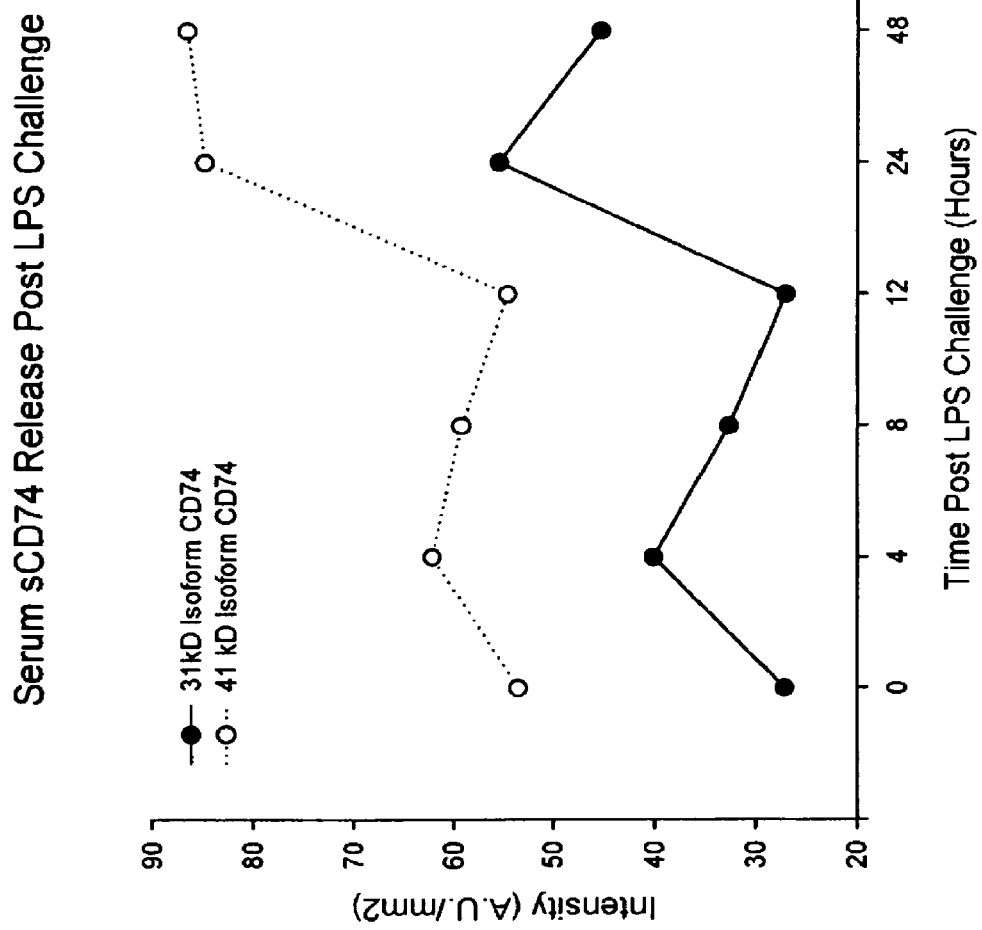
FIG. 28: Shows post LPS challenge serum sCD74 release.
Figure 29:
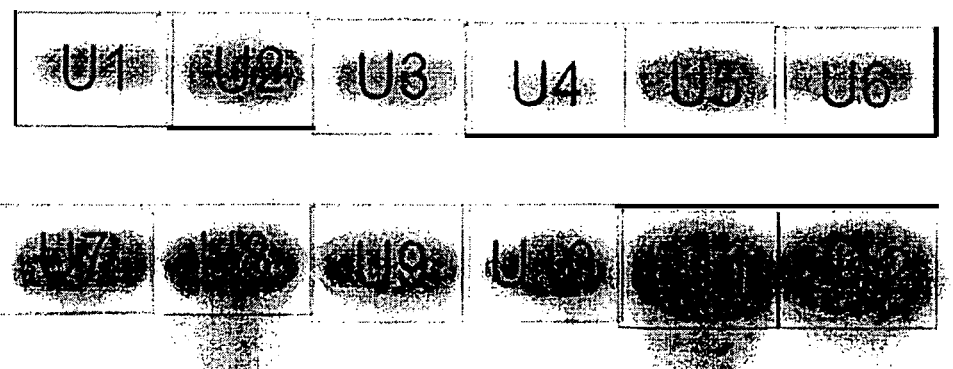
FIG. 29: Shows the CD74 series gel. See also Table 5.
Figure 30:
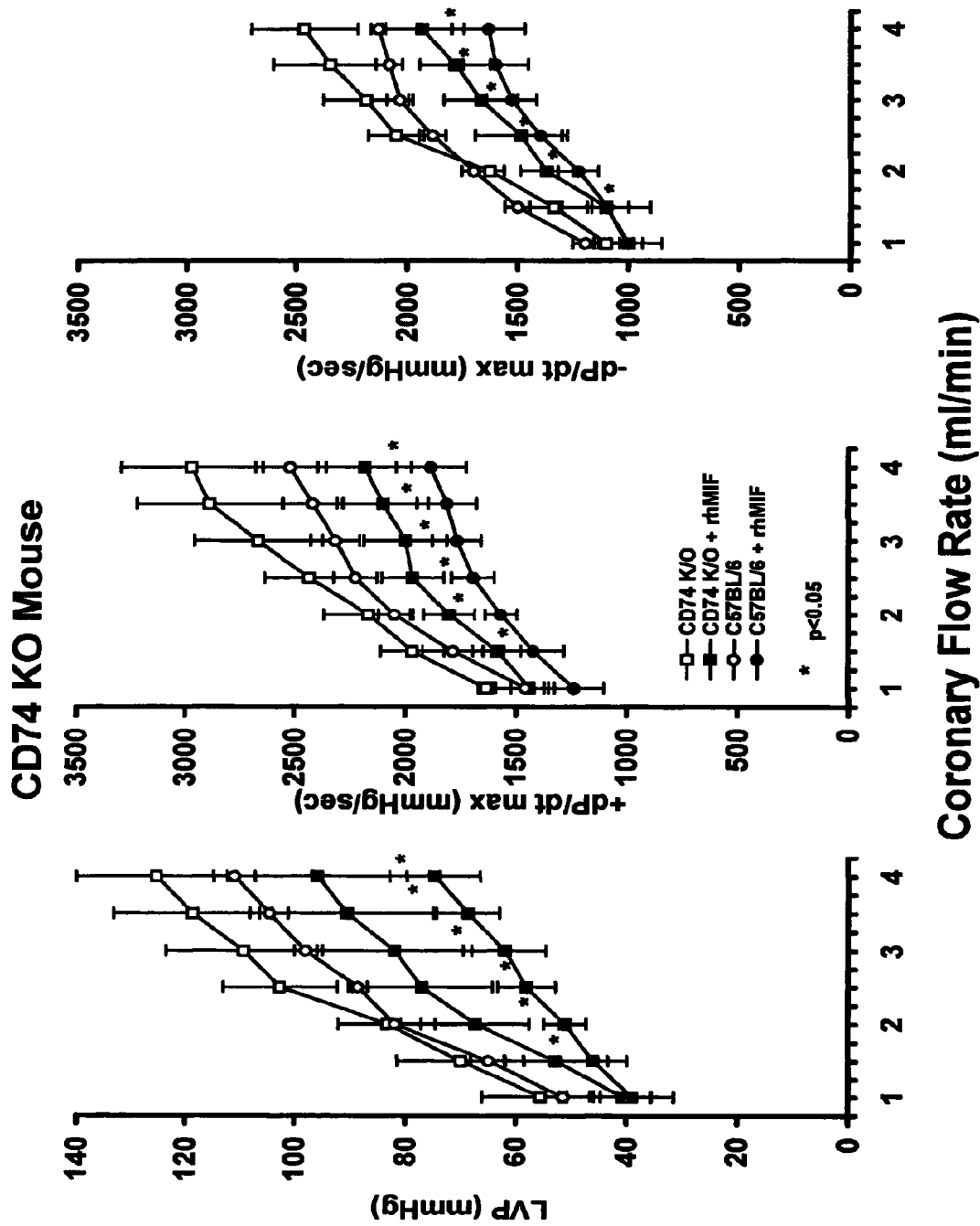
FIG. 30: Shows the coronary flow rate v. LVP, +dP/dt max, and −dP/dt max in CD74 KO Mouse.

Anti-MIF antibody: A monoclonal anti-mouse MIF IgG1 antibodies (III.D.9, gift from Cytokine PharmaScience, Inc.) and a monoclonal IgG1 isotype control antibody (HB-49, gift from Cytokine PharmaScience, Inc.) were used in the echocardiographic studies. Previous studies have demonstrated in vivo neutralization of MIF activity. FIGS. 21-25 show the results obtained in this example. FIG. 21 Compares cardiac function (fractional shortening) in post LAD ligation with LAD only and anti-MIF+LAD. FIG. 22 Shows the effect of anti-MIF therapy pre-LAD with LAD only and anti-MIF+LAD. FIG. 23 Presents cardiac function data 48 hours post-LAD for several treatment groups. FIG. 24 Shows the serum troponin concentration 48 hrs post-LAD with pre- and delayed anti-MIF treatment. FIG. 25 Shows the serum troponin I and MIF concentrations through two weeks post ligation.

TABLE 4

In vitro stabilization data from isolated hearts in the Langendorff perfusion experiments. Cardiac function is expressed as the mean ± SE. Separate analyses were performed for each parameter (left column) as a function of treatment group and coronary flow rate. A Repeated Measures ANOVA with a multiple comparison procedure employing the Bonferroni method was used to determine significant differences between groups (*$p \leq 0.05$ compared to control).

|  | TNF KO (n = 8) | Wild Type (WT) (n = 6) | P | TNF KO + Krebs (n = 4) | P | TNF KO + rMIF (n = 4) | P | WT + rMIF (n = 5) | P |
|---|---|---|---|---|---|---|---|---|---|
| LVP (mmHg) | 101.5 ± 4.3 | 103.3 ± 3.1 | NS | 102.5 ± 2.5 | NS | 66.0 ± 4.7 | 0.005 | 55.6 ± 5.9 | 0.001 |
| +dP/dt max (mmHg/sec) | 2488 ± 74 | 2280 ± 70 | NS | 2475 ± 48 | NS | 1800 ± 100 | 0.002 | 1400 ± 158 | 0.001 |
| −dP/dt max (mmHg/sec) | 2016 ± 59 | 1976 ± 87 | NS | 2175 ± 63 | NS | 1413 ± 151 | 0.03 | 1070 ± 146 | 0.005 |
| DR | 1.24 ± 0.05 | 1.16 ± 0.05 | NS | 1.14 ± 0.02 | NS | 1.30 ± 0.10 | NS | 1.32 ± 0.06 | NS |
| dP40 (mmHg/sec) | 2106 ± 63 | 1940 ± 51 | NS | 2175 ± 94 | NS | 1613 ± 105 | 0.006 | 1240 ± 174 | 0.005 |
| TPP (msec) | 70.4 ± 2.1 | 64.2 ± 4.1 | NS | 71.5 ± 2.5 | NS | 67.0 ± 2.4 | NS | 71.6 ± 1.6 | NS |
| RT90 (msec) | 71.1 ± 2.1 | 72.2 ± 4.6 | NS | 68.0 ± 3.0 | NS | 71.3 ± 4.2 | NS | 75.2 ± 2.9 | NS |
| Time to Max +dP/dt (msec) | 49.3 ± 0.4 | 44.6 ± 2.0 | NS | 48.3 ± 1.2 | NS | 47.0 ± 2.4 | NS | 49.2 ± 0.5 | NS |
| Time to Max −dP/dt (msec) | 50.0 ± 1.0 | 49.4 ± 0.8 | NS | 50.0 ± 3.5 | NS | 47.0 ± 2.4 | NS | 52.4 ± 1.7 | NS |
| CPP (mmHg) | 89.3 ± 5.7 | 86.4 ± 5.3 | NS | 70.0 ± 5.3 | NS | 91.5 ± 6.6 | NS | 84.8 ± 8.6 | NS |
| CVR (mmHg) | 59.5 ± 3.8 | 57.6 ± 3.5 | NS | 46.7 ± 3.5 | NS | 61.0 ± 4.4 | NS | 56.5 ± 5.7 | NS |
| HR (bpm) | 330 ± 14 | 362 ± 16 | NS | 318 ± 21 | NS | 335 ± 20 | NS | 338 ± 10 | NS |

Example 15

Animals: C57BL/6 mice from Charles River (12-15 weeks old) were maintained on commercial chow and tap water ad libitum. All animal protocols were reviewed and approved by the University of Texas Southwestern IACAC in compliance with the rules governing animal use published by NIH.

Example 16

MIF is secreted from cardiomyocytes following LPS challenge, and directly mediates a late onset (>6 hours) cardiac dysfunction. In immune cells, CD74 was recently determined to be the MIF receptor, exerting effects via ERK1/2 intracellular signaling pathways. To determine if CD74 mediates MIF-induced cardiac dysfunction in sepsis, we challenged: 1)

wild type mice (C57BL/6) with LPS; 2) wild type mice pretreated with anti-CD74 monocolonal neutralizing antibodies; and challenged with LPS, and 3) CD74 knock-out mice with LPS (4 mg/kg). Serial echocardiography was performed and fractional shortening (FS %) was determined. At 24 hours, significant dysfunction was observed in WT mice given LPS (FS %=31.6%±3.3%) compare to controls (FS %=58±1%). In both anti-CD74 antibody treated and CD74 knock-out mice challenged with LPS, cardiac function was significantly improved compared to wild type mice given LPS alone (FS %=49±3.6% and 53.3±2.4%, respectively, p<0.05). As CD74 expression has never been documented in the heart, we performed immunoblots and histochemistry which confirmed that CD74 was constituitively present on cardiac cell membranes and in the cytosol; and was substantially regulated after LPS challenge (nearly absent at 12 hours->4 fold decrease). FIGS. 26-30 and Tables 5-7. These data are the first to demonstrate that CD74 is expressed on cardiomyocytes and is a critical mediator of cardiac dysfunction.

TABLE 5

Gel name: CD74Series 1 (Raw 1-D Image)

| Index | Area mm2 | Mean Value INT | Std. Deviation | Density INT/mm2 |
|---|---|---|---|---|
| 1 | 60.752571 | 0.194609751 | 0.189491850143 | 27.14811295 |
| 2 | 60.752571 | 0.287409566 | 0.248436881024 | 40.09371219 |
| 3 | 60.752571 | 0.233961015 | 0.202269192827 | 32.63762488 |
| 4 | 60.752571 | 0.193959627 | 0.180271350955 | 27.05742043 |
| 5 | 60.752571 | 0.395414888 | 0.260615830635 | 55.16048369 |
| 6 | 60.752571 | 0.324963155 | 0.260421026338 | 45.33244800 |
| 7 | 60.752571 | 0.383720515 | 0.267718631786 | 53.52911561 |
| 8 | 60.752571 | 0.445625310 | 0.256556738182 | 62.16485123 |
| 9 | 60.752571 | 0.424732026 | 0.248033724362 | 59.25023237 |
| 10 | 60.752571 | 0.391370235 | 0243462155963 | 54.59625355 |
| 11 | 60.752571 | 0.607251315 | 0.202530867340 | 84.71172258 |
| 12 | 60.752571 | 0.620208919 | 0.184951399717 | 86.51931171 |

Background Subtraction Method: Local
Data units: Intensity (INT)

TABLE 6

CD74 KO MOUSE - rh/MIF added to perfusate

| | CD74 KO (n = 3) | CD74 KO + rhMIF (n = 3) | p | C57BL/6 (n = 3) | p CD74 KO | C57BL/6 + rhMIF (n = 3) | p | p CD74 KO rhMIF |
|---|---|---|---|---|---|---|---|---|
| Left Ventricular Pressure (mmHg) | 104.7 ± 12.9 | 67.3 ± 14.4 | NS | 96.0 ± 3.0 | NS | 52.7 ± 6.6 | 0.004 | NS |
| +dP/dt max (mmHg/sec) | 22533 ± 260 | 1867 ± 176 | NS | 2333 ± 33 | NS | 1417 ± 164 | 0.005 | NS |
| −dP/dt max (mmHg/sec) | 2250 ± 150 | 1433 ± 202 | 0.03 | 2033 ± 33 | NS | 1233 ± 159 | 0.008 | NS |
| Differential Ratio | 1.12 ± 0.06 | 1.32 ± 0.18 | NS | 1.15 ± 0.05 | NS | 1.15 ± 0.02 | NS | NS |
| dP40 (mmHg/sec) | 2200 ± 115 | 1662 ± 120 | 0.03 | 1867 ± 67 | NS | 1200 ± 115 | 0.007 | 0.05 |
| Time to Peak Pressue (msec) | 77.3 ± 6.3 | 69.3 ± 3.5 | NS | 78.0 ± 4.1 | NS | 74.0 ± 3.1 | NS | NS |
| Time to 90% Relaxation (msec) | 73.3 ± 3.3 | 77.3 ± 2.7 | NS | 81.0 ± 5.9 | NS | 73.3 ± 4.4 | NS | NS |
| Time to Max +dP/dt (msec) | 51.0 ± 2.1 | 45.0 ± 2.9 | NS | 51.0 ± 2.1 | NS | 47.0 ± 2.1 | NS | NS |
| Time to Max −dP/dt (msec) | 49.7 ± 3.3 | 52.7 ± 0.3 | NS | 51.7 ± 1.7 | NS | 49.0 ± 1.5 | NS | NS |
| Coronay Perfusion Pressue (mmHg) | 80.0 ± 15.5 | 86.0 ± 23.6 | NS | 80.0 ± 20.0 | NS | 86.0 ± 23 | NS | NS |
| Coronay Vascular Resistance (mmHg) | 56.3 ± 7.6 | 56.3 ± 7.7 | NS | 53.3 ± 13.3 | NS | 57.3 ± 7.7 | NS | NS |
| Heart Rate (bpm) | 313 ± 2 | 322 ± 2 | NS | 325 ± 8 | NS | 318 ± 2 | NS | NS |

TABLE 7

CD74 K/O

| | LVP | +dP/dt | −dP/dt | DR | dP40 | TPP |
|---|---|---|---|---|---|---|
| 10/24/03 | 124 | 3000 | 2400 | 1.25 | 2400 | 90 |
| 11/4/03.1 | 80 | 2100 | 1950 | 1.076923 | 2000 | 72 |
| 11/4/03.2 | 110 | 2500 | 2400 | 1.041667 | 2200 | 70 |
| n | 3 | 3 | 3 | 3 | 3 | 3 |
| x | 104.6666667 | 2533.333 | 2250 | 1.122863 | 2200 | 77.33333 |
| sd | 22.4796204 | 450.925 | 259.8076 | 0.111506 | 200 | 11.01514 |
| se | 12.97861489 | 260.3417 | 150 | 0.064378 | 115.4701 | 6.359595 |

CD74 K/O

| | RT90 | Max + d | Max − d | CPP | CVR | HR |
|---|---|---|---|---|---|---|
| 10/24/03 | 80 | 55 | 56 | 102 | 45 | 250 |
| 11/4/03.1 | 70 | 48 | 45 | 50 | 53 | 370 |
| 11/4/03.2 | 70 | 50 | 48 | 88 | 71 | 320 |
| n | 3 | 3 | 3 | 3 | 3 | 3 |
| x | 73.33333 | 51 | 49.66667 | 80 | 56.33333 | 313.3333 |
| sd | 5.773503 | 3.605551 | 5.686241 | 26.90725 | 13.31666 | 60.27714 |
| se | 3.333333 | 2.081666 | 3.282953 | 15.53491 | 7.688375 | 34.80102 |

CD74 K/O + rhMIF

| | LVP | +dP/dt | −dP/dt | DR | dP40 | TPP |
|---|---|---|---|---|---|---|
| 10/24/03 | 64 | 1800 | 1400 | 1.285714 | 1600 | 70 |
| 11/4/03.1 | 50 | 1600 | 1100 | 1.454545 | 1500 | 75 |

TABLE 7-continued

| | | | | | | |
|---|---|---|---|---|---|---|
| 11/4/03.2 | 88 | 2200 | 1800 | 1.222222 | 1900 | 63 |
| n | 3 | 3 | 3 | 3 | 3 | 3 |
| x | 67.33333333 | 1866.667 | 1433.333 | 1.320827 | 1666.667 | 69.33333 |
| sd | 19.21804707 | 305.505 | 351.1885 | 0.120076 | 208.1666 | 6.027714 |
| se | 11.09554465 | 176.3834 | 202.7588 | 0.069326 | 120.185 | 3.480102 |
| p | 0.094066011 | 0.101343 | 0.031734 | 0.104538 | 0.032901 | 0.331722 |

| | CD74 K/O | | | | | |
|---|---|---|---|---|---|---|
| | RT90 | Max + d | Max − d | CPP | CVR | HR |
| 10/24/03 | 80 | 45 | 53 | 118 | 45 | 320 |
| 11/4/03.1 | 80 | 50 | 52 | 40 | 53 | 320 |
| 11/4/03.2 | 72 | 40 | 53 | 100 | 71 | 325 |
| n | 3 | 3 | 3 | 3 | 3 | 3 |
| x | 77.33333 | 45 | 52.66667 | 86 | 56.33333 | 321.6667 |
| sd | 4.618802 | 5 | 0.57735 | 40.84116 | 13.31666 | 2.886751 |
| se | 2.666667 | 2.886751 | 0.333333 | 23.57965 | 7.688375 | 1.666667 |
| p | 0.401788 | 0.167103 | 0.414702 | 0.842117 | 1 | 0.82272 |

| | C57BL/6 | | | | | |
|---|---|---|---|---|---|---|
| | LVP | +dP/dt | −dP/dt | DR | dP40 | TPP |
| 10/27/03.1 | 90 | 2300 | 2000 | 1.15 | 2000 | 84 |
| 10/27/03.2 | 98 | 2400 | 2000 | 1.2 | 1800 | 80 |
| 10/27/03.3 | 100 | 2300 | 2100 | 1.095238 | 1800 | 70 |
| n | 3 | 3 | 3 | 3 | 3 | 3 |
| x | 96 | 2333.333 | 2033.333 | 1.148413 | 1866.667 | 78 |
| sd | 5.291502622 | 57.73503 | 57.73503 | 0.052399 | 115.4701 | 7.211103 |
| se | 3.055050463 | 33.33333 | 33.33333 | 0.030253 | 66.66667 | 4.163332 |
| pCD74 | 0.551135037 | 0.488514 | 0.231336 | 0.737615 | 0.066767 | 0.934326 |

| | C57BL/6 | | | | | |
|---|---|---|---|---|---|---|
| | RT90 | Max + d | Max − d | CPP | CVR | HR |
| 10/27/03.1 | 83 | 50 | 50 | 100 | 66.66667 | 315 |
| 10/27/03.2 | 90 | 55 | 55 | 100 | 66.66667 | 320 |
| 10/27/03.3 | 70 | 48 | 50 | 40 | 26.66667 | 340 |
| n | 3 | 3 | 3 | 3 | 3 | 3 |
| x | 81 | 51 | 51.66667 | 80 | 53.33333 | 325 |
| sd | 10.14889 | 3.605551 | 2.886751 | 34.64102 | 23.09401 | 13.22876 |
| se | 5.859465 | 2.081666 | 1.666667 | 20 | 13.33333 | 7.637626 |
| pCD74 | 0.318926 | 1 | 0.615837 | 1 | 0.854958 | 0.759751 |

| | C57BL/6 + rhMIF | | | | | |
|---|---|---|---|---|---|---|
| | LVP | +dP/dt | −dP/dt | DR | dP40 | TPP |
| 10/27/03.1 | 62 | 1650 | 1500 | 1.1 | 1400 | 72 |
| 10/27/03.2 | 40 | 1100 | 950 | 1.157895 | 1000 | 80 |
| 10/27/03.3 | 56 | 1500 | 1250 | 1.2 | 1200 | 70 |
| n | 3 | 3 | 3 | 3 | 3 | 3 |
| x | 52.66666667 | 1416.667 | 1233.333 | 1.152632 | 1200 | 74 |
| sd | 11.37248141 | 284.312 | 275.3785 | 0.050207 | 200 | 5.291503 |
| se | 6.565905201 | 164.1476 | 158.9899 | 0.028987 | 115.4701 | 3.05505 |
| p | 0.003921349 | 0.005425 | 0.007903 | 0.924639 | 0.00749 | 0.481817 |
| p-CD74MIF | 0.318808435 | 0.135201 | 0.480962 | 0.088782 | 0.048812 | 0.37059 |

| | C57BL/6 + rhMIF | | | | | |
|---|---|---|---|---|---|---|
| | RT90 | Max + d | Max − d | CPP | CVR | HR |
| 10/27/03.1 | 80 | 48 | 52 | 108 | 72 | 320 |
| 10/27/03.2 | 75 | 50 | 48 | 110 | 73.33333 | 320 |
| 10/27/03.3 | 65 | 43 | 47 | 40 | 26.66667 | 315 |
| n | 3 | 3 | 3 | 3 | 3 | 3 |
| x | 73.33333 | 47 | 49 | 86 | 57.33333 | 318.3333 |
| sd | 7.637626 | 3.605551 | 2.645751 | 39.84972 | 26.56648 | 2.886751 |
| se | 4.409586 | 2.081666 | 1.527525 | 23.00725 | 15.33816 | 1.666667 |
| p | 0.354827 | 0.245802 | 0.303548 | 0.853566 | 0.853566 | 0.441823 |
| p-CD74MIF | 0.480962 | 0.604145 | 0.078928 | 1 | 0.956318 | 0.2302 |

Example 17

Figure 31:
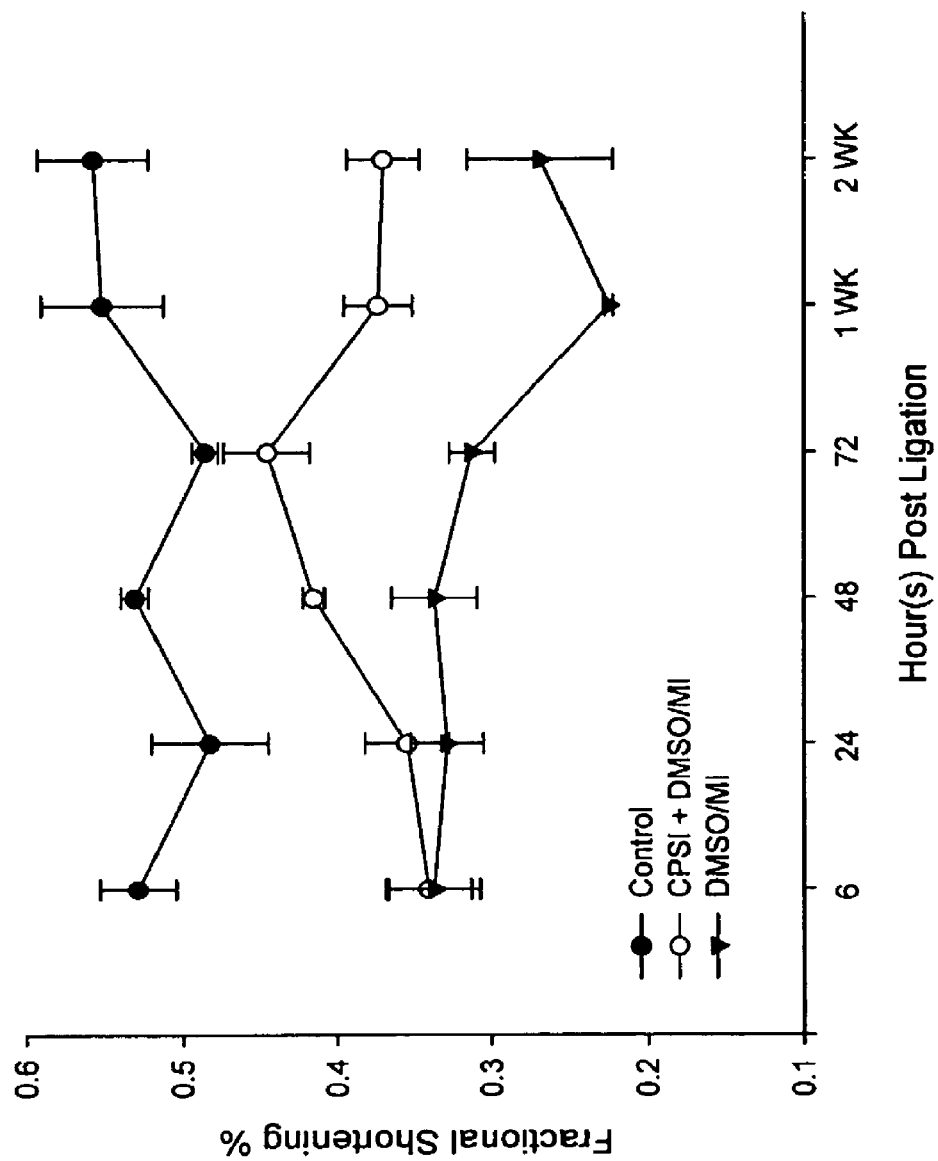
FIG. 31. Shows the hours post ligation v. fractional shortening for control, small molecule MIF inhibitor +DMSO/MI and DMSO/MI.

Coronary artery ligation. Mice were anesthetized with 1-1.5% isoflurane after which coronary artery ligation was performed. Atropine (0.075 mg/kg given intramuscularly), lidocaine (1 mg/kg intramuscularly), and saline (1 ml intraperitoneally) were given pre-operatively. Ventilation was achieved using a custom mask fitted to the mouse snout and a small animal ventilator (Harvard Apparatus, Inc., Holliston, Mass.). An incision (~5 mm) was made in the left thorax in the fourth intercostal space and pericardiotomy was performed to expose the left ventricle. The left coronary artery was occluded using 8-0 prolene approximately 2 mm under the left auricle. Subsequently, the chest was closed in layers and the negative pressure of the chest returned by syringe evacuation. An the acid methyl ester of (R)-3-(4-hydroxyphenyl)-4,5-dihydro-5-isoxazolineacetic ("ISO-1", "CPSI-26" or p-hydroxyphenol-isoxazoline methyl ester) was given at a dosage of 200 mg/kg in 25 microliters DMSO intraperitoneally daily for two weeks. Buprenorphine (0.10 mg/kg) was given once post-operatively for pain. Sham procedures were performed identically without the coronary ligation. The results are shown in FIG. 31.

Abbreviations: ABC transporters, ATP binding cassette transporters; FS %, fractional shortening %; IL-10, interleukin-1beta; IRAK, IL-1 receptor-associated kinase-M; LPS, lipopolysaccharide; MDA, malondialdehyde; MIF, (macrophage) migration inhibitory factor; Tlr-4, toll-like receptor-4; CLP, cecal ligation and puncture; Enbrel®, trade name for recombinant human TNFR:Fc (soluble TNF receptor that neutralizes TNF activity in vivo); IL-1β, interleukin-1beta; TNF-α, tumor necrosis factor-alpha; TNFR−/−, TNF-α receptor I/receptor II knock-out mice.

The entirety of each of the references cited herein, above and below, is incorporated herein by reference for all purposes.

Abe R, Shimizu T, Ohkawara A, and Nishihira J. Enhancement of macrophage migration inhibitory factor (MIF) expression in injured epidermis and cultured fibroblasts. *Biochim Biophys Acta* 1500:1-9, 2000.

Abraham E, Anzueto A, Gutierrez G, Tessler S, San Pedro G, Wunderink R, Dal Nogare A, Nasraway S, Berman S, Cooney R, Levy H, Baughman R, Rumbak M, Light R B, Poole L, Allred R, Constant J, Pennington J, and Porter S. Double-blind randomised controlled trial of monoclonal antibody to human tumour necrosis factor in treatment of septic shock. NORASEPT II Study Group. *Lancet* 351: 929-933, 1998.

Abraham E, Wunderink R, Silverman H, Pert T M, Nasraway S, Levy H, Bone R, Wenzel R P, Balk R, Allred R, and et al. Efficacy and safety of monoclonal antibody to human tumor necrosis factor alpha in patients with sepsis syndrome. A randomized, controlled, double-blind, multicenter clinical trial. TNF-alpha MAb Sepsis Study Group. *Jama* 273: 934-941, 1995.

Ammann, P., et al., "Elevation of Troponin I in Sepsis and Septic Shock", Intensive Care Med., 27, 965-969 (2001).

Bacher, M, et al., "Migration Inhibitory Factor Expression in Experimentally Induced Endotoxemia", Am. J. Pathol., 150, 235-246 (1997).

Baron P, Traber L D, Traber D L, Nguyen T, Hollyoak M, Heggers J P, and Hemdon D N. Gut failure and translocation following burn and sepsis. *J Surg Res* 57: 197-204, 1994.

Bernhagen, J., et al., "An Essential Role for Macrophage Migration Inhibitory Factor in the Tuberculin Delayed-Type Hypersensitivity Reaction", J. Exp. Med., 183, 277-282 (1996).

Bernhagen, J, et al., "Regulation of the Immune Response by Macrophage Migration Inhibitory Factor: Biological and Structural Features", J. Mol. Med., 76, 151-161 (1998).

Bernhagen, J., et al., "MIF is a Pituitary-Derived Cytokine that Potentiates Lethal Endotoxaemia", Nature, 365, 756-759 (1993).

Beutler B, Milsark I W, and Cerami A C. Passive immunization against cachectin/tumor necrosis factor protects mice from lethal effect of endotoxin. *Science* 229: 869-871, 1985.

Bhatia M and Moochhala S. Role of inflammatory mediators in the pathophysiology of acute respiratory distress syndrome. *J Pathol* 202: 145-156, 2004.

Bozza, M., et al., "Targeted Disruption of Migration Inhibitory Factor Gene Reveals Its Critical Role in Sepsis", J. Exp. Med. 189, 341-346 (1999).

Bryant, D., et al., "Cardiac Failure in Transgenic Mice with Myocardial Expression of Tumor Necrosis Factor-Alpha (TNF)", Circulation, 97, 1375-1381 (1998).

Burger-Kentischer A, Goebel H, Seiler R, Fraedrich G, Schaefer H E, Dimmeler S, Kleemann R, Bernihagen J, and Ihling C. Expression of macrophage migration inhibitory factor in different stages of human atherosclerosis. *Circulation* 105: 1561-1566, 2002.

Calandra, T., et al., "MIF as a Glucocorticoid-Induced Modulator of Cytokine Production", Nature, 377, 68-71 (1995).

Calandra, T., et al., "Macrophage Migration Inhibitory Factor (MIF): A Glucocorticoid Counter-Regulator Within the Immune System", Crit. Rev. Immunol., 17, 77-88 (1997).

Calandra, T., et al., "Protection from Septic Shock by Neutralization of Macrophage Migration Inhibitory Factor", Nat. Med., 6, 164-170 (2000).

Calandra, T., et al., "Macrophage Migration Inhibitory Factor is a Critical Mediator of the Activation of Immune Cells by Exotoxins of Gram-Positive Bacteria", Proc. Natl. Acad. Sci. USA, 95, 11383-11388 (1998).

Calandra T, Bernhagen J, Mitchell R A, and Bucala R. The macrophage is an important and previously unrecognized source of macrophage migration inhibitory factor. *J Exp Med* 179: 1895-1902, 1994.

Carlson D L, White D J, Maass D L, Nguyen R C, Giroir B, and Horton J W. I kappa B overexpression in cardiomyocytes prevents NF-kappa B translocation and provides cardioprotection in trauma. *Am J Physiol Heart Circ Physiol* 284: H804-814, 2003.

Chen G, Cao P, and Goeddel D V. TNF-induced recruitment and activation of the IKK complex require Cdc37 and Hsp90. *Mol Cell* 9: 401-410, 2002.

Chen G and Goeddel D V. TNF-R1 signaling: a beautiful pathway. *Science* 296: 1634-1635, 2002.

Chesney, J., et al., "An Essential Role for Macrophage Migration Inhibitory Factor (MIF) in Angiogenesis and the Growth of a Murine Lymphoma", Mol. Med., 5, 181-191 (1999).

Court, 0, et al., "Clinical Review: Myocardial Depression Sepsis and Septic Shock", Crit. Care, 6, 500-508 (2002).

Daryani R, LaLonde C, Zhu D, Weidner M, Knox J, and Demling R H. Effect of endotoxin and a burn injury on lung and liver lipid peroxidation and catalase activity. *J Trauma* 30: 1330-1334, 1990.

Deitch E A. Bacterial translocation of the gut flora. *J Trauma* 30: S184-189, 1990.

Deitch E A. Intestinal permeability is increased in burn patients shortly after injury. *Surgery* 107: 411-416, 1990.

Deitch E A, Maejima K, and Berg R. Effect of oral antibiotics and bacterial overgrowth on the translocation of the GI tract microflora in burned rats. *J Trauma* 25: 385-392, 1985.

de Jong Y P, Abadia-Molina A C, Satoskar A R, Clarke K, Rietdijk S T, Faubion W A, Mizoguchi E, Metz C N, Alsahli M, ten Hove T, Keates A C, Lubetsky J B, Farrell R J, Michetti P, van Deventer S J, Lolis E, David J R, Bhan A K, Terhorst C, and Sahli M A. Development of chronic colitis is dependent on the cytokine MIF. *Nat Immunol* 2: 1061-1066, 2001.

del Vecchio, M. T., et al. "Macrophage Migration Inhibitory Factor in Prostatic Adenocarcinoma: Correlation with Tumor Grading and Combination Endocrine Treatment-Related Changes", Prostate, 45, 51-57 (2000).

Dios A., et al., "Inhibition of MIF Bioactivity by Rational Design of Pharmacological Inhibitors of MIF Tautomerase Activity", J. Med. Chem., 45, 2410-2416 (2002).

Donnelly, S. C., et al., "Macrophage Migration Inhibitory Factor: A Regulator of Glucocorticoid Activity with a Critical Role in Inflammatory Disease", Mol. Med. Today., 3, 502-507 (1997).

Donnelly, S. C., et al., "Regulatory Role for Macrophage Migration Inhibitory Factor in Acute Respiratory Distress Syndrome", Nat. Med., 3, 320-323 (1997).

Eickhoff R, Wilhelm B, Renneberg H, Wennemuth G, Bacher M, Linder D, Bucala R, Seitz J, and Meinhardt A. Purification and characterization of macrophage migration inhibitory factor as a secretory protein from rat epididymis: evidences for alternative release and transfer to spermatozoa. *Mol Med* 7: 27-35, 2001.

Emmanuilidis K, Weighardt H, Matevossian E, Heidecke C D, Ulm K, Bartels H, Siewert J R, and Holzmann B. Differential regulation of systemic IL-18 and IL-12 release during postoperative sepsis: high serum IL-18 as an early predictive indicator of lethal outcome. *Shock* 18: 301-305, 2002.

Evans H G, Lewis M J, and Shah A M. Interleukin-1 beta modulates myocardial contraction via dexamethasone sensitive production of nitric oxide. *Cardiovasc Res* 27: 1486-1490, 1993.

Fingerle-Rowson, G., et al., "Regulation of Macrophage Migration Inhibitory Factor Expression by Glucocorticoids in vivo", Am. J. Pathol., 162, 47-56 (2003).

Fisher C J, Jr., Agosti J M, Opal S M, Lowry S F, Balk R A, Sadoff J C, Abraham E, Schein R M, and Benjamin E. Treatment of septic shock with the tumomecrosis factor receptor: Fc fusion protein. The Soluble TNF Receptor Sepsis Study Group. *N Engl J Med* 334: 1697-1702, 1996.

Fisher C J, Jr., Opal S M, Dhainaut J F, Stephens S, Zimmerman J L, Nightingale P, Harris S J, Schein R M, Panacek E A, Vincent J L, and et al. Influence of an anti-tumor necrosis factor monoclonal antibody on cytokine levels in patients with sepsis. The CB0006 Sepsis Syndrome Study Group. *Crit. Care Med* 21: 318-327, 1993.

Fisher C J, Jr., Dhainaut J F, Opal S M, Pribble J P, Balk R A, Slotman G J, Iberti T J, Rackow E C, Shapiro M J, Greenman R L, and et al. Recombinant human interleukin 1 receptor antagonist in the treatment of patients with sepsis syndrome. Results from a randomized, double-blind, placebo-controlled trial. Phase III rhIL-1ra Sepsis Syndrome Study Group. *Jama* 271: 1836-1843, 1994.

Fisher C J, Jr., Slotman G J, Opal S M, Pribble J P, Bone R C, Emmanuel G, Ng D, Bloedow D C, and Catalano M A. Initial evaluation of human recombinant interleukin-1 receptor antagonist in the treatment of sepsis syndrome: a randomized, open-label, placebo-controlled multicenter trial. The IL-1RA Sepsis Syndrome Study Group. *Crit. Care Med* 22: 12-21, 1994.

Flieger O, Engling A, Bucala R, Lue H, Nickel W, and Bernhagen J. Regulated secretion of macrophage migration inhibitory factor is mediated by a non-classical pathway involving an ABC transporter. *FEBS Lett* 551: 78-86, 2003.

Fukuzawa J., et al., "Contribution of Macrophage Migration Inhibitory Factor to Extracellular Signal-Regulated Kinase Activation by Oxidative Stress in Cardiomyocytes", J. Biol. Chem., 277, 24889-24895 (2002).

Fulton R J, McDade R L, Smith P L, Kienker L J, and Kettman J R, Jr. Advanced multiplexed analysis with the FlowMetrix system. *Clin Chem* 43: 1749-1756, 1997.

Gando, S., et al., "Macrophage Migration Inhibitory Factor is a Critical Mediator of Systemic Inflammatory Response Syndrome", Intensive Care Med., 27, 1187-1193 (2001).

Garner et al., Macrophage migration inhibitory factor is a cardiac-derived myocardial depressant factor. Am J. Physiol Heart Circ Physiol 285: H2500-H2509, 2003.

Garner L B, Willis M S, Carlson D L, DiMaio J M, White M D, White D J, Adams GAt, Horton J W, and Giroir B P. Macrophage migration inhibitory factor is a cardiac-derived myocardial depressant factor. *Am J Physiol Heart Circ Physiol* 285: H2500-2509, 2003.

Gardella S, Andrei C, Ferrera D, Lotti L V, Torrisi M R, Bianchi M E, and Rubartelli A. The nuclear protein HMGB1 is secreted by monocytes via a non-classical, vesicle-mediated secretory pathway. *EMBO Rep* 3: 995-1001, 2002.

Giroir, B. P., et al., "Inhibition of Tumor Necrosis Factor Prevents Myocardial Dysfunction During Burn Shock", Am. J. Physiol., 267, H118-H124 (1994).

Haudek S B, Spencer E, Bryant D D, White D J, Maass D, Horton J W, Chen Z J, and Giroir B P. Overexpression of cardiac I-kappaBalpha prevents endotoxininduced myocardial dysfunction. *Am J Physiol Heart Circ Physiol* 280: H962-968, 2001.

Haudek, et al., "Differential Regulation of Myocardial NF Kappa B Following Acute or Chronic TNF-Alpha Exposure", J. Mol. Cell. Cardiol., 33, 1263-1271 (2001).

Hesse D G, Tracey K J, Fong Y, Manogue K R, Palladino M A, Jr., Cerami A, Shires G T, and Lowry S F. Cytokine appearance in human endotoxemia and primate bacteremia. *Surg Gynecol Obstet* 166: 147-153, 1988.

Horton J W, Garcia N M, White D J, and Keffer J. Postburn cardiac contractile function and biochemical markers of postburn cardiac injury. *J Am Coll Surg* 181: 289-298, 1995.

Horton J W, White D J, Maass D L, Hybki D P, Haudek S, and Giroir B. Antioxidant vitamin therapy alters burn trauma-mediated cardiac NF-kappaB activation and cardiomyocyte cytokine secretion. *J Trauma* 50: 397-406; discussion 407-398, 2001.

Hudson, J. D., et al., "A Proinflammatory Cytokine Inhibits p53 Tumor Suppressor Activity", J. Exp. Med., 190, 1375-1382 (1999).

Kamimura, A., et al., "Intracellular Distribution of Macrophage Migration Inhibitory Factor Predicts the Prognosis of Patients with Adenocarcinoma of the Lung", Cancer, 89, 334-341 (2000).

Kettman J R, Davies T, Chandler D, Qliver K G, and Fulton R J. Classification and properties of 64 multiplexed microsphere sets. *Cytometry* 33: 234-243, 1998.

Kadokami T, McTieman C F, Kubota T, Frye C S, Bounoutas G S, Robbins P D, Watkins S C, and Feldman A M. Effects of soluble TNF receptor treatment on lipopolysaccharide-induced myocardial cytokine expression. *Am J Physiol Heart Circ Physiol* 280: H2281-2291, 2001.

Kleemann R, Hausser A, Geiger G, Mischke R, Burger-Kentischer A, Flieger 0, Johannes F J, Roger T, Calandra T, Kapumiotu A, Grell M, Finkelmeier D, Brunner H, and Bernhagen J. Intracellular action of the cytokine MIF to modulate AP-1 activity and the cell cycle through Jab1. *Nature* 408: 211-216, 2000.

Kleemann R, Kapumiotu A, Frank R W, Gessner A, Mischke R, Flieger O, Juttner S, Brunner H, and Bernhagen J. Disulfide analysis reveals a role for macrophage migration inhibitory factor (MIF) as thiol-protein oxidoreductase. *J Mol Biol* 280: 85-102, 1998.

Krishnagopalan, S., et al., "Myocardial Dysfunction in the Patient with Sepsis", Curr. Opin. Crit. Care, 8, 376-388 (2002).

Kumar, A, et al., "Tumor Necrosis Factor Alpha and Interleukin 1 Beta are Responsible for in vitro Myocardial Cell Depression Induced by Human Septic Shock Serum", J, Exp. Med., 183, 949-958 (1996).

Lai K N, Leung J C, Metz C N, Lai F M, Bucala R, and Lan H Y. Role for macrophage migration inhibitory factor in acute respiratory distress syndrome. *J Pathol* 199: 496-508, 2003.

Lan, H. Y., et al., "De Novo Renal Expression of Macrophage Migration Inhibitory Factor During the Development of Rat Crescentic Glomerulonephritis", Am. J. Pathol., 149, 1119-1127 (1996).

Lan, H. Y., et al., "Macrophage Migration Inhibitory Factor Expression in Human Renal Allograft Rejection", Transplantation, 66, 1465-1471 (1998).

Lan, H. Y., et al., "TNF-Alpha Up-Regulates Renal MIF Expression in Rat Crescentic Glomerulonephritis", Mol. Med., 3, 136-144 (1997).

Last-Barney K, Homon C A, Faanes R B, and Merluzzi V J. Synergistic and overlapping activities of tumor necrosis factor-alpha and IL-1. *J Immunol* 141: 527-530, 1988.

Leech, M, et al., "Macrophage Migration Inhibitory Factor in Rheumatoid Arthritis: Evidence of Proinflammatory Function and Regulation by Glucocorticoids", Arthritis Rheum, 42, 1601-1608 (1999).

Leech, M., et al., Involvement of Macrophage Migration Inhibitory Factor in the Evolution of Rat Adjuvant Arthritis", Arthritis Rheum., 41, 910-917 (1998).

Leech M, Metz C, Santos L, Peng T, Holdsworth S R, Bucala R, and Morand E F. Involvement of macrophage migration inhibitory factor in the evolution of rat adjuvant arthritis. Arthritis Rheum 41: 910-917, 1998.

Lefer A M. Mechanisms of cardiodepression in endotoxin shock. *Circ Shock Suppl* 1:1-8, 1979.

Lehmann, L. E., "Plasma Levels of Macrophage Migration Inhibitory Factor Are Elevated in Patients with Severe Sepsis", Intensive Care Med., 27, 1412-1415 (2001).

Leng L, Metz C N, Fang Y, Xu J, Donnelly S, Baugh J, Delohery T, Chen Y, Mitchell R A, and Bucala R. MIF signal transduction initiated by binding to CD74. *J Exp Med* 197: 1467-1476, 2003.

Lubetsky J B, Dios A, Han J, Aljabari B, Ruzsicska B, Mitchell R, Lolis E, and Al-Abed Y. The tautomerase active site of macrophage migration inhibitory factor is a potential target for discovery of novel anti-inflammatory agents. *J Biol Chem* 277: 24976-24982, 2002.

Lue, H., et al., "Macrophage Migration Inhibitory Factor (MIF): Mechanisms of Action and Role in Disease", Microbes Infect., 4, 449-460 (2002).

Makita, H., et al., "Effect of Anti-Macrophage Migration Inhibitory Factor Antibody on Lipopolysaccharide-Induced Pulmonary Neutrophil Accumulation", Am. J. Respir. Crit. Care Med., 158, 573-579 (1998).

Maass D L, White J, and Horton J W. IL-1beta and IL-6 act synergistically with TNF-alpha to alter cardiac contractile function after burn trauma. *Shock* 18: 360-366, 2002.

Meng X, Ao L, Meldrum D R, Cain B S, Shames B D, Selzman C H, Banerjee A, and Harken A H. TNF-alpha and myocardial depression in endotoxemic rats: temporal discordance of an obligatory relationship. *Am J Physiol* 275: R502-508, 1998.

Meyer-Siegler, K., et al., "Increased Stability of Macrophage Migration Inhibitory Factor (MW) in DU-145 Prostate Cancer Cells", J. Interferon Cytokine Res., 20, 769-778 (2000).

Mikulowska, A., et al., "Macrophage Migration Inhibitory Factor is Involved in the Pathogenesis of Collagen Type 11-Induced Arthritis in Mice", J. Immunol., 158, 5514-5517 (1997).

Mitchell, R. A., et al. "Tumor Growth-Promoting Properties of Macrophage Migration Inhibitory Factor (MIF)", Semin. Cancer Biol., 10, 359-366 (2000).

Mitchell R A, Metz C N, Peng T, and Bucala R. Sustained mitogen-activated protein kinase (MAPK) and cytoplasmic phospholipase A2 activation by macrophage migration inhibitory factor (MIF). Regulatory role in cell proliferation and glucocorticoid action. *J Biol Chem* 274: 18100-18106, 1999.

Mozetic-Francky B, Cotic V, Ritonja A, Zerovnik E, and Francky A. High-yield expression and purification of recombinant human macrophage migration inhibitory factor. *Protein Expr Purif* 9: 115-124, 1997.

Murphy J T, Horton J W, Purdue G F, and Hunt J L. Evaluation of troponin-I as an indicator of cardiac dysfunction after thermal injury. J Trauma 45: 700-704, 1998.

Natanson C, Hoffman W D, Suffredini A F, Eichacker P Q, and Danner R L. Selected treatment strategies for septic shock based on proposed mechanisms of pathogenesis. *Ann Intern Med* 120: 771-783, 1994.

Natanson, C., et al., "Endotoxin and Tumor Necrosis Factor Challenges in Dogs Simulate the Cardiovascular Profile of Human Septic Shock", Journal of Experimental Medicine, 169, 823-932 (1989).

Nishino T, Bernhagen J, Shiiki H, Calandra T, Dohi K, and Bucala R. Localization of macrophage migration inhibitory factor (MIF) to secretory granules within the corticotrophic and thyrotrophic cells of the pituitary gland. *Mol Med* 1: 781-788, 1995.

Ohkawara T, Nishihira J, Takeda H, Hige S, Kato M, Sugiyama T, Iwanaga T, Nakamura H, Mizue Y, and Asaka M. Amelioration of dextran sulfate sodium-induced colitis by anti-macrophage migration inhibitory factor antibody in mice. *Gastroenterology* 123: 256-270, 2002.

Okusawa S, Gelfand J A, Ikejima T, Connolly R J, and Dinarello C A. Interleukin 1 induces a shock-like state in rabbits. Synergism with tumor necrosis factor and the effect of cyclooxygenase inhibition. *J Clin Invest* 81: 1162-1172, 1988.

Ono S, Ueno C, Aosasa S, Tsujimoto H, Seki S, and Mochizuki H. Severe sepsis induces deficient interferon-gamma and interleukin-12 production, but interleukin-12 therapy improves survival in peritonitis. *Am J Surg* 182: 491-497, 2001.

Orita, M., et al., "Macrophage Migration Inhibitory Factor and the Discovery of Tautomerase Inhibitors", Curr. Pharm. Des., 8, 1297-1317 (2002).

Parker, M. M., et al., "Right Ventricular Dysfunction and Dilatation, Similar to Left Ventricular Changes, Characterize the Cardiac Depression of Septic Shock in Humans", Chest, 97, 126-131 (1990).

Parrillo J E, Burch C, Shelhamer J H, Parker M M, Natanson C, and Schuette W. A circulating myocardial depressant substance in humans with septic shock. Septic shock patients with a reduced ejection fraction have a circulating factor that depresses in vitro myocardial cell performance. *J Clin Invest* 76: 1539-1553, 1985.

Peschon J J, Torrance D S, Stocking K L, Glaccum M B, Otten C, Willis C R, Charrier K, Morrissey P J, Ware C B, and Mohler K M. TNF receptor-deficient mice reveal divergent roles for p55 and p75 in several models of inflammation. *J Immunol* 160: 943-952, 1998.

Poltorak, A., et al., "Defective LPS Signaling in C3H/HeJ and C57BL/lOScCr Mice: Mutations in Tlr4 Gene", Science, 282, 2085-2088 (1998).

Poltorak, A. et al., "Genetic and Physical Mapping of the Lps Locus: Identification of the Toll-4 Receptor as a Candidate Gene in the Critical Region", Blood Cells Mol. Dis., 24, 340-355 (1998).

Pyle M E, Korbonits M, Gueorguiev M, Jordan S, Kola B, Morris D G, Meinhardt A, Powell M P, Claret F X, Zhang Q, Metz C, Bucala R, and Grossman A B. Macrophage migration inhibitory factor expression is increased in pituitary adenoma cell nuclei. *J Endocrinol* 176: 103-110, 2003.

Qureshi, S. T., et al., "Endotoxin-Tolerant Mice Have Mutations in Toll-Like Receptor 4 (Tlr4)", J. Exp. Med., 189, 615-625 (1999).

Raeburn C D, Dinarello C A, Zimmerman M A, Calkins C M, Pomerantz B J, McIntyre R C, Jr., Harken A H, and Meng X. Neutralization of IL-18 attenuates lipopolysaccharide-induced myocardial dysfunction. *Am J Physiol Heart Circ Physiol* 283: H650-657, 2002.

Rice E K, Tesch G H, Cao Z, Cooper M E, Metz C N, Bucala R, Atkins R C, and Nikolic-Paterson D J. Induction of MIF synthesis and secretion by tubular epithelialcells: A novel action of angiotensin II. *Kidney Int* 63: 1265-1275, 2003.

Reilly J M, Cunnion R E, Burch-Whitman C, Parker M M, Shelhamer J H, and Parrillo J E. A circulating myocardial depressant substance is associated with cardiac dysfunction and peripheral hypoperfusion (lactic acidemia) in patients with septic shock. *Chest* 95: 1072-1080, 1989.

Reinhart K, Wiegand-Lohnert C, Grimminger F, Kaul M, Withington S, Treacher D, Eckart J, Willatts S, Bouza C, Krausch D, Stockenhuber F, Eiselstein J, Daum L, and Kempeni J. Assessment of the safety and efficacy of the monoclonal anti-tumor necrosis factor antibody-fragment, MAK 195F, in patients with sepsis and septic shock: a multicenter, randomized, placebo-controlled, dose-ranging study. *Crit. Care Med* 24: 733-742, 1996.

Reinhart K and Karzai W. Anti-tumor necrosis factor therapy in sepsis: update on clinical trials and lessons learned. *Crit. Care Med* 29: S121-125, 2001.

Reynolds E M, Ryan D P, Sheridan R L, and Doody D P. Left ventricular failure complicating severe pediatric burn injuries. *J Pediatr Surg* 30: 264-269; discussion 269-270, 1995.

Roger, T., et al., "MIF Regulates Innate Immune Responses Through Modulation of Toll-Like Receptor 4", Nature, 414, 920-924 (2001). As Rossi, A. G., et al., "Human Circulating Eosinophils Secrete Macrophage Migration Inhibitory Factor (MIF). Potential Role in Asthma", J. Clin. Invest., 101, 2869-2874 (1998).

Rosengren E, Bucala R, Aman P, Jacobsson L, Odh G, Metz C N, and Rorsman H. The immunoregulatory mediator macrophage migration inhibitory factor (MIF) catalyzes a tautomerization reaction. *Mol Med* 2: 143-149, 1996.

Roth, D. M., et al., "Impact of Anesthesia on Cardiac Function During Echocardiography in Mice", Am. J. Physiol., Heart Circ. Physiol., 282, H2134-H2140 (2002).

Saito H, Patterson C, Hu Z, Runge M S, Tipnis U, Sinha M, and Papaconstantinou J. Expression and self-regulatory function of cardiac interleukin-6 during endotoxemia. *Am J Physiol Heart Circ Physiol* 279: H2241-2248, 2000.

Sanders D B, Larson D F, Hunter K, Gorrnan M, and Yang B. Comparison of tumor necrosis factor-alpha effect on the expression of iNOS in macrophage and cardiac myocytes. *Perfusion* 16: 67-74, 2001.

Sambol J T, White J, Horton J W, and Deitch E A. Burn-induced impairment of cardiac contractile function is due to gut-derived factors transported in mesenteric lymph. *Shock* 18: 272-276, 2002.

Schwacha M G, Schneider C P, and Chaudry I H. Differential expression and tissue compartmentalization of the inflammatory response following thermal injury. *Cytokine* 17: 266-274, 2002.

Senter P D, Al-Abed Y, Metz C N, Benigni F, Mitchell R A, Chesney J, Han J, Gartner C G, Nelson S D, Todaro G J, and Bucala R. Inhibition of macrophage migration inhibitory factor (MIF) tautomerase and biological activities by acetaminophen metabolites. *Proc Natl Acad Sci USA* 99: 144-149, 2002.

Sessler, C. N., et al., "New Concepts in Sepsis", Curr. Qpin. Crit. Care, 8, 465-472 (2002).

Shimizu, T, et al., "High Expression of Macrophage Migration Inhibitory Factor in Human Melanoma Cells and Its Role in Tumor Cell Growth and Angiogenesis", *Biochem. Biophys. Res. Commun.*, 264, 751-758 (1999).

Shimizu T, Abe R, Ohkawara A, Mizue Y, and Nishihira J. Macrophage migration inhibitory factor is an essential immunoregulatory cytokine in atopic dermatitis. *Biochem Biophys Res Commun* 240: 173-178, 1997.

Shimizu T, Ohkawara A, Nishihira J, and Sakamoto W. Identification of macrophage migration inhibitory factor (MIF) in human skin and its immunohistochemical localization. *FEBS Lett* 381: 199-202, 1996.

Shimizu, T., et al., "Increased production of Macrophage Migration Inhibitory Factor by PBMCs of Atopic Dermatitis", J. Allergy Clin. Immunol., 104, 659-664 (1999).

Shimomura Y, Shimizu H, Takahashi M, Sato N, Uehara Y, Suwa K, Kobayashi I, Tadokoro S, and Kobayashi S. Changes in ambulatory activity and dopamine turnover in streptozotocin-induced diabetic rats. *Endocrinology* 123: 2621-2625, 1988.

Shoemaker W C, Vladeck B C, Bassin R, Printen K, Brown R S, Amato J J, Reinhard J M, and Kark A E. Burn pathophysiology in man. I. Sequential hemodynamic alterations. *J Surg Res* 14: 64-73, 1973.

Shu H B, Takeuchi M, and Goeddel D V. The tumor necrosis factor receptor 2 signal transducers TRAF2 and c-IAP1 are components of the tumor necrosis factor receptor 1 signaling complex. *Proc Natl Acad Sci USA* 93: 13973-13978, 1996.

Suffredini, A. F., et al., "The Cardiovascular Response of Normal Humans to the Administration of Endotoxin", New England Journal of Medicine, 321, 280-287 (1989).

Takahashi, M., et al., "Elevation of Plasma Levels of Macrophage Migration Inhibitory Factor in Patients with Acute Myocardial Infarction", Am. J. Cardiol., 89, 248-249 (2002).

Takahashi, M., et al., "Macrophage Migration Inhibitory Factor as a Redox-Sensitive Cytokine in Cardiac Myocytes", Cardiovasc Res., 52, 438-445 (2001).

Takahashi, et al., "Involvement of Macrophage Migration Inhibitory Factor (MIF) in the Mechanism of Tumor Cell Growth", Mol. Med., 4, 707-714 (1998).

Thomas J A, Tsen M F, White D J, and Horton J W. IRAK contributes to burn-triggered myocardial contractile dysfunction. *Am J Physiol Heart Circ Physiol* 283: H829-836, 2002.

Thomas J A, Tsen M F, White D J, and Horton J W. TLR4 inactivation and rBPI(21) block burn-induced myocardial contractile dysfunction. *Am J Physiol Heart Circ Physiol* 283: H1645-1655, 2002.

Utsunomiya T, Kobayashi M, Herndon D N, Pollard R B, and Suzuki F. A mechanism of interleukin-12 unresponsiveness associated with thermal injury. *J Surg Res* 96: 211-217, 2001.

Vignali D A. Multiplexed particle-based flow cytometric assays. *J Immunol Methods* 243: 243-255, 2000.

Wakabayashi G, Gelfand J A, Burke J F, Thompson R C, and Dinarello C A. A specific receptor antagonist for interleukin 1 prevents *Escherichia coli*-induced shock in rabbits. *Faseb J* 5: 338-343, 1991.

White, J., et al., "Development of an Acute Burn Model in Adult Mice for Studies of Cardiac Function and Cardiomyocyte Cellular Function", Shock, 16, 122-129 (2001).

White J, Carlson D L, Thompson M, Maass D L, Sanders B, Giroir B, and Horton J W. Molecular and pharmacological approaches to inhibiting nitric oxideafter burn trauma. *Am J Physiol Heart Circ Physiol* 285: H1616-1625, 2003.

White J, Maass D L, Giroir B, and Horton J W. Development of an acute burn model in adult mice for studies of cardiac function and cardiomyocyte cellular function. *Shock* 16: 122-129, 2001.

Wolfe R R. Review: acute versus chronic response to burn injury. *Circ Shock* 8: 105-115, 1981.

Yang H, COchani M, Li J, Qiang X, Tanovic M, Harris H, Susarla S, Ulloa L, Wang H, DiRaimo R, Czura C, Wang H, Roth J, Warren H, Fink M, Fenton M, Andersson U, and Tracey K J. Reversing established sepsis with antagonists of endogenous high-mobility group box 1. PNAS 101: 296-301, 2004.

Yu C M, Lai K W, Chen Y X, Huang X R, and Lan H Y. Expression of macrophage migration inhibitory factor in acute ischemic myocardial injury. *J. Histochem Cytochem* 51: 625-631, 2003.

Yu, C. M., et al., "Elevation of Plasma Level of Macrophage Migration Inhibitory Factor in Patients with Acute Myocardial Infarction", Am. J. Cardiol., 88, 774-777 (2001).

Obviously, numerous modifications and variations of the present invention are possible in light of the above teachings. It is therefore understood that within the scope of the appended claims, the invention may be practiced otherwise than as specifically recited herein.

What is claimed is:

1. A method for treating burn-injury associated cardiodepression in a subject in need thereof, comprising administering to the subject an effective amount of at least one antimacrophage migration inhibitory factor protein (anti-MIF) antibody; and optionally, at least one pharmaceutically acceptable carrier, thereby treating said burn-injury associated cardiodepression.

2. The method of claim 1, further comprising administering to the subject an effective amount of a soluble TNFR:Fc.

3. The method of claim 1, wherein the anti-MIF antibody is an anti-MIF monoclonal antibody.

4. The method of claim 1, wherein the anti-MIF antibody is an anti-MTF humanized monoclonal antibody.

\* \* \* \* \*